US012649059B2

(12) United States Patent
Huston et al.

(10) Patent No.: US 12,649,059 B2
(45) Date of Patent: Jun. 9, 2026

(54) METHODS FOR REDUCING BLEEDING IN HEMOPHILIA BY VAGUS NERVE STIMULATION TO PRIME PLATELETS

(71) Applicant: The Feinstein Institutes for Medical Research, Manhasset, NY (US)

(72) Inventors: Jared M. Huston, Old Field, NY (US); Kevin J. Tracey, Old Greenwich, CT (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 265 days.

(21) Appl. No.: 18/355,401

(22) Filed: Jul. 19, 2023

(65) Prior Publication Data

US 2024/0042201 A1 Feb. 8, 2024

Related U.S. Application Data

(60) Provisional application No. 63/395,775, filed on Aug. 5, 2022.

(51) Int. Cl.
*A61N 1/36* (2006.01)
(52) U.S. Cl.
CPC ................................ *A61N 1/36014* (2013.01)
(58) Field of Classification Search
CPC .............. A61N 1/0468; A61N 1/36014; A61N 1/36053; A61N 1/326
See application file for complete search history.

(56) References Cited

U.S. PATENT DOCUMENTS

| 2,164,121 A | 6/1939 | Pescador |
|---|---|---|
| 3,363,623 A | 1/1968 | Atwell |
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |

(Continued)

FOREIGN PATENT DOCUMENTS

| CN | 201230913 A | 5/2009 |
|---|---|---|
| CN | 101528303 A | 9/2009 |

(Continued)

OTHER PUBLICATIONS

US 6,184,239 B1, 02/2001, Puskas (withdrawn)

(Continued)

*Primary Examiner* — Alyssa M Alter
(74) *Attorney, Agent, or Firm* — Shay Glenn LLP

(57) ABSTRACT

Methods of accelerating clot formation and increasing clot deposition in a hemophiliac subject. A vagal nerve stimulator (VNS) may be implanted in a hemophiliac subject. The hemophiliac subject may have developed antibodies to factor VIII and not been administered a clotting factor within the last 48 hours. The vagus nerve of the subject may be stimulated in a manner that increases platelet intracellular calcium and/or activates splenic acetylcholine-synthesizing T lymphocytes using the implanted VNS.

5 Claims, 22 Drawing Sheets

(56)                    References Cited

U.S. PATENT DOCUMENTS

| | | |
|---|---|---|
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,690,693 A | 11/1997 | Wang et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |

(56) References Cited

U.S. PATENT DOCUMENTS

| | | | |
|---|---|---|---|
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,474 B1 | 5/2004 | Loeb et al. |
| 6,735,475 B1 | 5/2004 | Whitehurst et al. |
| 6,760,626 B1 | 7/2004 | Boveja |
| 6,762,032 B1 | 7/2004 | Nelson et al. |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 | 11/2008 | Armstrong et al. |
| 7,467,016 B2 | 12/2008 | Colbom |
| 7,544,497 B2 | 6/2009 | Sinclair et al. |
| 7,561,918 B2 | 7/2009 | Armstrong et al. |
| 7,634,315 B2 | 12/2009 | Cholette |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,869 B1 | 1/2011 | Farazi |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,504,161 B1 | 8/2013 | Kornet et al. |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |
| 9,572,983 B2 | 2/2017 | Levine et al. |
| 9,662,490 B2 | 5/2017 | Tracey et al. |
| 9,700,716 B2 | 7/2017 | Faltys et al. |
| 9,833,621 B2 | 12/2017 | Levine |
| 9,849,286 B2 | 12/2017 | Levine et al. |
| 9,987,492 B2 | 6/2018 | Tracey et al. |
| 9,993,651 B2 | 6/2018 | Faltys et al. |
| 10,166,395 B2 | 1/2019 | Tracey et al. |
| 10,220,203 B2 | 3/2019 | Faltys et al. |
| 10,238,883 B2 | 3/2019 | Jacobson |
| 10,449,358 B2 | 10/2019 | Levine et al. |
| 10,561,846 B2 | 2/2020 | Tracey et al. |
| 10,583,304 B2 | 3/2020 | Faltys et al. |
| 10,596,367 B2 | 3/2020 | Faltys et al. |
| 10,695,569 B2 | 6/2020 | Levine et al. |
| 10,716,936 B2 | 7/2020 | Faltys et al. |
| 10,912,712 B2 | 2/2021 | Tracey et al. |
| 11,051,744 B2 | 7/2021 | Levine et al. |
| 11,110,287 B2 | 9/2021 | Faltys et al. |
| 11,173,307 B2 | 11/2021 | Levine et al. |
| 11,207,518 B2 | 12/2021 | Huston et al. |
| 11,260,229 B2 | 3/2022 | Manogue |
| 11,278,718 B2 | 3/2022 | Faltys et al. |
| 11,311,725 B2 | 4/2022 | Levine et al. |
| 11,344,724 B2 | 5/2022 | Huston et al. |
| 11,383,091 B2 | 7/2022 | Faltys et al. |
| 11,406,833 B2 | 8/2022 | Faltys et al. |

(56)  References Cited

U.S. PATENT DOCUMENTS

| | | |
|---|---|---|
| 11,471,681 B2 | 10/2022 | Zitnik et al. |
| 11,517,572 B2 | 12/2022 | Kirkland et al. |
| 11,547,852 B2 | 1/2023 | Levine et al. |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0032852 A1 | 2/2003 | Perreault et al. |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015204 A1 | 1/2004 | Whitehurst et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0243211 A1 | 12/2004 | Colliou et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075694 A1 | 4/2005 | Schmeling et al. |
| 2005/0075698 A1 | 4/2005 | Phillips et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0136024 A1 | 6/2006 | Cohen et al. |
| 2006/0142802 A1 | 6/2006 | Armstrong |

(56) References Cited

U.S. PATENT DOCUMENTS

| | | |
|---|---|---|
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178706 A1 | 8/2006 | Lisogurski et al. |
| 2006/0190044 A1 | 8/2006 | Libbus et al. |
| 2006/0190053 A1 | 8/2006 | Dobak |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Paris et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0136098 A1 | 6/2007 | Smythe et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0015659 A1 | 1/2008 | Zhang |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0166348 A1 | 7/2008 | Kupper et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234780 A1 | 9/2008 | Smith |
| 2008/0234790 A1 | 9/2008 | Bayer et al. |
| 2008/0281197 A1 | 11/2008 | Wiley et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0076561 A1 | 3/2009 | Libbus et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125076 A1 | 5/2009 | Shuros et al. |
| 2009/0125079 A1 | 5/2009 | Armstrong et al. |
| 2009/0131995 A1 | 5/2009 | Sloan et al. |
| 2009/0171405 A1 | 7/2009 | Craig |
| 2009/0177112 A1 | 7/2009 | Gharib et al. |
| 2009/0182388 A1 | 7/2009 | Von Arx et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2009/0281594 A1 | 11/2009 | King et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0167937 A1 | 7/2010 | Goldknopf et al. |
| 2010/0191304 A1 | 7/2010 | Scott |
| 2010/0204766 A1 | 8/2010 | Zdeblick et al. |
| 2010/0215632 A1 | 8/2010 | Boss et al. |
| 2010/0219796 A1 | 9/2010 | Kallmyer |
| 2010/0241183 A1 | 9/2010 | DiLorenzo |
| 2010/0241195 A1 | 9/2010 | Meadows et al. |
| 2010/0241207 A1 | 9/2010 | Bluger |
| 2010/0249859 A1 | 9/2010 | DiLorenzo |
| 2010/0280500 A1 | 11/2010 | Skelton et al. |

(56) References Cited

U.S. PATENT DOCUMENTS

| | | |
|---|---|---|
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0009734 A1 | 1/2011 | Foley et al. |
| 2011/0042574 A1 | 2/2011 | Nishino et al. |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0106213 A1 | 5/2011 | Davis et al. |
| 2011/0144717 A1 | 6/2011 | Burton et al. |
| 2011/0145588 A1 | 6/2011 | Stubbs et al. |
| 2011/0152967 A1 | 6/2011 | Simon et al. |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0276112 A1 | 11/2011 | Simon et al. |
| 2011/0301658 A1 | 12/2011 | Yoo et al. |
| 2011/0301667 A1 | 12/2011 | Olson et al. |
| 2011/0307027 A1 | 12/2011 | Sharma et al. |
| 2011/0313488 A1 | 12/2011 | Hincapie Ordonez et al. |
| 2012/0053657 A1 | 3/2012 | Parker et al. |
| 2012/0065706 A1 | 3/2012 | Vallapureddy et al. |
| 2012/0136408 A1 | 5/2012 | Grill et al. |
| 2012/0179219 A1 | 7/2012 | Kisker et al. |
| 2012/0185009 A1 | 7/2012 | Kornet et al. |
| 2012/0185020 A1 | 7/2012 | Simon et al. |
| 2012/0296176 A1 | 11/2012 | Herbst |
| 2012/0302821 A1 | 11/2012 | Burnett |
| 2013/0013016 A1 | 1/2013 | Diebold |
| 2013/0018439 A1 | 1/2013 | Chow et al. |
| 2013/0066392 A1 | 3/2013 | Simon et al. |
| 2013/0066395 A1 | 3/2013 | Simon et al. |
| 2013/0071390 A1 | 3/2013 | Stadheim et al. |
| 2013/0150756 A1 | 6/2013 | Vitek et al. |
| 2013/0245718 A1 | 9/2013 | Birkholz et al. |
| 2013/0274831 A1 | 10/2013 | Otto et al. |
| 2013/0278226 A1 | 10/2013 | Cong et al. |
| 2013/0289385 A1 | 10/2013 | Lozano et al. |
| 2013/0317580 A1 | 11/2013 | Simon et al. |
| 2014/0046407 A1 | 2/2014 | Ben-Ezra et al. |
| 2014/0070761 A1 | 3/2014 | Labbe et al. |
| 2014/0105255 A1 | 4/2014 | Kutner |
| 2014/0206945 A1 | 7/2014 | Liao |
| 2014/0210524 A1 | 7/2014 | Roberts |
| 2014/0213926 A1 | 7/2014 | Vaidyanathan |
| 2014/0243714 A1 | 8/2014 | Ward et al. |
| 2014/0257425 A1 | 9/2014 | Arcot-Krishnamurthy et al. |
| 2014/0277260 A1 | 9/2014 | Khalil et al. |
| 2014/0288551 A1 | 9/2014 | Bharmi et al. |
| 2014/0324118 A1 | 10/2014 | Simon et al. |
| 2014/0330335 A1 | 11/2014 | Errico et al. |
| 2014/0336730 A1 | 11/2014 | Simon et al. |
| 2014/0371818 A1 | 12/2014 | Bond et al. |
| 2015/0018728 A1 | 1/2015 | Gross et al. |
| 2015/0031064 A1 | 1/2015 | Bilello et al. |
| 2015/0073493 A1 | 3/2015 | Kilgard et al. |
| 2015/0119956 A1 | 4/2015 | Libbus et al. |
| 2015/0133717 A1 | 5/2015 | Ghiron et al. |
| 2015/0180271 A1 | 6/2015 | Angara et al. |
| 2015/0196767 A1 | 7/2015 | Ahmed |
| 2015/0202446 A1 | 7/2015 | Franke et al. |
| 2015/0233904 A1 | 8/2015 | Nayak |
| 2015/0241447 A1 | 8/2015 | Zitnik et al. |
| 2016/0089540 A1 | 3/2016 | Bolea |
| 2016/0250097 A9 | 9/2016 | Tracey et al. |
| 2016/0279435 A1 | 9/2016 | Hyde et al. |
| 2016/0331952 A1 | 11/2016 | Faltys et al. |
| 2016/0339242 A1 | 11/2016 | Cook et al. |
| 2016/0367808 A9 | 12/2016 | Simon et al. |
| 2016/0367809 A1 | 12/2016 | Patel et al. |
| 2017/0189699 A1 | 7/2017 | Dellamano et al. |
| 2017/0202467 A1 | 7/2017 | Zitnik et al. |
| 2017/0239484 A1 | 8/2017 | Ram Rakhyani et al. |
| 2017/0245379 A1 | 8/2017 | Kang |
| 2017/0254818 A1 | 9/2017 | Haskins et al. |
| 2017/0304621 A1 | 10/2017 | Malbert et al. |
| 2017/0361093 A1 | 12/2017 | Yoo et al. |
| 2018/0021217 A1* | 1/2018 | Tracey ............ A61H 23/00 601/84 |
| 2018/0021580 A1 | 1/2018 | Tracey et al. |
| 2018/0078769 A1 | 3/2018 | Dinsmoor et al. |
| 2018/0085578 A1 | 3/2018 | Rennaker, II et al. |
| 2018/0117320 A1 | 5/2018 | Levine et al. |
| 2018/0133460 A1 | 5/2018 | Townley et al. |
| 2018/0207450 A1 | 7/2018 | Sanchez et al. |
| 2018/0289970 A1 | 10/2018 | Faltys et al. |
| 2019/0010535 A1 | 1/2019 | Pujol Onofre et al. |
| 2019/0022389 A1 | 1/2019 | Leonhardt |
| 2019/0030334 A1 | 1/2019 | Lerman et al. |
| 2019/0054295 A1 | 2/2019 | Pannu et al. |
| 2019/0090358 A1 | 3/2019 | Aresta et al. |
| 2019/0111263 A1 | 4/2019 | Levine et al. |
| 2019/0192847 A1 | 6/2019 | Faltys et al. |
| 2019/0209844 A1 | 7/2019 | Estellar et al. |
| 2019/0240490 A1 | 8/2019 | Yeh et al. |
| 2019/0290902 A1 | 9/2019 | Romero-Ortega et al. |
| 2019/0358461 A1 | 11/2019 | Steinke |
| 2020/0078589 A1 | 3/2020 | Simon et al. |
| 2020/0171312 A1 | 6/2020 | Dinsmoor et al. |
| 2020/0384259 A1 | 12/2020 | Chasensky et al. |
| 2020/0402656 A1 | 12/2020 | DeBates et al. |
| 2021/0121696 A1 | 4/2021 | Parker et al. |
| 2021/0154474 A1 | 5/2021 | Narayan et al. |
| 2021/0251848 A1 | 8/2021 | Tracey et al. |
| 2021/0315505 A1 | 10/2021 | Levine et al. |
| 2021/0353949 A1 | 11/2021 | Faltys et al. |
| 2022/0040483 A1 | 2/2022 | Levine et al. |
| 2022/0072309 A9 | 3/2022 | Levine et al. |
| 2022/0118257 A1 | 4/2022 | Huston et al. |
| 2022/0189604 A1 | 6/2022 | El-Khatib et al. |
| 2022/0193413 A1 | 6/2022 | Levine et al. |
| 2022/0212001 A1 | 7/2022 | Faltys et al. |
| 2022/0212012 A1 | 7/2022 | Manogue |
| 2022/0257941 A1 | 8/2022 | Levine et al. |
| 2022/0280797 A1 | 9/2022 | Faltys et al. |
| 2022/0362555 A1 | 11/2022 | Zitnik et al. |
| 2023/0019961 A1 | 1/2023 | Huston et al. |
| 2023/0128537 A1 | 4/2023 | Simon et al. |
| 2023/0144580 A1 | 5/2023 | Manogue |
| 2023/0158301 A1 | 5/2023 | Levine et al. |
| 2023/0241387 A1 | 8/2023 | Levine et al. |
| 2024/0172949 A1 | 5/2024 | Jumbe |
| 2024/0215900 A1 | 7/2024 | Levine et al. |
| 2024/0299745 A1 | 9/2024 | Levine et al. |
| 2025/0144416 A1 | 5/2025 | Miller et al. |
| 2025/0161682 A1 | 5/2025 | Zitnik et al. |
| 2025/0161699 A1 | 5/2025 | Faltys et al. |
| 2025/0276177 A1 | 9/2025 | Levine et al. |
| 2025/0288808 A1 | 9/2025 | Levine et al. |
| 2025/0303163 A1 | 10/2025 | Levine et al. |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| CN | 104602759 A | 5/2015 |
| CN | 106794347 A | 5/2017 |
| CN | 107510899 A | 12/2017 |
| CN | 107666937 A | 2/2018 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 207389681 | 10/2011 |
| EP | 3470111 A1 | 4/2019 |
| GB | 04133 | 2/1910 |
| GB | 2073428 A | 10/1981 |
| JP | 2017502787 | 1/2017 |
| JP | 2019517830 | 6/2019 |

(56) References Cited

FOREIGN PATENT DOCUMENTS

| KR | 20050039445 | A  | 4/2005  |
|----|-------------|----|---------|
| WO | WO93/01862  | A1 | 2/1993  |
| WO | WO97/30998  | A1 | 8/1997  |
| WO | WO98/20868  | A1 | 5/1998  |
| WO | WO00/27381  | A2 | 5/2000  |
| WO | WO00/47104  | A2 | 8/2000  |
| WO | WO01/00273  | A1 | 1/2001  |
| WO | WO01/08617  | A1 | 2/2001  |
| WO | WO01/89526  | A1 | 11/2001 |
| WO | WO02/44176  | A1 | 6/2002  |
| WO | WO02/057275 | A1 | 7/2002  |
| WO | WO03/072135 | A2 | 9/2003  |
| WO | WO2004/000413 | A2 | 12/2003 |
| WO | WO2004/064918 | A1 | 8/2004  |
| WO | WO2006/073484 | A1 | 7/2006  |
| WO | WO2006/076681 | A2 | 7/2006  |
| WO | WO2007/133718 | A2 | 11/2007 |
| WO | WO2010/005482 | A1 | 1/2010  |
| WO | WO2010/067360 | A2 | 6/2010  |
| WO | WO2010/118035 | A2 | 10/2010 |
| WO | WO2013/044207 | A1 | 3/2013  |
| WO | WO2015/009907 | A1 | 1/2015  |
| WO | WO2016/134197 | A1 | 8/2016  |
| WO | WO2019/204884 | A1 | 10/2019 |
| WO | WO2022/245878 | A1 | 11/2022 |
| WO | WO2023/141609 | A1 | 7/2023  |
| WO | WO2024/108110 | A2 | 5/2024  |
| WO | WO2024/178132 | A2 | 8/2024  |

OTHER PUBLICATIONS

US 11,745,017 B2, 09/2023, Zanos et al. (withdrawn)

Gautron et al.; Neurobiology of inflammation-associated anorexia; Frontiers in Neuroscience; 3(59); 10 pages; Jan. 8, 2010.

Li et al.; U.S. Appl. No. 18/645,129 entitled "System and methods of stimulation at trigeminaly innervated regions for disorders of cerebral perfusion," filed Apr. 24, 2024.

Levine et al.; U.S. Appl. No. 18/730,753 entitled "Treatment of inflammatory disorders," filed Jul. 19, 2024.

Chang et al.; Intermittent KHz-frequency electrical stimulation selectively engages small unmyelinated vagal afferents; bioRxiv, doi:10.1101/2021.01.30.428827. PPR:PPR276363; Feb. 1, 2021.

Chang et al.; Quantitative estimation of nerve fiber engagement by vagus nerve stimulation using physiological markers; Brain stimulation; 13(6); pp. 1617-1630; Sep. 18, 2020.

Zitnik et al.; U.S. Appl. No. 18/604,465 entitled "Batteryless implantable microsimulators," filed Mar. 13, 2024.

Levine; U.S. Appl. No. 18/605,809 entitled "Bimodal vagus nerve simulation to treat neurodegenerative disorders," filed Mar. 14, 2024.

Manogue; U.S. Appl. No. 19/002,650 entitled "Methods and apparatuses for reducing bleeding via coordinated trigeminal and vagal nerve stimulation," filed Dec. 26, 2024.

Faltys et al.; U.S. Appl. No. 19/027,362 entitled "Nerve cuff with pocket for leadless stimulator," filed Jan. 17, 2025.

Faltys et al.; U.S. Appl. No. 19/028,434 entitled "Neural stimulation devices and systems for treatment of chronic inflammation," filed Jan. 17, 2025.

Pianca et al.; Endurance training induces structural and morphoquantitative changes in rat vagus nerve; Brazilian Journal of Sports Medicine; 21(5); pp. 403-406; 2015.

Hebb et al.; Creating the Feedback Loop: Closed-Loop Neurostimulation; Neurosurgery Clinics of North America; 25(1); pp. 187-204; Jan. 28, 2014.

McLean et al.; Delayed nerve stimulation promotes axon-protective neurofilament phosphorylation, accelerates immune cell clearance and enhances remyelination in vivo in focally demyelinated nerves; PloS one; 9(10); e110174; 17 pages; Oct. 13, 2014.

Levine et al.; U.S. Appl. No. 18/893,907 entitled "Control of vagal stimulation," filed Sep. 23, 2024.

Levine et al.; U.S. Appl. No. 18/976,281 entitled "Treatment of inflammatory disorders," filed Dec. 10, 2024.

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Anderson et al.; Reflex principles of immunological homeostasis; Annu. Rev. Immunol.; 30; pp. 313-335; Apr. 2012.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.

Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.

Bernik et al., Vagus nerve stimulation attenuates endotoxic shock and cardiac TNF production, 87th Clinical Congress of the American College of Surgeons, New Orleans, LA, Oct. 9, 2001.

Bernik et al., Vagus nerve stimulation attenuates LPS-induced cardiac TNF production and myocardial depression IN shock, New York Surgical Society, New York, NY, Apr. 11, 2001.

Bernik, et al., Pharmacological stimulation of the cholinergic anti-inflammatory pathway, The Journal of Experimental Medicine, vol. 195, No. 6, pp. 781-788, Mar. 18, 2002.

Besedovsky, H., et al., Immunoregulatory feedback between interleukin-1 and glucocorticoid hormones, Science, vol. 233, No. 4764, pp. 652-654, Aug. 1986.

Bhattacharya, S.K. et al., Central muscarinic receptor subtypes and carrageenin-induced paw oedema in rats, Res. Esp. Med. vol. 191(1), pp. 65-76, Dec. 1991.

Bianchi et al., Suppression of proinflammatory cytokines in monocytes by a tetravalent guanylhydrazone, Journal of Experimental Medicine, vol. 183, pp. 927-936, Mar. 1996.

Biggio et al.; Chronic vagus nerve stimulation induces neuronal plasticity in the rat hippocampus; Int. J. Neurpsychopharmacol.; vol. 12; No. 9; pp. 1209-1221; Oct. 2009.

Blackwell, T. S. et al., Sepsis and cytokines: current status, Br. J. Anaesth., vol. 77(1), pp. 110-117, Jul. 1996.

Blum, A. et al., Role of cytokines in heart failure, Am. Heart J., vol. 135(2), pp. 181-186, Feb. 1998.

Boldyreff, Gastric and intestinal mucus, its properties and physiological importance, Acta Medica Scandinavica (journal), vol. 89, Issue 1-2, pp. 1-14, Jan./Dec. 1936.

Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.

Borovikova et al., Efferent vagus nerve activity attenuates cytokine-mediated inflammation, Society for Neuroscience Abstracts, vol. 26, No. 102, Nov. 4-9, 2000 (abstract only).

Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.

(56)                    References Cited

OTHER PUBLICATIONS

Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.

Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).

Borovikova et al., Vagotomy blocks the protective effects of I.C.V. CNI-1493 against LPS-induced shock, (Supplemental to Shock, vol. 11, 1999, Molecular, cellular, and systemic pathobioloigal aspects and therapeutic approaches, abstacts and program, Fourth international Shock Congress and 22nd Annual Conference on Shock, Philadelphia, PA, Jun. 12-16, 1999), Abstract No. 277.

Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.

Borovikova, L. V., et al., Vagus nerve stimulation attenuates the systemic inflammatory response to endotoxin, Nature, vol. 405, No. 6785: pp. 458-462, May 25, 2000.

Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.

Bulloch et al.; Characterization of choline O-acetyltransferase (ChAT) in the BALB/C mouse spleen; Int.J.Neurosci.; 76(1-2); pp. 141-149; May 1994.

Bumgardner, G. L. et al., Transplantation and cytokines, Seminars in Liver Disease, vol. 19, No. 2, Thieme Medical Publishers; pp. 189-204, © 1999.

Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.

Bushby et al.; Centiles for adult head circumference; Archives of Disease in Childhood; vol. 67(10); pp. 1286-1287; Oct. 1992.

Cano et al.; Characterization of the central nervous system innervation of the rat spleen using viral transneuronal tracing; J.Comp Neurol.; 439(1); pp. 1-18; Oct. 2001.

Caravaca et al.; A novel flexible cuff-like microelectrode for dual purpose, acute and chronic electrical interfacing with the mouse cervical vagus nerve; Journal of Neural Engineering; 14(6);066005; Nov. 1, 2017.

Caravaca et al.; Vagus nerve stimulation reduces indoethacin-induced small bowel inflammation; Frontiers in Neuroscience; 15; Article 730407; doi10.3389/fnins.2021.730407; 9 pages; ; Jan. 2022.

Carteron, N. L., Cytokines in rheumatoid arthritis: trials and tribulations, Mol. Med. Today, vol. 6(8), pp. 315-323, Aug. 2000.

Cavaillon et al.; The pro-inflammatory cytokine casade; Immune Response in the Critically Ill; Springer-Verlag Berlin Hiedelberg; pp. 37-66; Jan. 21, 2002.

Cheyuo et al.; The parasympathetic nervous system in the quest for stroke therapeutics; J. Cereb. Blood Flow Metab.; 31(5); pp. 1187-1195; May 2011.

Choi et al.; Association of first, second, and third-line bDMARDs and tsDMARD with drug survival among seropositive rheumatoid arthritis patients: cohort study in a real world setting: Seminars in Arthritis and Rheumatism; 51(4); pp. 685-691; Aug. 2021.

Cicala et al., "Linkage between inflammation and coagulation: An update on the molecular basis of the crosstalk," Life Sciences, vol. 62(20); pp. 1817-1824, Apr. 1998.

Clark et al.; Enhanced recognition memory following vagus nerve stimulation in human subjects; Nat. Neurosci.; 2(1); pp. 94-98; Jan. 1999.

Cohen, "The immunopathogenesis of sepsis," Nature., vol. 420(6917): pp. 885-891, Dec. 2002.

Corcoran, et al., The effects of vagus nerve stimulation on pro- and anti-inflammatory cytokines in humans: a preliminary report, NeuroImmunoModulation, vol. 12(5), pp. 307-309, Sep. 2005.

Crusz et al.; Inflammation and cancer; advances and new agents; Nature reviews Clinical Oncology; 12(10); pp. 584-596; doi: 10.1038/nrolinonc.2015.105; Jun. 30, 2015.

Dake; Chronic cerebrospinal venous insufficiency and multiple sclerosis: Hostory and background; Techniques Vasc. Intervent. Radiol.; 15(2); pp. 94-100; Jun. 2012.

Das, Critical advances in spticemia and septic shock, Critical Care, vol. 4, pp. 290-296, Sep. 7, 2000.

De Jonge et al.; Stimulation of the vagus nerve attenuates macrophage activation by activating the Jak2-STAT3 signaling pathway; Nature Immunology; 6(8); pp. 844-851; Aug. 2005.

Del Signore et al; Nicotinic acetylcholine receptor subtypes in the rat sympathetic ganglion: pharmacological characterization, subcellular distribution and effect of pre- and postganglionio nerve crush; J.Neuropathol.Exp.Neurol.; 63(2); pp. 138-150; Feb. 2004.

Diamond et al.; Mapping the immunological homunculus; Proc. Natl. Acad. Sci. USA; 108(9); pp. 3461-3462; Mar. 1, 2011.

Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.

Dinarello, C. A., The interleukin-1 family: 10 years of discovery, Faseb J., vol. 8, No. 15, pp. 1314-1325, Dec. 1994.

Dorr et al.; Effect of vagus nerve stimulation on serotonergic and noradrenergic transmission; J. Pharmacol. Exp. Ther.; 318(2); pp. 890-898; Aug. 2006.

Doshi et al., Evolving role of tissue factor and its pathway inhibitor, Crit. Care Med., vol. 30, suppl. 5, pp. S241-S250, May 2002.

Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.

Ellington et al., In vitro selection of RNA molecules that bind specific ligands, Nature, vol. 346, pp. 818-822, Aug. 30, 1990.

Ellrich et al.; Transcutaneous vagus nerve stimulation; Eur. Neurological Rev.; 6(4); pp. 254-256; Winter 2011.

Emery et al.; Rituximab versus an alternative TNF inhibitor in patients with rheumatoid arthritis who failed to respond to a single previous TNF inhibitor: switch-ra, a global, oberservational, comparative effectiveness study; Annals of the Rheumatic Diseases; 4(6); pp. 979-984; Jun. 2015.

Engineer et al.; Directing neural plasticity to understand and treat tinnitus; Hear. Res.; 295; pp. 58-66; Jan. 2013.

Engineer et al.; Reversing pathological neural activity using targeted plasticity; Nature; 470(7332); pp. 101-104; Feb. 3, 2011 (Author Manuscript).

Esmon, The protein C pathway, Crit. Care Med., vol. 28, suppl. 9, pp. S44-S48, Sep. 2000.

Fields; New culprits in chronic pain; Scientific American; pp. 50-57; Nov. 2009.

Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.

Fox, D. A., Cytokine blockade as a new strategy to treat rheumatoid arthritis, Arch. Intern. Med., vol. 160, pp. 437-444, Feb. 28, 2000.

Fox, et al., Use of muscarinic agonists in the treatment of Sjorgren' syndrome, Clin. Immunol., vol. 101, No. 3; pp. 249-263, Dec. 2001.

Fujii et al.; Simvastatin regulates non-neuronal cholinergic activity in T lymphocytes via CD11a-mediated pathways; J. Neuroimmunol.; 179(1-2); pp. 101-107; Oct. 2006.

Gao et al.; Investigation of specificity of auricular acupuncture points in regulation of autonomic function in anesthetized rats; Autonomic Neurosc.; 138(1-2); pp. 50-56; Feb. 29, 2008.

Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.

Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.

(56)         References Cited

OTHER PUBLICATIONS

Genovese et al.; Safety and efficacy of neurostimulation with a miniaturised vagus nerve stimulation device in patients with multidrug-refractory rheumatoid arthritis: a two-stage multicentre, randomised pilot study; The Lancet Rheumatology; 2(09); pp. e527-e538; Sep. 2020.

Ghelardini et al., S-(-)-ET 126: A potent and selective M1 antagonist in vitro and in vivo, Life Sciences, vol. 58, No. 12, pp. 991-1000, Feb. 1996.

Ghia, et al., The vagus nerve: a tonic inhibitory influence associated with inflammatory bowel disease in a murine model, Gastroenterology, vol. 131, No. 4, pp. 1122-1130, Oct. 2006.

Giebelen, et al., Stimulation of ?7 cholinergic receptors inhibits lipopolysaccharide-induced neutrophil recruitment by a tumor necrosis factor ?-independent mechanism, Shock, vol. 27, No. 4, pp. 443-447, Apr. 2007.

Gottenberg et al.; Non-TNF-targeted biologic vs a second anti-TNF drug to treat rheumatoid arthritis in patients with insufficient response to a first anti TNF drug: a randomized clinical trial; JAMA; 316(11); pp. 1172-1180; Sep. 2016.

Goyal et al., Nature of the vagal inhibitory innervation to the lower esophageal sphincter, Journal of Clinical Investigation, vol. 55, pp. 1119-1126, May 1975.

Gracie, J. A., et al., A proinflammatory role for IL-18 in rheumatoid arthritis, J. Clin. Invest., vol. 104, No. 10, pp. 1393-1401, Nov. 1999.

Granert et al., Suppression of macrophage activation with CNI-1493 increases survival in infant rats with systemic haemophilus influenzae infection, Infection and Immunity, vol. 68, No. 9, pp. 5329-5334, Sep. 2000.

Green et al., Feedback technique for deep relaxation, Psycophysiology, vol. 6, No. 3, pp. 371-377, Nov. 1969.

Gregory et al., Neutrophil-kupffer-cell interaction in host defenses to systemic infections, Immunology Today, vol. 19, No. 11, pp. 507-510, Nov. 1998.

Groves et al.; Recordings from the rat locus coeruleus during acute vagal nerve stimulation in the anaesthetised rat; Neuroscience Letters; 379(3); pp. 174-179; May 13, 2005.

Guarente, Leonard, Ph. D., Sirtuins, Aging, and Medicine; N Engl J Med ; vol. 364:pp. 2235-2244; Jun. 2011.

Guslandi, M., Nicotine treatment for ulcerative colitis, Br. J. Clin. Pharmacol., vol. 48(4), pp. 481-484, Oct. 1999.

Hansson, E.; Could chronic pain and spread of pain sensation be induced and maintained by glial activation?. Acta Physiologica, vol. 187, Issue 1-2; pp. 321R327, May/Jun. 2006.

Harrison's Principles of Internal Medicine, 13th Ed., pp. 511-515 and 1433-1435, Mar. 1994.

Hatton et al.; Vagal nerve stimulation: overview and implications for anesthesiologists; Int'l Anesthesia Research Society; vol. 103; No. 5; pp. 1241-1249; Nov. 2006.

Hirano, T., Cytokine suppresive agent improves survival rate in rats with acute pancreatitis of closed duodenal loop, J. Surg. Res., vol. 81, No. 2, pp. 224-229, Feb. 1999.

Hirao et al., The limits of specificity: an experimental analysis with RNA aptamers to MS2 coat protein variants, Mol. Divers., vol. 4, No. 2, pp. 75-89, 1999 (Accepted Jan. 13, 1999).

Hoffer et al.; Implantable electrical and mechanical interfaces with nerve and muscle; Annals of Biomedical Engineering; vol. 8; pp. 351-360; Jul. 1980.

Holladay et al., Neuronal nicotinic acetylcholine receptors as targets for drug discovery, Journal of Medicinal Chemistry, 40(26), pp. 4169-4194, Dec. 1997.

Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.

Housley et al.; Biomarkers in multiple sclerosis; Clinical Immunology; 161(1); pp. 51-58; Nov. 2015.

Hsu, et al., Analysis of efficiency of magnetic stimulation, IEEE Trans. Biomed. Eng., vol. 50(11), pp. 1276-1285, Nov. 2003.

Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.

Hu, et al., The effect of norepinephrine on endotoxin-mediated macrophage activation, J. Neuroimmunol., vol. 31(1), pp. 35-42, Jan. 1991.

Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.

Huston et al.; Transcutaneous vagus nerve stimulation reduces serum high mobility group box 1 levels and improves survival in murine sepsis; Crit. Care Med.; 35(12); pp. 2762-2768; Dec. 2007.

Hutchinson et al.; Proinflammatory cytokines oppose opioid induced acute and chronic analgesia; Brain Behav Immun.; vol. 22; No. 8; pp. 1178-1189; Nov. 2008.

Ilton et al., "Differential expression of neutrophil adhesion molecules during coronary artery surgery with cardiopulmonary bypass" Journal of Thoracic and Cardiovascular Surgery, Mosby—Year Book, inc., St. Louis, Mo, US, pp. 930-937, Nov. 1, 1999.

Jacob et al.; Detrimental role of granulocyte-colony stimulating factor in neuromyelitis optica: clinical case and histological evidence; Multiple Sclerosis Journal; 18(12); pp. 1801-1803; Dec. 2012.

Jaeger et al., The structure of HIV-1 reverse transcriptase complexed with an RNA pseudoknot inhibitor, The EMBO Journal, 17(15), pp. 4535-4542, Aug. 1998.

Jander, S. et al., Interleukin-18 is induced in acute inflammatory demyelinating polymeuropathy, J. Neuroimmunol., vol. 114, pp. 253-258, Mar. 2001.

Joshi et al., Potent inhibition of human immunodeficiency virus type 1 replection by template analog reverse transcriptase , J. Virol., 76(13), pp. 6545-6557, Jul. 2002.

Kalishevskaya et al. "The character of vagotomy-and atropin-induced hypercoagulation," Sechenov Physiological Journal of the USSR, 65(3): pp. 398-404, Mar. 1979.

Kalishevskaya et al.; Nervous regulation of the fluid state of the blood; Usp. Fiziol. Nauk;, vol. 13; No. 2; pp. 93-122; Apr.-Jun. 1982.

Kanai, T. et al., Interleukin-18 and Crohn's disease, Digestion, vol. 63, suppl. 1, pp. 37-42; 2001 (year of pub. sufficiently earlier than effective US filing date and any foreign priority date).

Katagiri, M., et al., Increased cytokine production by gastric mucosa in patients with helicobacter pylori infection, J. Clin, Gastroenterol., vol. 25, Suppl. 1, pp. S211-S214, 1997.

Katsavos et al.; Biomarkers in multiple sclerosis: an up-to-date overview; Multiple Sclerosis International; vol. 2013, Article ID 340508, 20 pages; Jan. 1, 2013.

Kawahara et al.; SIRT6 links histone H3 lysine 9 deacetylation to NF-kappaB-dependent gene expression and organismal life span.; Cell. ; vol. 136; No. 1; pp. 62-74; Jan. 2009.

Kawashima, et al., Extraneuronal cholinergic system in lymphocytes, Pharmacology & Therapeutics, vol. 86, pp. 29-48, Apr. 2000.

Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.

Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.

Khatun, S., et al., "Induction of hypercoagulability condition by chronic localized cold stress in rabbits," Thromb. and Haemost., 81(3): pp. 449-455, Mar. 1999.

Kimball, et al., Levamisole causes differential cytokine expression by elicited mouse peritoneal macrophases, Journal of Leukocyte Biology, vo. 52, No. 3, pp. 349-356, Sep. 1992 (abstract only).

Kimmings, A. N., et al., Systemic inflammatory response in acute cholangitis and after subsequent treatment, Eur. J. Surg., vol. 166, pp. 700-705, Sep. 2000.

Kirchner et al.; Left vagus nerve stimulation suppresses experimentally induced pain; Neurology; vol. 55; pp. 1167-1171; Oct. 2000.

(56)                    References Cited

OTHER PUBLICATIONS

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

Koopman et al.; Pilot study of stimulation of the cholinergic anti-inflammatory pathway with an implantable vagus nerve stimulation device in patients with rheumatoid arthritis; Arth, Rheum.; 64(10 suppl.); pp. S195; Oct. 2012.

Koopman et al.; Pilot study of stimulation of the cholinergic anti-inflammatory pathway with an implantable vagus nerve stimulation device in patients with rheumatoid arthritis; 2012 ACRIARHP Annual Meeting; Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis): (Abstract Only): on Sep. 24, 2020.

Koopman et al.; THU0237 first-in-human study of vagus nerve stimulation for rheumatoid arthritis: clinical and biomarker results through day 84; Annals of the Rheumatic Diseases; 72(Suppl 3):A245; Jun. 1, 2013 (Abstract Only).

Koopman et al.; Vagus nerve stimulation inhibits cytokine production and attenuates disease severity in rheumatoid arthritis; Proceedings of the National Academy of Sciences: 113(29); pp. 8284-8289; Jul. 19, 2016.

Krarup et al; Conduction studies in peripheral cat nerve using implanted electrodes: I. methods and findings in controls; Muscle & Nerve; vol. 11; pp. 922-932; Sep. 1988.

Kudrjashov, et al. "Reflex nature of the physiological anticoagulating system," Nature, vol. 196(4855): pp. 647-649; Nov. 17, 1962.

Kumins, N. H., et al., Partial hepatectomy reduces the endotoxin-induced peak circulating level of tumor necrosis factor in rats, Shock, vol. 5, No. 5, pp. 385-388, May 1996.

Kuznik, "Role of the vascular wall in the process of hemostatis," Usp Sovrem Biol., vol. 75(1): pp. 61-85; 1973 (the year of publication is sufficiently earlier than the effective U.S. filing date and any foreign priority date so that the particular month of publication is not in issue).

Kuznik, et al., "Blood Coagulation in stimulation of the vagus nerve in cats," Biull. Eskp. Biol. Med., vol. 78(7): pp. 7-9; 1974 (the year of publication is sufficiently earlier than the effective U.S. filing date and any foreign priority date so that the particular month of publication is not in issue).

Kuznik, et al., "Heart as an efferent regulator of the process of blood coagulation and fibrinolysis," Kardiologiia, vol. 13(3): pp. 10-17; 1973 (the year of publication is sufficiently earlier than the effective U.S. filing date and any foreign priority date so that the particular month of publication is not in issue).

Kuznik, et al., "Role of the heart and vessels in regulating blood coagulation and fibrinolysis," Kagdiologila, vol. 13(4): pp. 145-154, Apr. 1973.

Kuznik, et al., "Secretion of blood coagulation factors into saliva under conditions of hypo-and hypercoagulation," Voprosy Meditsinskoi Khimil, vol. 19(1): pp. 54-57; 1973(the year of publication is sufficiently earlier than the effective U.S. filing date and any foreign priority date so that the particular month of publication is not in issue).

Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.

Kuznik, et al., "The role of the vascular wall in the mechanism of control of blood coagulation and fibrinolysis on stimulation of the vagus nerve," Cor Vasa, vol. 17(2): pp. 151-158; 1975 (the year of publication is sufficiently earlier than the effective U.S. filing date and any foreign priority date so that the particular month of publication is not in issue).

Lang, et al., "Neurogienic control of cerebral blood flow," Experimental Neurology, 43(1): pp. 143-161, Apr. 1974.

Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.

LeNovere, N. et al., Molecular evolution of the nicotinic acetylcholine receptor: an example of multigene family in excitable cells, J. Mol. Evol., 40, pp. 155-172, Feb. 1995.

Leonard, S. et al., Neuronal nicotinic receptors: from structure to function, Nicotine & Tobacco Res. 3:203-223, Aug. 2001.

Lips et al.; Coexpression and spatial association of nicotinic acetylcholine receptor subunits alpha7 and alpha10 in rat sympathetic neurons; J.Mol.Neurosci.; 30; pp. 15-16; Feb. 2006.

Lipton, J. M. et al.; Anti-inflammatory actions of the neuroimmunomodulator ?-MSH, Immunol. Today, vol. 18, pp. 140-145, Mar. 1997.

Liu et al.; A neuroanatomical basis for electroacupuncture to drive the vagal-adrenal axis; Nature; 598(7882); pp. 641-645; 37 pages; (Author Manuscript); Oct. 2021.

Loeb et al.; Cuff electrodes for chronic stimulation and recording of peripheral nerve activity; Journal of Neuroscience Methods; vol. 64; pp. 95-103; Jan. 1996.

Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.

Manta et al.; Optimization of vagus nerve stimulation parameters using the firing activity of serotonin neurons in the rat dorsal raphe; European Neuropsychopharmacology; vol. 19; pp. 250-256; Jan. 2009 (doi: 10.1016/j.euroneuro.2008.12.001).

Martindale: The Extra Pharmacopoeia; 28th Ed. London; The Pharmaceutical Press; pp. 446-485; © 1982.

Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.

Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.

Mcguinness, P. H., et al., Increases in intrahepatic CD68 positive cells, MAC387 positive cells, and proinflammatory cytokines (particulary interleukin 18) in chronic hepatitis C infection, Gut, vol. 46(2), pp. 260-269, Feb. 2000.

Miguel-Hidalgo, J.J.; The role of glial cells in drug abuse; Current Drug Abuse Reviews; vol. 2; No. 1; pp. 76-82; Jan. 2009.

Milligan et al.; Pathological and protective roles of glia in chronic pain; Nat Rev Neurosci.; vol. 10; No. 1; pp. 23-26; Jan. 2009.

Minnich et al.; Anti-cytokine and anti-inflammatory therapies for the treatment of severe sepsis: progress and pitfalls; Proceedings of the Nutrition Society; vol. 63(3); pp. 437-441; Aug. 2004.

Mishchenko, et al., "Coagulation of the blood and fibrinolysos in dogs during vagal stimulation," Sechenov Physiological Journal of the USSR, vol. 61(1): pp. 101-107, 1975.

Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.

Molina et al., CNI-1493 attenuates hemodynamic and pro-inflammatory responses to LPS, Shock, vol. 10, No. 5, pp. 329-334, Nov. 1998.

Monaco et al.; Anti-TNF therapy:past,present, and future; International Immunology; 27(1); pp. 55-62; Jan. 2015.

Nadol et al., "Surgery of the Ear and Temporal Bone," Lippinkott Williams & Wilkins, 2nd Ed., 2005, (Publication date: Sep. 21, 2004), p. 580.

Nagashima et al., Thrombin-activatable fibrinolysis inhibitor (TAFI) deficiency is compatible with murine life, J. Clin. Invest., 109, pp. 101-110, Jan. 2002.

Nathan, C. F., Secretory products of macrophages, J. Clin. Invest., vol. 79 (2), pp. 319-326, Feb. 1987.

Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.

(56)     References Cited

OTHER PUBLICATIONS

Navzer et al.; Reversing pathological neural activity using targeted plasticity; Nature; 470(7332); pp. 101-104; Feb. 3, 2011.

Neuhaus et al.; P300 is enhanced in responders to vagus nerve stimulation for treatment of major depressive disorder; J. Affect. Disord.; 100(1-3); pp. 123-128; Jun. 2007.

Noguchi et al., Increases in Gastric acidity in response to electroacupuncture stimulation of hindlimb of anesthetized rats, Jpn. J. Physiol., 46(1), pp. 53-58, Feb. 1996.

Norton, Can ultrasound be used to stimulate nerve tissue, BioMedical Engineering OnLine, 2(1), pp. 6, Mar. 4, 2003.

Olofsson et al.; Rethinking inflammation: neural circuits in the regulation of immunity; Immunological Reviews; 248(1); pp. 188-204; Jul. 2012.

Olofsson et al.; Single-pulse and unidirectional electrical activation of the cervical vagus nerve reduces tumor necrosis factor in endotoxemia; Bioelectronic Medicine; 2(1); pp. 37-42; Jun. 2015.

Oshinsky et al.; Non-invasive vagus nerve stimulation as treatment for trigeminal allodynia; Pain; 155(5); pp. 1037-1042; May 2014.

Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.

Palov et al.; The cholinergic anti-inflammatory pathway: a missing link in neuroimmunomodulation; Molecular Medicine; 9(5); pp. 125-134; May 2003.

Pasricha et al.; Sacral nerve stimulation prompts vagally-mediated amelioration of rodent colitis; Physiological Reports; 8(1); e14294; 7 pages; Jan. 2020.

Pateyuk, et al., "Treatment of Botkin's disease with heparin," Klin. Med., vol. 51(3): pp. 113-117, Mar. 1973.

Pavlov et al.; The cholinergic anti-inflammatory pathway; Brain, Behavior, and Immunity; 19; p. 493-499; Nov. 2005.

Pavlov et al; Controlling inflammation: the cholinergic anti-inflammatory pathway; Biochem. Soc. Trans.; 34(Pt 6); pp. 1037-1040; Dec. 2006.

Payne, J. B. et al., Nicotine effects on PGE2 and IL-1 beta release by LPS-treated human monocytes, J. Perio. Res., vol. 31, No. 2, pp. 99-104, Feb. 1996.

Peuker; The nerve supply of the human auricle; Clin. Anat.; 15(1); pp. 35-37; Jan. 2002.

Pongratz et al.; The sympathetic nervous response in inflammation; Arthritis Research and Therapy; 16(504); 12 pages; retrieved from the internet (http://arthritis-research.com/content/16/6/504) ; Jan. 2014.

Prystowsky, J. B. et al., Interleukin-1 mediates guinea pig gallbladder inflammation in vivo, J. Surg. Res., vol. 71, No. 2, pp. 123-126, Aug. 1997.

Pulkki, K. J., Cytokines and cardiomyocyte death, Ann. Med., vol. 29(4), pp. 339-343, Aug. 1997.

Pullan, R. D., et al., Transdermal nicotine for active ulceratiive colitis, N. Engl. J. Med., vol. 330, No. 12, pp. 811-815, Mar. 24, 1994.

Pulvirenti et al.; Drug dependence as a disorder of neural plasticity:focus on dopamine and glutamate; Rev Neurosci.; vol. 12; No. 2; pp. 141-158; Apr./Jun. 2001.

Rahman et al.; Mammalian Sirt 1: Insights on its biological functions; Cell Communications and Signaling; vol. 9; No. 11; pp. 1-8; May 2011.

Rayner, S. A. et al., Local bioactive tumour necrosis factor (TNF) in corneal allotransplantation, Clin. Exp. Immunol., vol. 122, pp. 109-116, Oct. 2000.

Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.

Rendas-Baum et al.; Evaluating the efficacy of sequential biologic therapies for rheumatoid arthritis patients with an inadequate response to tumor necrosis factor-alpha inhibitors; Arthritis research and therapy; 13; R25; 15 pages; ; Feb. 2011.

Rinner et al.; Rat lymphocytes produce and secrete acetylcholine in dependence of differentiation and activation; J.Neuroimmunol.; 81(1-2); pp. 31-37; Jan. 1998.

Robinson et al.; Studies with the Electrocardiogram the Action of the Vagus Nerve on the Human Heart; J Exp Med; 14(3):217-234; Sep. 1911.

Romanovsky, A. A., et al.,The vagus nerve in the thermoregulatory response to systemic inflammation, Am. J. Physiol., vol. 273, No. 1 (part 2), pp. R407-R413, Jul. 1, 1997.

Rosas-Ballina et al.; Acetylcholine-synthesizing T cells relay neural signals in a vagus nerve circuit Science; 334(6052); pp. 98-101; 10 pages; (Author Manuscript); Oct. 2011.

Saghizadeh et al.; The expression of TNF? by human muscle; J. Clin. Invest.; vol. 97; No. 4; pp. 1111-1116; Feb. 15, 1996.

Saindon et al.; Effect of cervical vagotomy on sympathetic nerve responses to peripheral interleukin-1beta; Auton.Neuroscience Basic and Clinical; 87; pp. 243-248; Mar. 23, 2001.

Saito, Involvement of muscarinic M1 receptor in the central pathway of the serotonin-Induced bezold-jarisch reflex in rats, J. Autonomic Nervous System, vol. 49, pp. 61-68, Sep. 1994.

Sandborn, W. J., et al., Transdermal nicotine for mildly to moderately active ulcerative colitis, Ann. Intern. Med, vol. 126, No. 5, pp. 364-371, Mar. 1, 1997.

Sato, E., et al., Acetylcholine stimulates alveolar macrophages to release inflammatory cell chemotactic activity, Am. J. Physiol., vol. 274, pp. L970-L979, Jun. 1998.

Sato, K.Z., et al., Diversity of mRNA expression for muscarinic acetylcholine receptor subtypes and neuronal nicotinic acetylcholine receptor subunits in human mononuclear leukocytes and leukemic cell lines, Neuroscience Letters, vol. 266, pp. 17-20, Apr. 30, 1999.

Scheinman, R. I., et al., Role of transcriptional activation of 1?B? in mediation of immunosuppression by glucocorticoids, Science, vol. 270, No. 5234, pp. 283-286, Oct. 13, 1995.

Schneider et al., High-affinity ssDNA inhibitors of the review transcriptase of type 1 human immunodeficiency virus, Biochemistry, 34(29), pp. 9599-9610, Jul. 1995.

Shafer, Genotypic testing for human immunodeficiency virus type 1 drug resistance, Clinical Microbiology Reviews, vol. 15, pp. 247-277, Apr. 2002.

Shapiro et al.; Prospective, randomised trial of two doses of rFVIla (NovoSeven) in haemophilia patients with inhibitors undergoing surgery; Thromb Haernost; vol. 80(5); pp. 773-778; Nov. 1998.

Sher, M. E., et al., The influence of cigarette smoking on cytokine levels in patients with inflammatory bowel disease, Inflamm. Bowel Dis., vol. 5, No. 2, pp. 73-78, May 1999.

Shi et al.; Effects of efferent vagus nerve excitation on inflammatory response in heart tissue in rats with endotoxemia; vol. 15, No. 1; pp. 26-28; Jan. 2003 (Eng. Abstract).

Snyder et al., Correction of hemophilia B in canine and murine models using recombinant adeno-associated viral vectors; Nature Medicine, 5(1), pp. 64-70, Jan. 1999.

Sokratov, et al. "The role of choline and adrenegic structures in regulation of renal excretion of hemocoagulating compounds into the urine," Sechenov Physiological Journal of the USSR, vol. 63(12): pp. 1728-1732, 1977.

Stalcup et al., Endothelial cell functions in the hemodynamic responses to stress, Annals of the New York Academy of Sciences, vol. 401, pp. 117-131, Dec. 1982.

Steinlein, New functions for nicotine acetylcholine receptors?, Behavioural Brain Res., vol. 95(1), pp. 31-35, Sep. 1998.

Sternberg, E. M., Perspectives series: cytokines and the brain 'neural-immune interactions in health and disease,' J. Clin. Invest., vol. 100, No. 22, pp. 2641-2647, Dec. 1997.

Stevens et al.; The anti-inflammatory effect of some immunosuppressive agents; J. Path.; 97(2); pp. 367-373; Feb. 1969.

Strojnik et al.; Treatment of drop foot using and implantable peroneal underknee stimulator; Scand. J. Rehab. Med.; vol. 19(1); p. 37R43; Dec. 1986.

Strowig et al.; Inflammasomes in health and disease; Nature; vol. 481; pp. 278-286; doi: 10.1038/nature10759; Jan. 19, 2012.

Sugano et al., Nicotine inhibits the production of inflammatory mediators in U937 cells through modulation of nuclear factor-

(56)　　　　　References Cited

OTHER PUBLICATIONS kappaß activation, Biochemical and Biophysical Research Communications, vol. 252, No. 1, pp. 25-28, Nov. 9, 1998.

Suter et al.; Do glial cells control pain ?; Neuron Glia Biol.; vol. 3; No. 3; pp. 255-268; Aug. 2007.

Swick et al.; Locus coeruleus neuronal activity in awake monkeys: relationship to auditory P300-like potentials and spontaneous EEG. Exp. Brain Res.; 101(1); pp. 86-92; Sep. 1994.

Sykes, et al., An investigation into the effect and mechanisms of action of nicotine in inflammatory bowel disease, Inflamm. Res., vol. 49, pp. 311-319, Jul. 2000.

Takeuchi et al., A comparison between chinese blended medicine "Shoseiryuto" tranilast and ketotifen on the anit-allergic action in the guinea pigs, Allergy, vol. 34, No. 6, pp. 387-393, Jun. 1985 (eng. abstract).

Tekdemir et al.; A clinico-anatomic study of the auricular branch of the vagus nerve and arnold's ear-cough reflex; Surg. Radiol. Anat.; 20(4); pp. 253-257; Mar. 1998.

Toyabe, et al., Identification of nicotinic acetylcholine receptors on lymphocytes in the periphery as well as thymus in mice, Immunology, vol. 92(2), pp. 201-205, Oct. 1997.

Tracey et al., Mind over immunity, Faseb Journal, vol. 15, No. 9, pp. 1575-1576, Jul. 2001.

Tracey, K. J. et al., Anti-cachectin/TNF monoclonal antibodies prevent septic shock during lethal bacteraemia; Nature, 330: pp. 662-664, Dec. 23, 1987.

Tracey, K. J. et al., Physiology and immunology of the cholinergic antiinflammatory pathway; J Clin Invest.; vol. 117: No. 2; pp. 289-296; Feb. 2007.

Tracey, K. J. et al., Shock and tissue injury induced by recombinant human cachectin, Science, vol. 234, pp. 470-474, Oct. 24, 1986.

Tracey, K. J.; Reflex control of immunity; Nat Rev Immunol; 9(6); pp. 418-428; Jun. 2009.

Tracey, K.J., The inflammatory reflex, Nature, vol. 420, pp. 853-859, Dec. 19-26, 2002.

Tsutsui, H., et al., Pathophysiologiemmatory liver diseases; Immunol. Rev., 174:192-209, Apr. 2000.

Tuerk et al., RNA pseudoknots that inhibit human immunodeficiency virus type 1 reverse transcriptase; Proc. Natl. Acad. Sci. USA, 89, pp. 6988-6992, Aug. 1992.

Tuerk et al., Systematic evolution of ligands by exponential enrichment: RNA ligands to bacteriophage T4 DNA polymerase; Science, 249(4968), pp. 505-510, Aug. 3, 1990.

Van Der Horst et al.; Stressing the role of FoxO proteins in lifespan and disease; Nat Rev Mol Cell Biol.; vol. 8; No. 6; pp. 440-450; Jun. 2007.

Van Dijk, A. P., et al., Transdermal nicotine inhibits interleukin 2 synthesis by mononuclear cells derived from healthy volunteers, Eur. J. Clin. Invest, vol. 28, pp. 664-671, Aug. 1998.

Vanhoutte, et al., Muscarinic and beta-adrenergic prejunctional modulation of adrenergic neurotransmission in the blood vessel wall, Gen Pharmac., vol. 14(1), pp. 35-37, Jan. 1983.

Vanwesterloo, et al., The cholinergic anti-inflammatory pathway regulates the host response during septic peritonitis, The Journal of Infectious Diseases, vol. 191, pp. 2138-2148, Jun. 15, 2005.

Ventureyra, Transcutaneous vagus nerve stimulation for partial onset seizure therapy, Child's Nerv Syst, vol. 16(2), pp. 101-102, Feb. 2000.

Vida et al.; Aplha 7-cholinergic receptor mediates vagal induction of splenic norepinephrine; Journal of Immunology; 186(7); pp. 4340-4346; 16 pages; (Author Manuscript); Apr. 2011.

Vijayaraghavan, S.; Glial-neuronal interactions-implications for plasticity anddrug addiction! AAPS J.; vol. 11; No. 1; pp. 123-132; Mar. 2009.

Villa et al., Protection against lethal polymicrobial sepsis by CNI-1493, an inhibitor of pro-Inflammatory cytokine synthesis, Journal of Endotoxin Research, vol. 4, No. 3, pp. 197-204, Jun. 1997.

Von Känel, et al., Effects of non-specific ?-adrenergic stimulation and blockade on blood coagulation in hypertension, J. Appl. Physiol., vol. 94, pp. 1455-1459, Apr. 2003.

Von KäNEL, et al., Effects of sympathetic activation by adrenergic infusions on hemostasis in vivo, Eur. J. Haematol., vol. 65: pp. 357-369, Dec. 2000.

Walland et al., Compensation of muscarinic brochial effects of talsaclidine by concomitant sympathetic activation in guinea pigs; European Journal of Pharmacology, vol. 330(2-3), pp. 213-219, Jul. 9, 1997.

Wang et al.; Nicotinic acetylcholine receptor alpha7 subunit is an essential regulator of inflammation; Nature; 421; 384-388; Jan. 23, 2003.

Wang, H., et al., HMG-1 as a late mediator of endotoxin lethality in mice, Science, vol. 285, pp. 248-251, Jul. 9, 1999.

Waserman, S. et al., TNF -?dysregulation in asthma: relationship to ongoing corticosteroid therapy, Can. Respir. J., vol. 7, No. 3, pp. 229-237, May-Jun. 2000.

Watanabe, H. et al., The significance of tumor necrosis factor (TNF) levels for rejection of joint allograft, J. Reconstr. Microsurg., vol. 13, No. 3, pp. 193-197, Apr. 1997.

Wathey, J.C. et al., Numerical reconstruction of the quantal event at nicotinic synapses; Biophys. J., vol. 27: pp. 145-164, Jul. 1979.

Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.

Watkins, L.R. et al., Implications of immune-to-brain communication for sickness and pain, Proc. Natl. Acad. Sci. U.S.A., vol. 96(14), pp. 7710-7713, Jul. 6, 1999.

Webster's Dictionary, definition of "intrathecal", online version accessed Apr. 21, 2009.

Weiner, et al., "Inflammation and therapeutic vaccination in CNS diseases," Nature., vol. 420(6917): pp. 879-884, Dec. 19-26, 2002.

Westerheide et al.; Stress-inducible regulation of heat shock factor 1 by the deacetylase SIRT1.; Science; Vo. 323; No. 5717; pp. 1063-1066; Feb.—2009.

Whaley, K. et al., C2 synthesis by human monocytes is modulated by a nicotinic cholinergic receptor, Nature, vol. 293, pp. 580-582, Oct. 15, 1981.

Woiciechowsky, C. et al., Sympathetic activation triggers systemic interleukin-10 release in immunodepression induced by brain injury, Nature Med., vol. 4, No. 7, pp. 808-813, Jul. 1998.

Yang et al.; Acetylcholine inhibits LPS-induced MMP-9 production and ccell migration via the alpha7 nAChR-JAK2/STATS pathway in RAW264.7 cells; Cellular Physiology and Biochemistry: 36(5); pp. 2025-2038; (the year of publication is sufficiently earlier than the effective U.S. filing date and any foreign priority date so that the particular month of publication is not in issue) 2015.

Yeh, S.S. et al., Geriatric cachexia: the role of cytokines, Am. J. Clin. Nutr., vol. 70(2), pp. 183-197, Aug. 1999.

Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.

Zamotrinsky et al.; Vagal neurostimulation in patients with coronary artery disease; Auton. Neurosci.; 88(1-2); pp. 109-116; Apr. 2001.

Zhang et al., Tumor necrosis factor, The Cytokine Handbook, 3rd ed., Ed. Thompson, Academic Press, pp. 517-548, Jul. 1, 1998.

Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.

Zhang et al.; Roles of SIRT1 in the acute and restorative phases following induction of inflammation.; J Biol Chem.; vol. 285; No. 53; pp. 41391-41401; Dec.—2010.

Zhao et al.; Transcutaneous auricular vagus stimulation protects endotoxemic rat from lipopolysaccharide-induced inflammation, Evid. Based Complement Alternat. Med.; vol. 2012; Article ID 627023; 10 pages; Dec. 29, 2012.

Zitnik et al.; Treatment of chronic inflammatory diseases with implantable medical devices; Cleveland Clinic Journal of Medicine; 78(Suppl 1); pp. S30-S34; Aug. 2011.

Zanos et al.; U.S. Appl. No. 18/335,116 entitled "Systems and methods for vagus nerve stimulation," filed Jun. 14, 2023.

(56) References Cited

OTHER PUBLICATIONS

Yang et al.; Axon myelination and electrical stimulation in a microfluidic, compartmentalized cell culture platform; Neuromolecular medicine; vol. 14; pp. 112-118; Jun. 2012.

Calle et al.; U.S. Appl. No. 18/562,283 entitled "Neurostimulation parameter authentication and expiration system for nuerostimulation," filed Nov. 17, 2023.

Levine et al.; U.S. Appl. No. 18/431,974 entitled "Vagus nerve stimulation pre-screening test," filed Feb. 3, 2024.

Datta-Chaudhuri et al.; U.S. Appl. No. 19/130,899 entitled "Systems and methods for closed-loop neuromodulation using multiple biological signals," filed May 16, 2025.

Shah et al.; Electrical stimulation of the infraorbital nerve induces diving reflex in a dose-controlled manner; In2020 42nd Annual International Conference of the IEEE Engineering in Medicine & Biology Society (EMBC); IEEE; pp. 5208-5211; Jul. 20, 2020 (Abstract only).

* cited by examiner

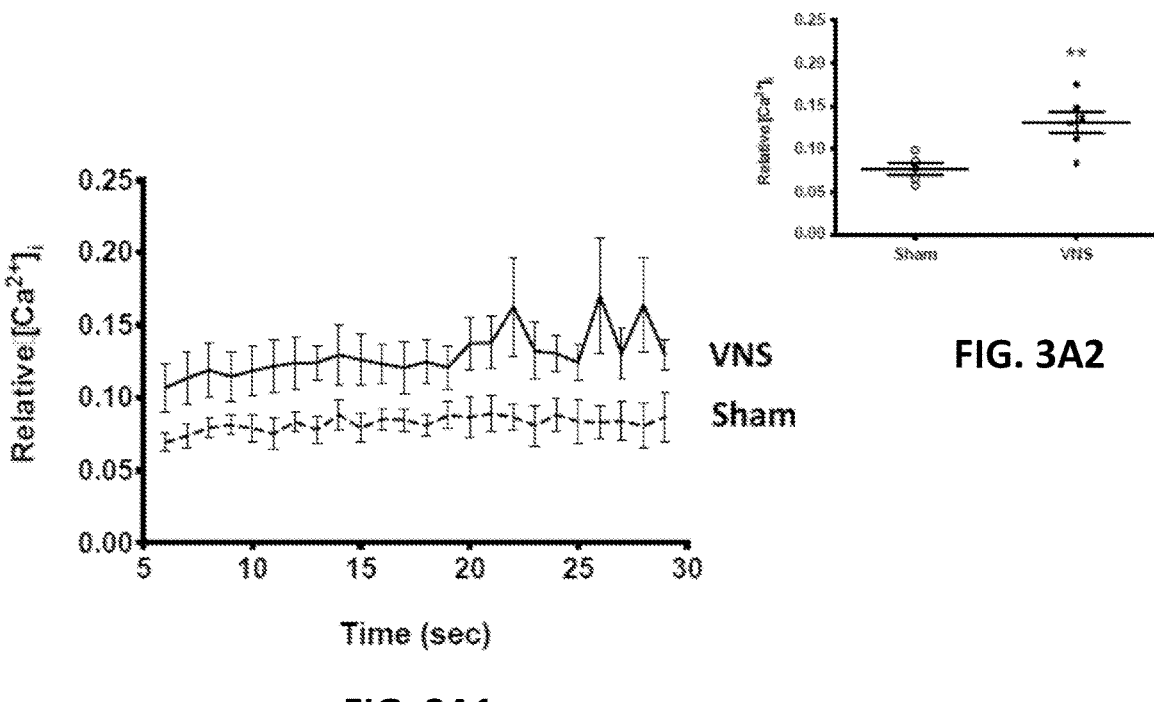
FIG. 3A2
FIG. 3A1
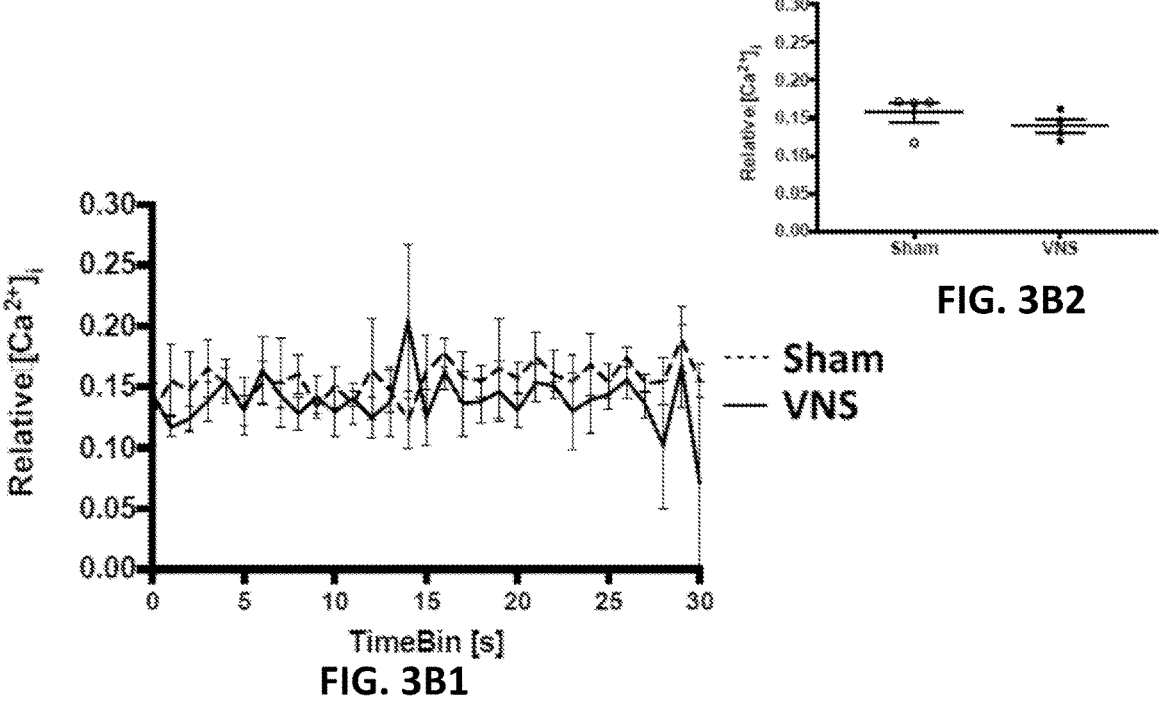
FIG. 3B2
FIG. 3B1

P-Selectin (CD62P)

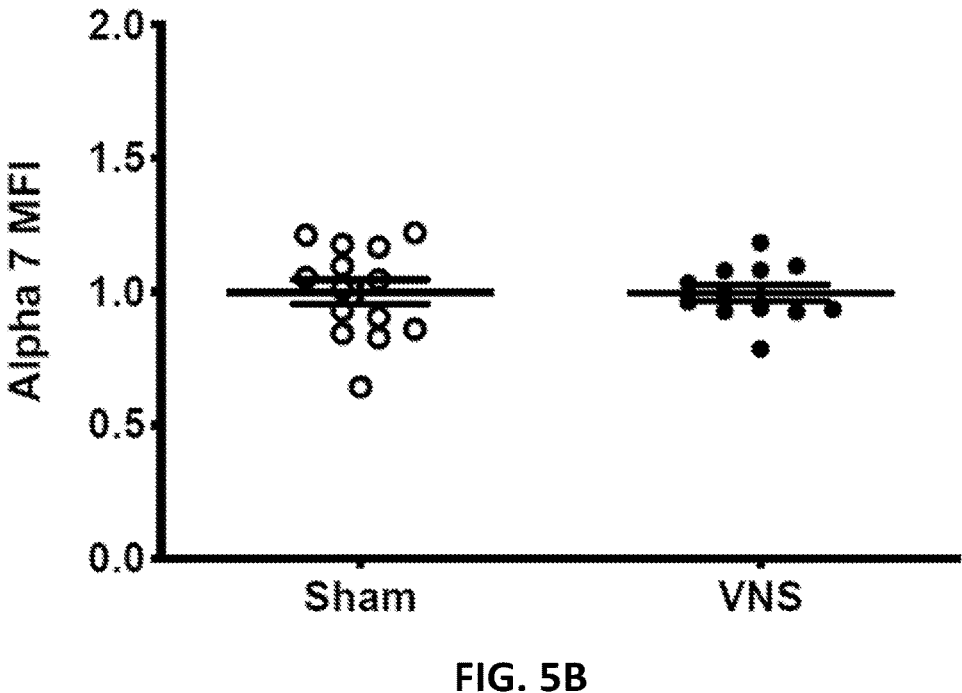
FIG. 5B
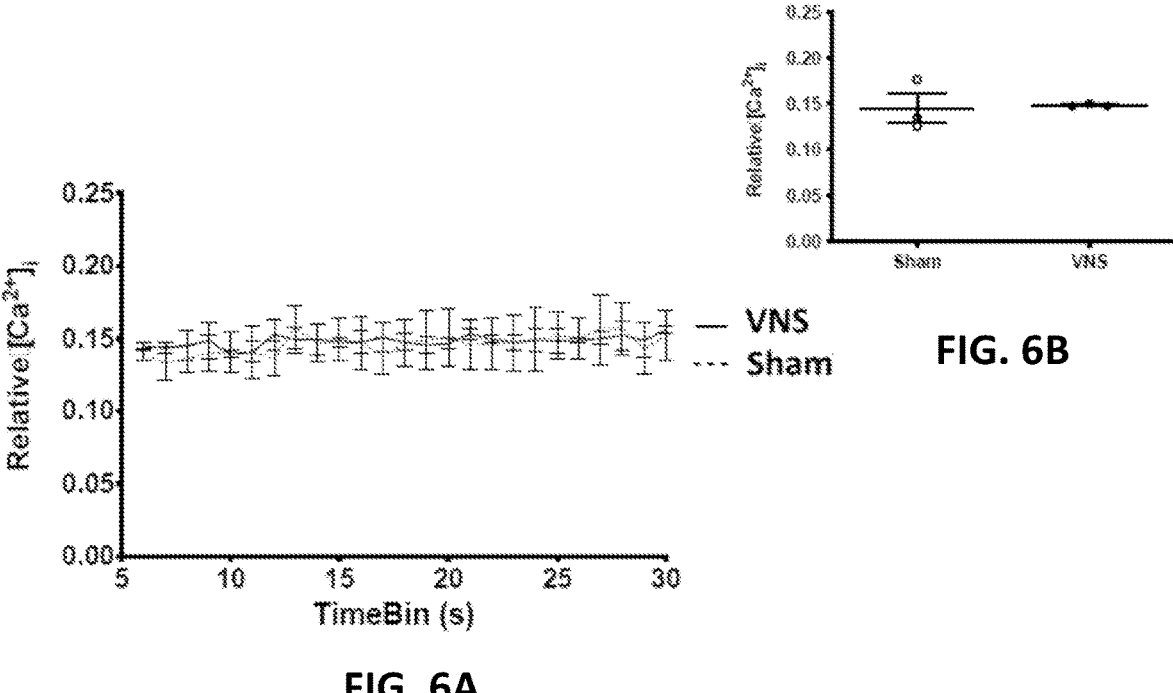
FIG. 6A
FIG. 6B

Spleen

METHODS FOR REDUCING BLEEDING IN HEMOPHILIA BY VAGUS NERVE STIMULATION TO PRIME PLATELETS

CLAIM OF PRIORITY

This patent application claims priority to U.S. Provisional Patent Application No. 63/395,775, titled "METHODS FOR REDUCING BLEEDING IN HEMOPHILIA BY VAGUS NERVE STIMULATION TO PRIME PLATELETS," filed on Aug. 5, 2022, herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Deficiency of coagulation factor VIII in hemophilia A disrupts clot formation and prolongs bleeding after injury. While the current mainstay of therapy is recurrent infusion of factor VIII concentrates, inhibitor antibodies often render these ineffective, mandating costly thrombotic therapies with higher morbidity and mortality. Preclinical evidence shows electrical vagus nerve stimulation accelerates clot formation and increases clot deposition to reduce traumatic bleeding.

SUMMARY OF THE DISCLOSURE

As described herein, vagus nerve stimulation augments clotting at the site of injury without precipitating systemic thrombosis, and may reduce traumatic bleeding in hemophilia A subjects. In both arterial hemorrhage and thrombosis models, we observed that vagus nerve stimulation bypasses the factor VIII deficiency of hemophilia A to decrease blood loss and accelerate clot formation. Vagus nerve stimulation targets acetylcholine-producing T lymphocytes in spleen and platelet alpha 7 nicotinic acetylcholine receptors (a7nAChR) to increase calcium uptake and enhance alpha granule release and surface expression of P-selectin. Splenectomy or genetic deletion of T cells or a7nAChR abolishes vagus nerve-mediated control of platelet calcium uptake and activation, thrombus formation, and bleeding time. These results reveal an endogenous vagus nerve pathway harnessing platelets to augment clot formation, which restores hemostasis in hemophilia A in lieu of clotting factor administration. Vagus nerve stimulation warrants clinical study as a potential therapy for coagulation disorders and surgical or traumatic bleeding.

In particular, vagus nerve stimulation may be applied as described herein to reduce traumatic bleeding in hemophilia A subjects that have not received a clotting factor. For example, subject's may have not received a clotting factor within at least the last 48 hours, the last 36 hours, the last 24 hours, the last 18 hours, the last 12 hours, the last 10 hours, the last 8 hours, the last 6 hours, the last 4 hours, or the last 2 hours. In the absence of an administered clotting factor, vagus nerve stimulation may work surprisingly well, even at relatively low stimulation "doses".

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIGS. 3A1 and 3A2 show vagus nerve stimulation requires α7nAChR to increase platelet cytosolic calcium, enhance cellular activation, and accelerate local clot formation. In FIG. 3A, C57BL6/J mice received vagus nerve stimulation or sham stimulation before harvesting circulating platelets to measure basal cytosolic calcium uptake. Data are presented as mean±s.e.m. (n=5-6 mice per group). , p<0.01 vs. sham. FIG. 3A2 shows a whisker plot of the data shown in FIG. 3A**.

FIG. 3B1, a7nAChR-deficient mice received vagus nerve stimulation or sham stimulation before harvesting circulating platelets to measure basal cytosolic calcium uptake. Data are presented as mean±s.e.m. (n=4 mice per group). p=NS vs. sham. FIG. 3B2 shows a whisker plot of the data shown in FIG. 3BA.

FIG. 5B, C57BL6/J mice received vagus nerve stimulation or sham stimulation before harvesting platelets to measure a7nAChR expression levels. Data are presented as mean±s.e.m. (n=12-14 mice per group). p=NS vs. sham.

FIGS. 6A and 6B show vagus nerve stimulation requires extracellular source to increase platelet calcium. C57BL6/J mice received vagus nerve stimulation or sham stimulation before harvesting circulating platelets to measure basal cytosolic calcium uptake in the absence of extracellular calcium. Data are presented as mean±s.e.m. (n=3 mice per group). p=NS vs. sham. FIG. 6B shows a whisker plot of the data shown in FIG. 6A.

FIG. 7A shows C57BL6/J mice received vagus nerve stimulation or sham stimulation before harvesting platelets for analysis of activated GPIIb/IIIa (JON/A) expression. Data are presented as mean±s.e.m. (n=13 mice per group). p=NS vs. sham. FIG. 7B shows C57BL6/J mice received vagus nerve stimulation or sham stimulation before harvesting platelets and analysis of phosphatidylserine. Data are presented as mean±s.e.m. (n=13-14 mice per group). p=NS vs. sham. FIG. 7C, C57BL6/J mice received vagus nerve stimulation or sham stimulation before harvesting platelets, ex vivo thrombin stimulation, and analysis of activated GPIIb/IIIa (JON/A) expression. Data are presented as mean±s.e.m. (n=9-10 mice per group). p=NS vs. sham. FIG. 7D, C57BL6/J mice received vagus nerve stimulation or sham stimulation before harvesting platelets, ex vivo thrombin stimulation, and analysis of phosphatidylserine expression. Data are presented as mean±s.e.m. (n=10-11 mice per group). p=NS vs. sham. FIG. 7E, C57BL6/J mice received vagus nerve stimulation or sham stimulation before harvesting platelets, ex vivo collagen stimulation, and analysis for P-selectin (CD62P) expression. Data are presented as mean±s.e.m. (n=7 mice per group). p=NS vs. sham. FIG. 7F, C57BL6/J mice received vagus nerve stimulation or sham stimulation before harvesting platelets, ex vivo ADP stimulation, and analysis for P-selectin (CD62P) expression. Data are presented as mean±s.e.m. (n=10-11 mice per group). p=NS vs. sham. FIG. 7G, C57BL6/J mice received vagus nerve stimulation or sham stimulation before harvesting platelets, ex vivo collagen stimulation, and analysis of activated GPIIb/IIIa (JON/A) expression. Data are presented as mean±s.e.m. (n=8-11 mice per group). p=NS vs. sham. FIG. 7H, C57BL6/J mice received vagus nerve stimulation or sham stimulation before harvesting platelets, ex vivo collagen stimulation, and analysis of phosphatidylserine expression. Data are presented as mean±s.e.m. (n=8 mice per group). p=NS vs. sham. FIG. 7I, C57BL6/J mice received vagus nerve stimulation or sham stimulation before harvesting platelets, ex vivo ADP stimulation, and analysis of activated GPIIb/IIIa (JON/A) expression. Data are presented as mean±s.e.m. (n=10 mice per group). p=NS vs. sham. FIG. 7J, C57BL6/J mice received vagus nerve stimulation or sham stimulation before harvesting platelets, ex vivo ADP stimulation, and analysis of phosphatidylserine expression. Data are presented as mean±s.e.m. (n=7 mice per group). p=NS vs. sham.

FIG. 8A, C57BL6/J mice underwent baseline heart rate measurement before and five minutes after vagus nerve stimulation. Data are presented as mean±s.e.m. Pre-VNS (n=6) and Post-VNS (n=6) mice per group. p=0.15 vs. baseline. Statistical significance was determined by unpaired two-tailed Student's t-test. Figure represents pooled results from 2 experiments performed independently. FIG. 8B, C57BL6/J mice underwent baseline mean arterial blood pressure measurement before and five minutes after vagus nerve stimulation. Data are presented as mean±s.e.m. Pre-VNS (n=6) and Post-VNS (n=6) mice per group. p=0.73 vs. baseline. Statistical significance was determined by unpaired two-tailed Student's t-test. Figure represents pooled results from 2 experiments performed independently. FIG. 8C, α7nAChR-deficient (α7K0) mice underwent baseline heart rate measurement before and five minutes after vagus nerve stimulation. Data are presented as mean±s.e.m. Pre-VNS (n=5) and Post-VNS (n=4) mice per group. p=0.77 vs. baseline. Statistical significance was determined by unpaired two-tailed Student's t-test. Figure represents pooled results from 2 experiments performed independently. FIG. 8D, α7nAChR-deficient (α7K0) mice underwent baseline mean arterial blood pressure measurement before and five minutes after vagus nerve stimulation. Data are presented as mean±s.e.m. Pre-VNS (n=5) and Post-VNS (n=4) mice per group. p=0.46 vs. baseline. Statistical significance was determined by unpaired two-tailed Student's t-test. Figure represents pooled results from 2 experiments performed independently. FIG. 8E, Athymic nude (Foxn1nu) mice underwent baseline heart rate measurement before and five minutes after vagus nerve stimulation. Data are presented as mean±s.e.m. Pre-VNS (n=4) and Post-VNS (n=4) mice per group. p=0.44 vs. baseline. Statistical significance was determined by unpaired two-tailed Student's t-test. Figure represents pooled results from 2 experiments performed independently. FIG. 8F, athymic nude (Foxn1nu) mice underwent baseline mean arterial blood pressure measurement before and five minutes after vagus nerve stimulation. Data are presented as mean±s.e.m. Pre-VNS (n=4) and Post-VNS (n=4) mice per group. p=0.85 vs. baseline. Statistical significance was determined by unpaired two-tailed Student's t-test. Figure represents pooled results from 2 experiments performed independently.

FIG. 9A, Preliminary FSC/SSC gates for starting platelet cell population from murine systemic whole blood. FIG. 9B, Platelet cell population identification with anti-CD41a.

FIG. 10 depicts the percent of total leukocytes that express CD41$^+$/CD4$^+$ in spleen. FIG. 7 depicts the percent of total leukocytes that express CD41$^+$/CD4$^+$ in blood. These results indicate that platelets and CD4$^+$ cells are in contact with each other. Additionally, immunohistochemistry was performed on ChAT-TdTomato mouse spleens to show the relationship of CD4$^+$ ChAT$^+$T lymphocytes with circulating platelets and confocal microscopic images are presented in FIGS. 2d and 2e of Bravo-Iniguez et al. Nat Commun (2023) 14:3122, herein incorporated by reference. FIG. 2d of Bravo-Iniguez et al is a representative confocal microscopy image of spleen from ChAT-TdTomato mouse with immunostaining of CD41+ platelets (green), CD4+ T lymphocytes (purple), and ChAT-eGFP+ T lymphocytes (red) throughout spleen but mostly in the peripheral white pulp (arrows). FIG.

2e Bravo-Iniguez et al is a representative merged confocal microscopy image of spleen from ChAT-TdTomato mouse showing CD4$^+$ ChAT-eGFP$^+$ T lymphocyte (red and pink, center) in direct contact with CD41$^+$ platelets (green). Together these results support the conclusion that vagus nerve stimulation stimulates T cells to release acetylcholine and signal platelets via platelet alpha 7 nicotinic acetylcholine receptors (α7nAChR).

DETAILED DESCRIPTION

Primary hemostasis after blood vessel injury induces local vasoconstriction and recruitment of circulating platelets to form an initial platelet plug. Secondary hemostasis occurs on the surface of platelets where the tissue factor and contact activation pathways generate thrombin (coagulation factor II), which converts soluble fibrin into insoluble fibrin to stabilize the developing clot. Hemophilia A results from a congenital or acquired impairment in coagulation factor VIII activity, most often caused by genetic mutations that reduce or eliminate factor VIII production. Patients with hemophilia generate insufficient quantities of thrombin and fibrin, resulting in clot instability. The clinical hallmarks are hemorrhage after injury and spontaneous bleeding into muscles and joints. Because the incidence of bleeding complications correlates with circulating factor VIII levels, traditional and current therapies are based on replacing factor VIII through exogenous infusions. Administration of recombinant factor VIII concentrate mitigates transmission of hepatitis or human immunodeficiency virus. However, more than 30% of children with severe hemophilia A cease responding to therapy because they develop neutralizing (inhibitor) factor VIII antibodies. Treatment then shifts to prothrombin complex concentrates or recombinant factor VIIa to bypass factor VIII, but these alternative thrombotic agents are very expensive and associated with significant morbidity and mortality.

Figure 1A:
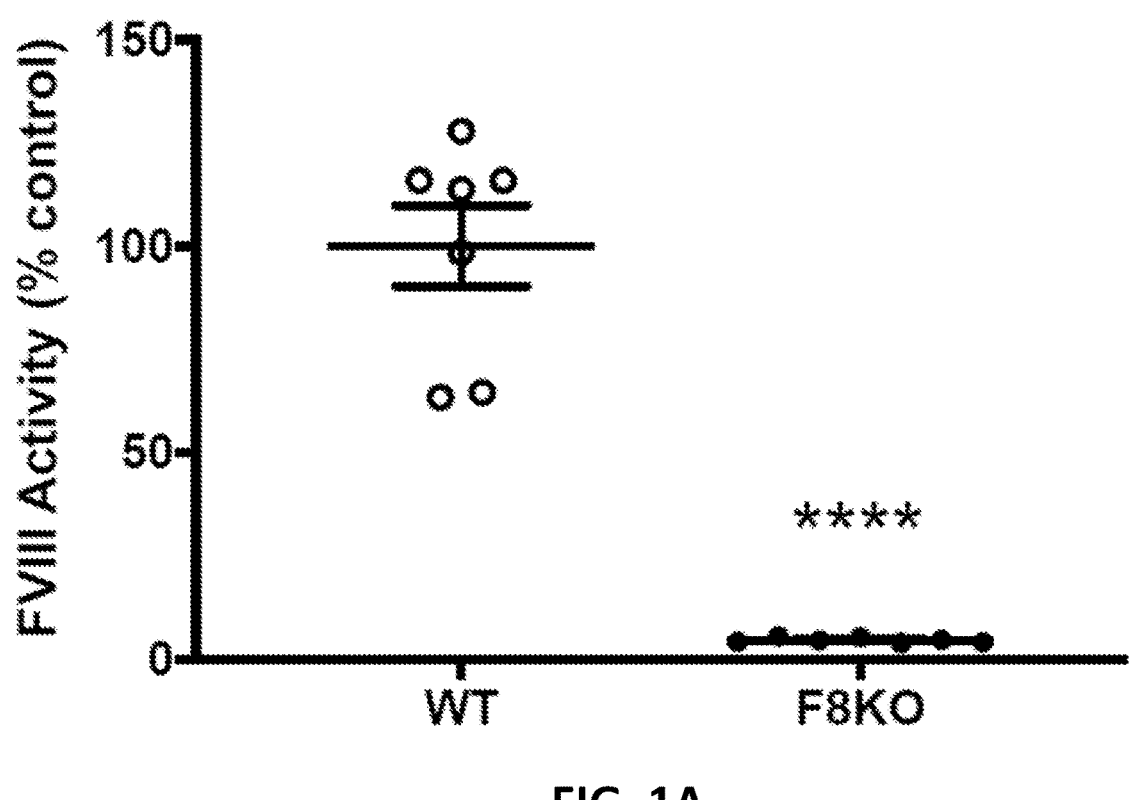
FIG. 1A shows vagus nerve stimulation reduces traumatic blood loss in hemophilia A mice. a, Circulating factor VIII activity in wild-type and factor VIII deficient (hemophilia A) mice. Data are presented as mean±s.e.m. (n=7 mice). ****, p<0.0001 vs. control.
Figure 1B:
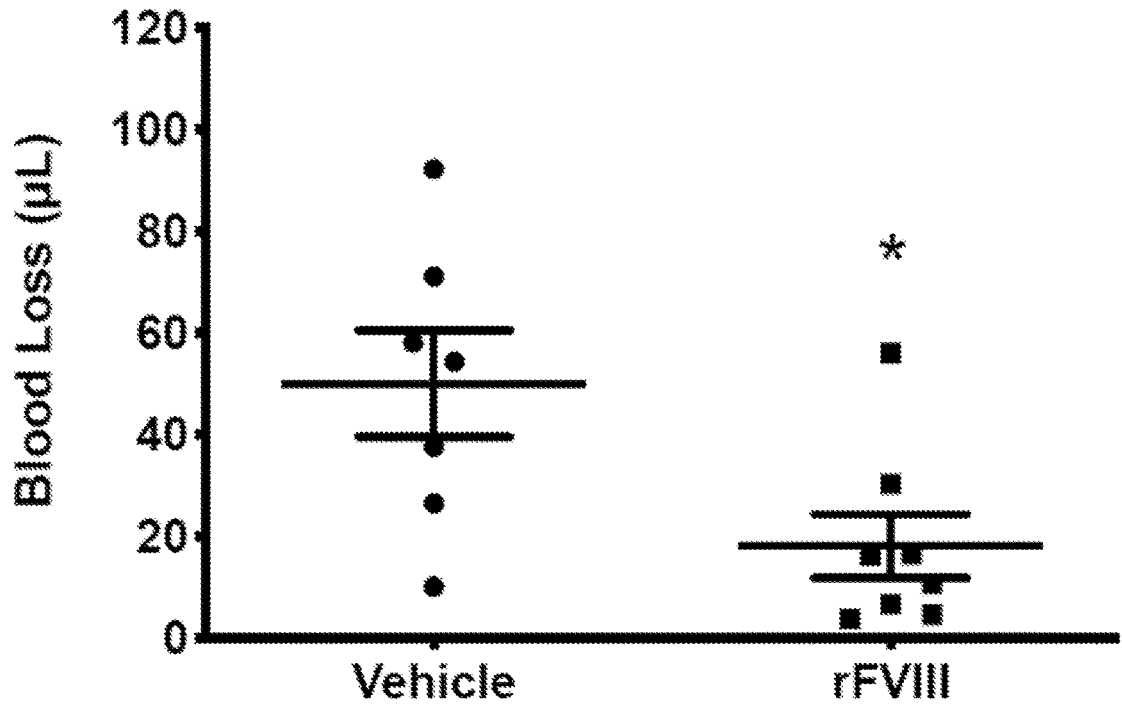
FIG. 1B shows Hemophilia A mice received rFVIII (Advate®, 200 U/kg, r.o.) or vehicle before tail transection. Data are presented as mean±s.e.m. (n=7-8 mice per group). *, p<0.05 vs. sham.
Figure 1C:
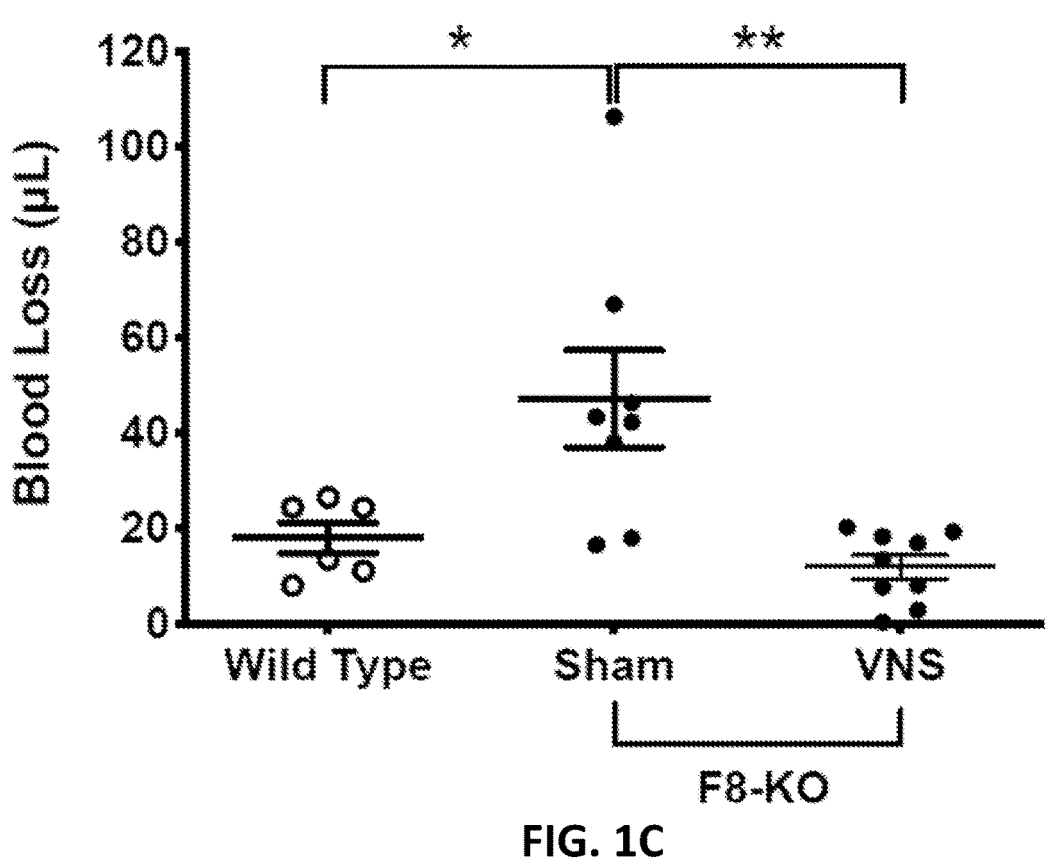
FIG. 1C, Hemophilia A mice received vagus nerve stimulation or sham stimulation before tail transection. Data are presented as mean±s.e.m. (n=6-9 mice per group). *, p<0.05 vs. wild type. **, p<0.01 vs. sham.
Figure 1D:
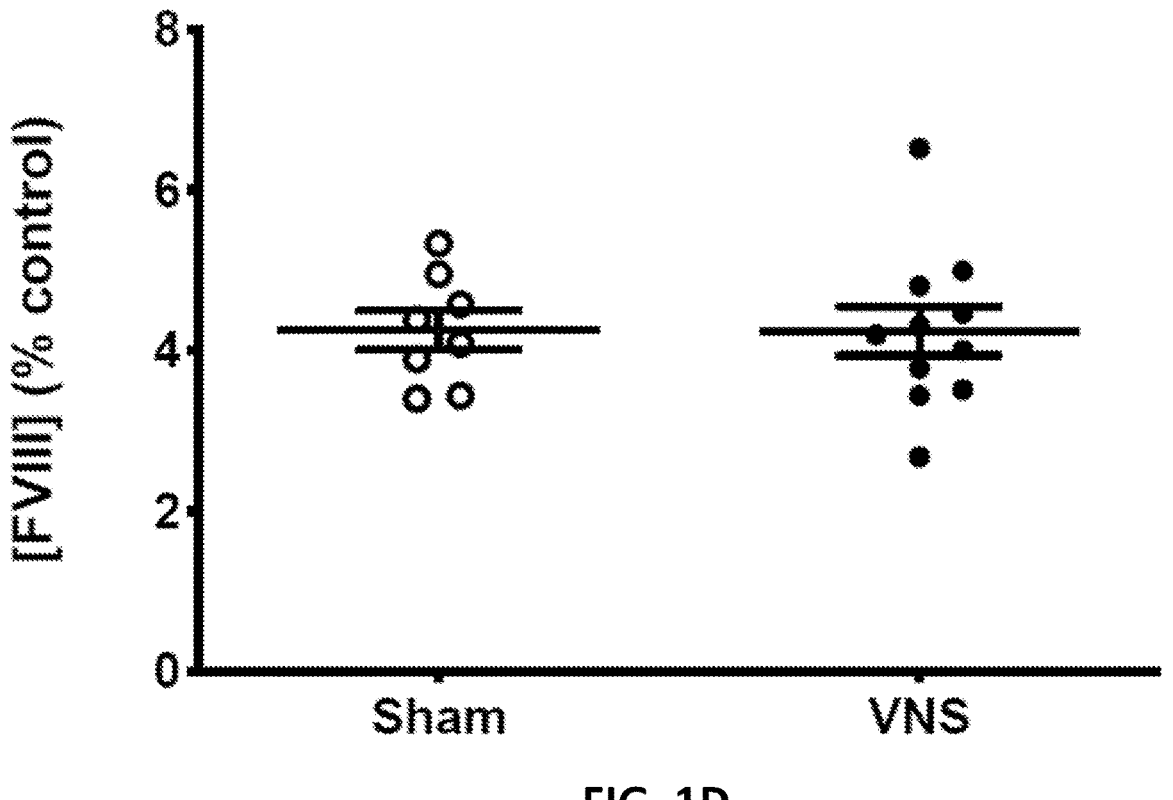
FIG. 1D, Hemophilia A mice received vagus nerve stimulation or sham stimulation before blood collection to determine factor VIII activity. Data are presented as mean±s.e.m. (n=8-11 mice per group). p=NS vs. sham.
Figure 1E:
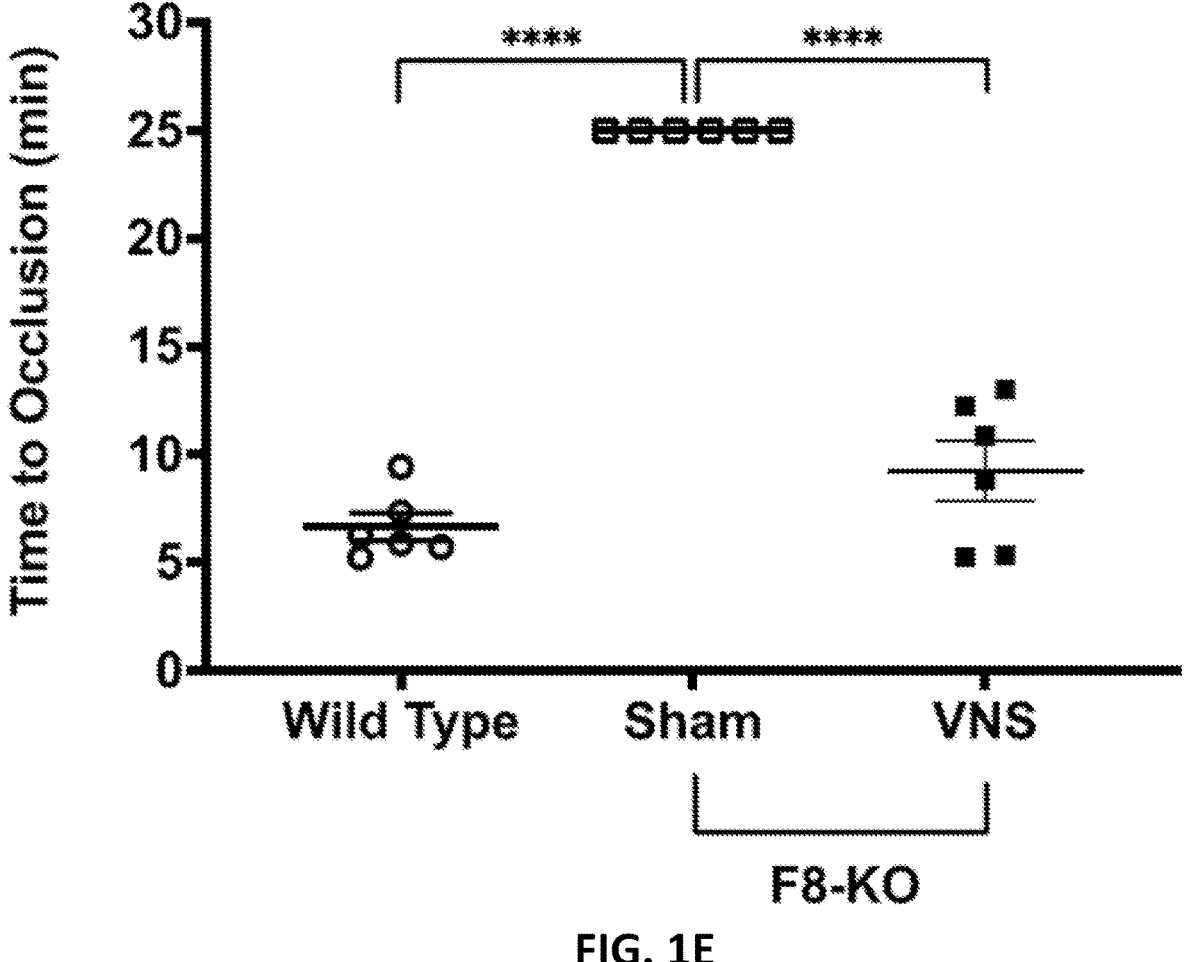
FIG. 1E, Hemophilia A mice received vagus nerve stimulation or sham stimulation before carotid artery injury. Data are presented as mean±s.e.m. (n=6 mice per group). **, p<0.0001 vs. wt. **, p<0.0001 vs. sham.

The autonomic nervous system regulates tissue perfusion and hemostasis. Norepinephrine release from perivascular sympathetic neurons mediates arteriolar vasoconstriction to decrease blood flow and facilitate clot formation after injury. Preganglionic sympathetic neurons stimulate the adrenal medulla to secrete epinephrine that activates circulating platelets, the body's primary effector cells to support clotting. Parasympathetic activation mediated by the vagus nerve can support clot formation following traumatic hemorrhage by slowing heart rate to reduce blood pressure. Preclinical evidence shows that electrical vagus nerve stimulation significantly reduces blood loss and duration of bleeding after soft tissue injury. Vagus nerve stimulation accelerates clot initiation as measured by rotational thromboelastography (RoTEG), a viscoelastic technique to quantify interactions of plasma coagulation factors and inhibitors with blood cells. Vagus nerve stimulation increases early thrombin generation at the injury site without significantly changing circulating thrombin levels. Accordingly, here we reasoned vagus nerve stimulation might enhance clot formation and reduce bleeding in hemophilia A. To study vagus nerve stimulation in hemophilia A, we utilized factor VIII-knockout (F8KO) mice derived via targeted mutation of the factor VIII gene resulting in defective protein production. To validate the bleeding model, we measured circulating factor VIII activity in F8KO mice and found it is significantly reduced compared with wild-type control animals (FIG. 1a). We then administered recombinant factor VIII, a clinical hemophilia A therapy, to F8KO mice before tail transection causing uncontrolled arterial hemorrhage, and recorded a significant 64% reduction in blood loss as compared with vehicle treatment (FIG. 1b). After administering five minutes of vagus nerve stimulation to the F8KO mice, we observed a significant 75% reduction in blood loss as compared with sham stimulation (FIG. 1c). Because the vagus nerve innervates liver which produces factor VIII, we wondered if vagus nerve stimulation stimulates factor VIII synthesis. Our results show vagus nerve stimulation does not increase systemic factor VIII activity as compared with sham stimulation (FIG. 1d). To confirm vagus nerve stimulation accelerates clotting, we utilized a carotid artery endothelial injury model that quantifies platelet activation and thrombus formation. We observed that vagus nerve stimulation in F8KO mice significantly reduces time to carotid occlusion after injury as compared with sham stimulation. By analyzing lung sections for signs of systemic hypercoagulability after vagus nerve stimulation, we observed normal tissue architecture without evidence of arterial clots, alveolar congestion or hemorrhage associated with thromboembolism (FIG. 1E). Together these findings show vagus nerve stimulation reduces blood loss and accelerates clot formation in hemophilia A mice without increasing circulating factor VIII activity or inducing pulmonary thrombosis.

Figures 2A, 2B:
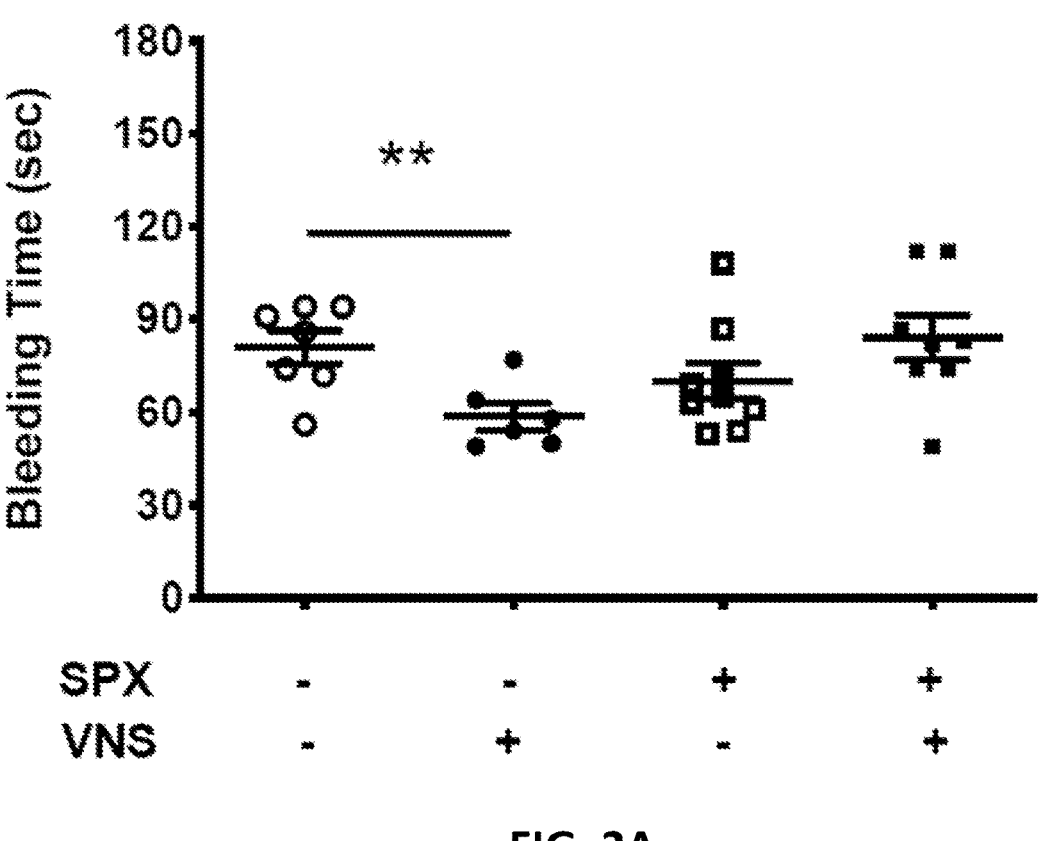
FIG. 2A shows vagus nerve stimulation harnesses choline acetyltransferase-expressing T cells in spleen to stimulate platelets via a7nAChR. a, C57BL6/J mice underwent splenectomy or sham splenectomy followed by vagus nerve stimulation or sham stimulation before tail transection. Data are presented as mean±s.e.m. (n=6-9 mice per group). **, p<0.01 versus sham.
FIG. 2B, Wild-type BALB/c or T lymphocyte deficient (Foxn1nu) mice received vagus nerve stimulation or sham stimulation before tail transection. Data are presented as mean±s.e.m. (n=4-6 mice per group). *, p=0.05 vs. sham.

Previous studies demonstrate vagus nerve stimulation inhibits neutrophil migration to sites of peripheral inflammation and decreases expression of CD11b, a beta(2)-integrin important to cellular adhesion and chemotaxis, but only in the presence of an intact spleen. Because the mouse tail is not innervated by the vagus nerve, we reasoned vagus nerve stimulation facilitates local thrombosis to reduce bleeding by influencing circulating platelets in spleen. Accordingly, we performed splenectomy before tail transection. While we did not observe a difference in bleeding times between splenectomized animals and sham-splenectomized controls, vagus nerve stimulation fails to decrease bleeding time in splenectomized mice as compared with sham stimulation (FIG. 2a).

Figure 2C:
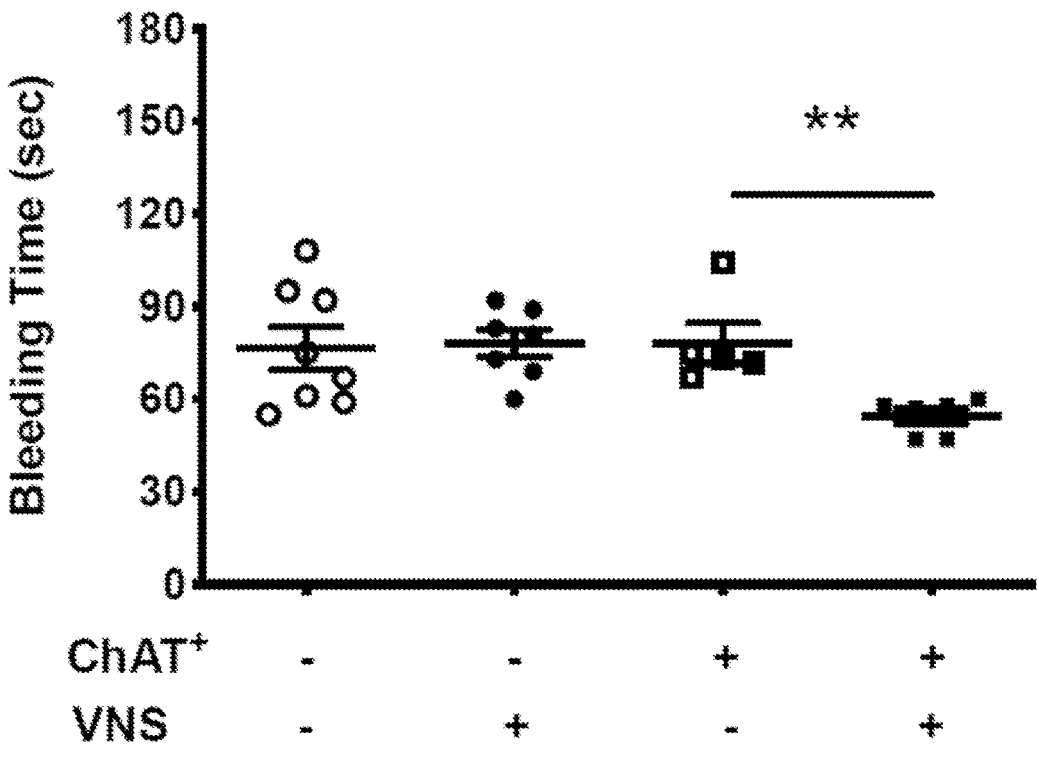
FIG. 2C, T lymphocyte deficient (Foxn1nu) mice were reconstituted with ChAT-eGFP+ or ChAT-eGFP– cells followed by vagus nerve stimulation or sham stimulation before tail transection. Data are presented as mean±s.e.m. (n=5-8 mice per group). **, p<0.01 vs. sham.

Prior evidence establishes that vagus nerve stimulation induces a distinct subset of memory T cells (CD4+ CD44high CD62low ChAT-EGFP+) expressing choline acetyltransferase, the enzyme that catalyzes acetylcholine synthesis, to increase acetylcholine levels in spleen and inhibit cytokine production by local tissue macrophages. To determine the role of ChAT-EGFP+ T lymphocytes in hemostasis, we first performed tail transections in athymic nude (Foxn1nu) mice lacking mature functional lymphocytes. We did not observe a difference in bleeding time between Foxn1nu mice and wild-type mice (FIG. 2b). Vagus nerve stimulation fails to decrease bleeding time in Foxn1nu mice as compared with sham stimulation (FIG. 2b). We then isolated ChAT-EGFP+ or control ChAT-EGFP− splenic cells from ChAT(BAC)-EGFP mice and transferred them into Foxn1nu mice before tail injury. Vagus nerve stimulation significantly reduces bleeding time in Foxn1nu mice reconstituted with ChAT-EGFP+ T lymphocytes, but fails to shorten bleeding time in animals given ChAT-EGFP− T cells (FIG. 2c). Collectively these findings indicate vagus nerve stimulation reduces bleeding time through a mechanism that requires splenic ChAT-EGFP+ T lymphocytes.

Figure 2D:
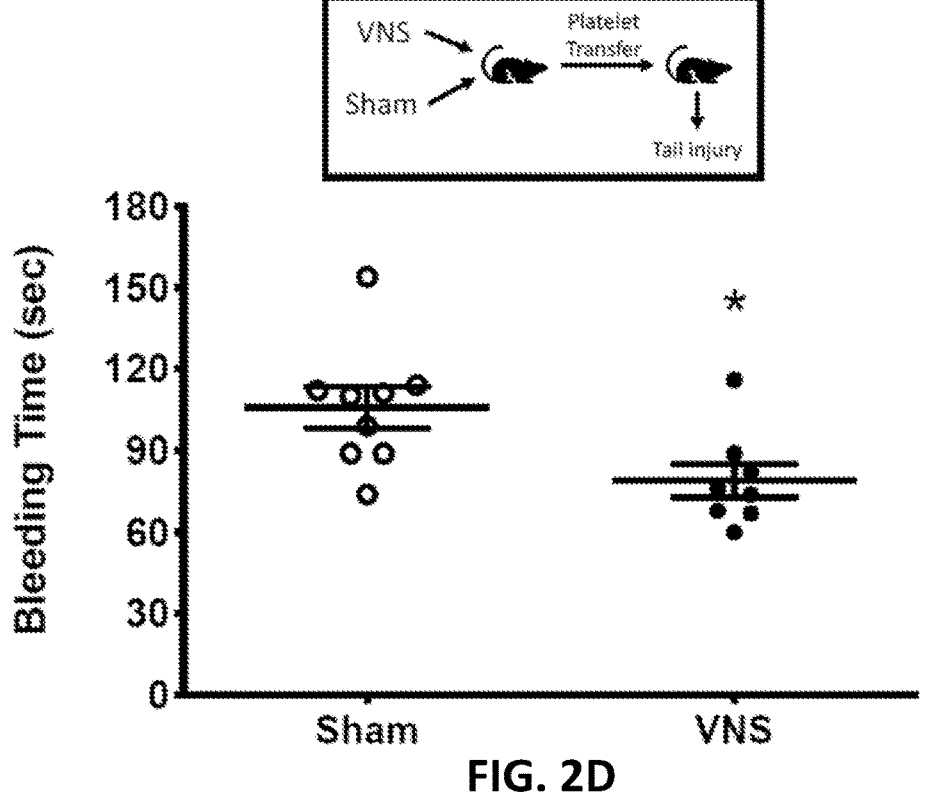
FIG. 2D, Platelets from uninjured C57BL6/J mice receiving vagus nerve stimulation or sham stimulation were transferred into naïve animals before tail transection. Data are presented as mean±s.e.m. (n=8-9 mice per group). *, p<0.05 vs. sham.
Figure 2E:
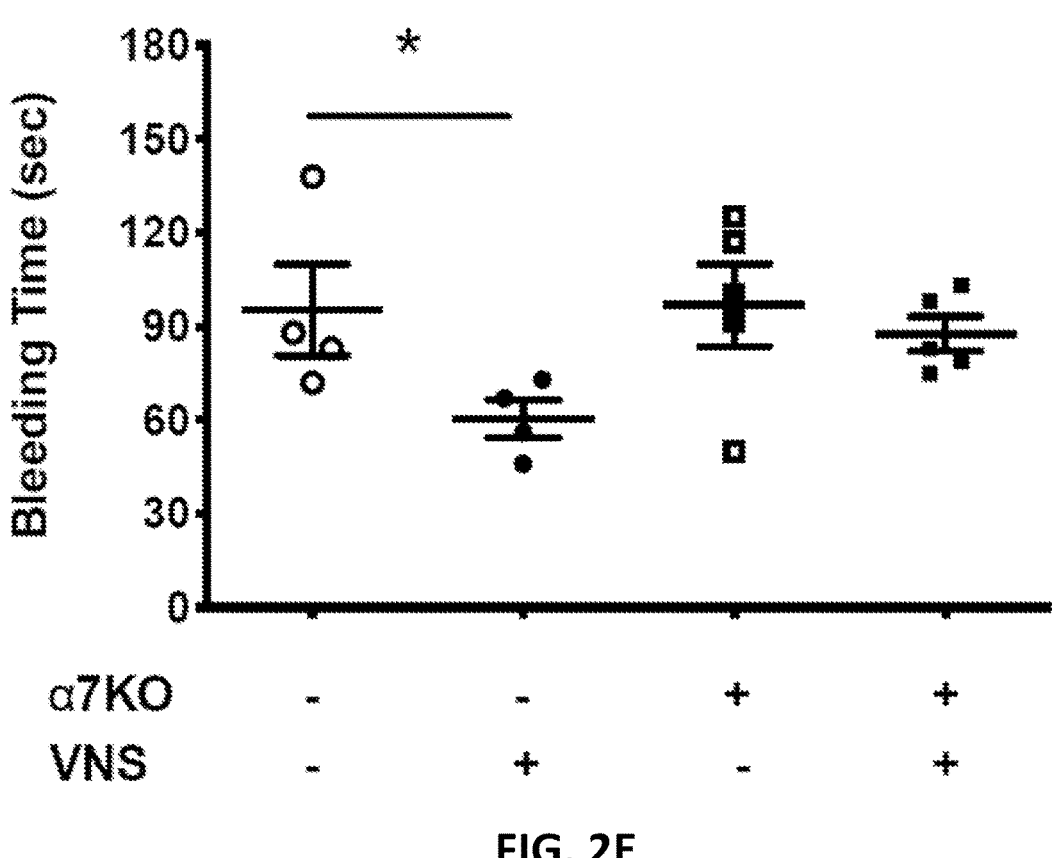
FIG. 2E, Wild-type or a7nAChR-deficient mice received vagus nerve stimulation or sham stimulation before tail transection. Data are presented as mean±s.e.m. (n=4-5 mice per group). *, p<0.05 vs. sham.
Figure 2F:
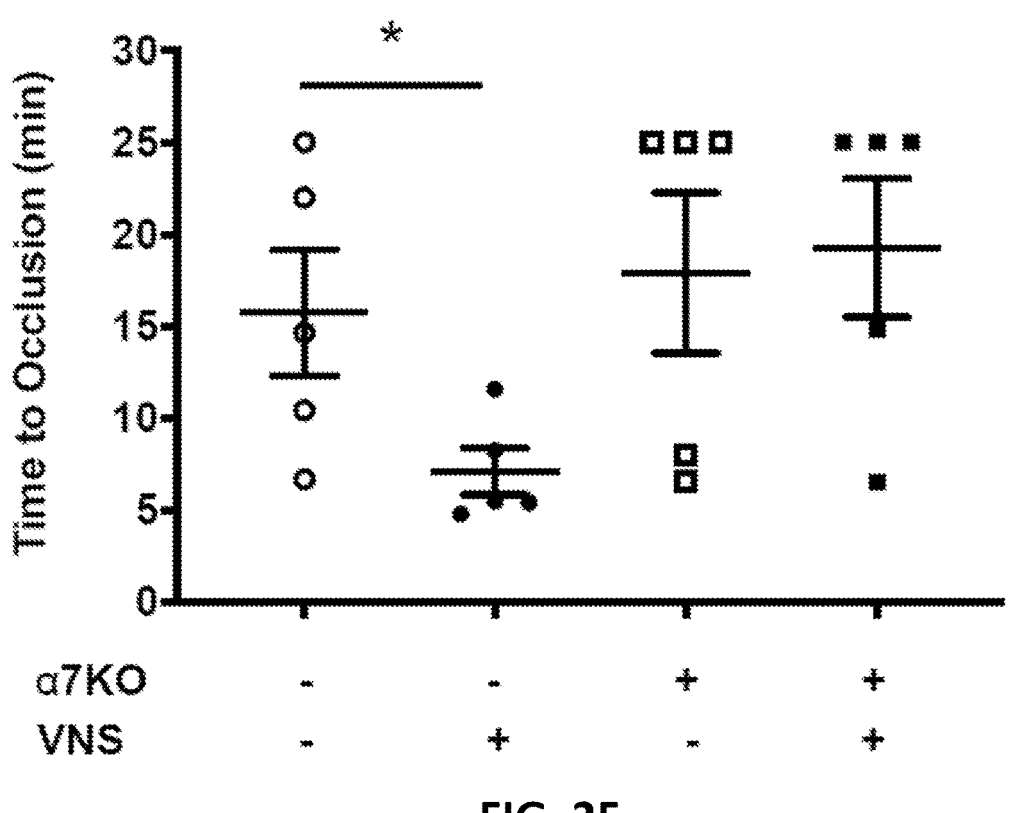
FIG. 2F, Wild-type or a7nAChR-deficient mice received vagus nerve stimulation or sham stimulation before carotid artery injury. Data are presented as mean±s.e.m. (n=5 mice per group). *, p<0.05 vs. sham.

Acetylcholine and other cholinergic agonists enhance human platelet activation via a7 nicotinic acetylcholine receptors (a7nAChR). Considering one-third of circulating platelets reside in spleen, we reasoned splenic ChAT-EGFP+ T-cell acetylcholine secretion controls platelet a7nAChR function. To explore this, we performed vagus nerve stimulation on uninjured wild-type mice and transferred circulating platelets into naïve animals undergoing tail transection. Platelets from vagus nerve stimulated mice significantly reduce bleeding time in recipient animals as compared with platelets from sham-stimulated mice (FIG. 2D). We performed complete blood counts on the donor mice to determine if platelet number changes after vagus nerve stimulation. There is no significant difference in platelet count or other circulating blood cell counts after vagus nerve stimulation as compared with sham stimulation (Table 1). Next, we studied hemostasis in a7nAChR-deficient (a7KO) mice. We did not observe a difference in bleeding time between a7KO and wild-type littermate mice (FIG. 2E). Vagus nerve stimulation significantly reduces tail bleeding time in wild-type mice as compared with sham stimulation, but fails to reduce bleeding time in a7KO mice (FIG. 2E). After carotid artery injury, we did not observe a difference in occlusion time between a7KO and wild-type mice (FIG. 2F). Vagus nerve stimulation significantly reduces time to carotid occlusion in wild-type animals as compared with sham stimulation, but fails to decrease occlusion time in a7KO mice (FIG. 2F). Together these findings suggest vagus nerve stimulation accelerates local thrombosis to decrease bleeding through a mechanism requiring a7nAChR.

Figure 2G:
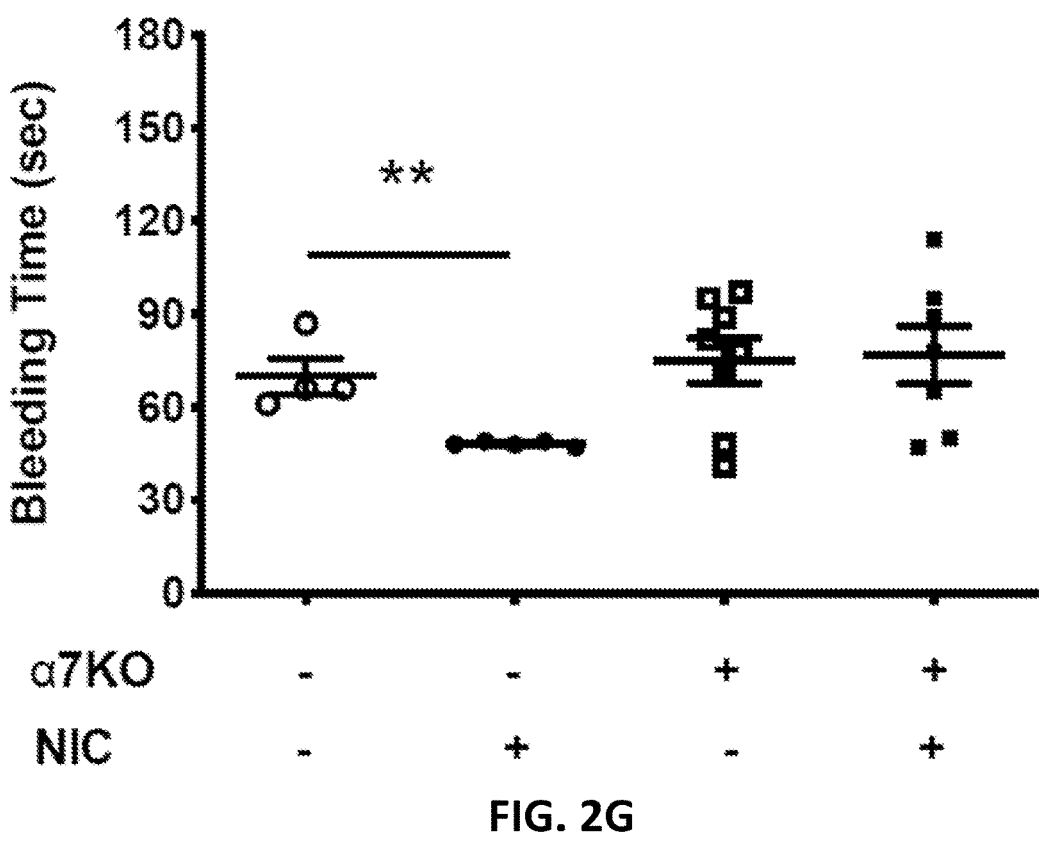
FIG. 2G, Wild-type or a7nAChR-deficient mice received nicotine or vehicle before tail transection. Data are presented as mean±s.e.m. (n=4-8 mice per group). **, p<0.01 vs. vehicle control.
Figure 2H:
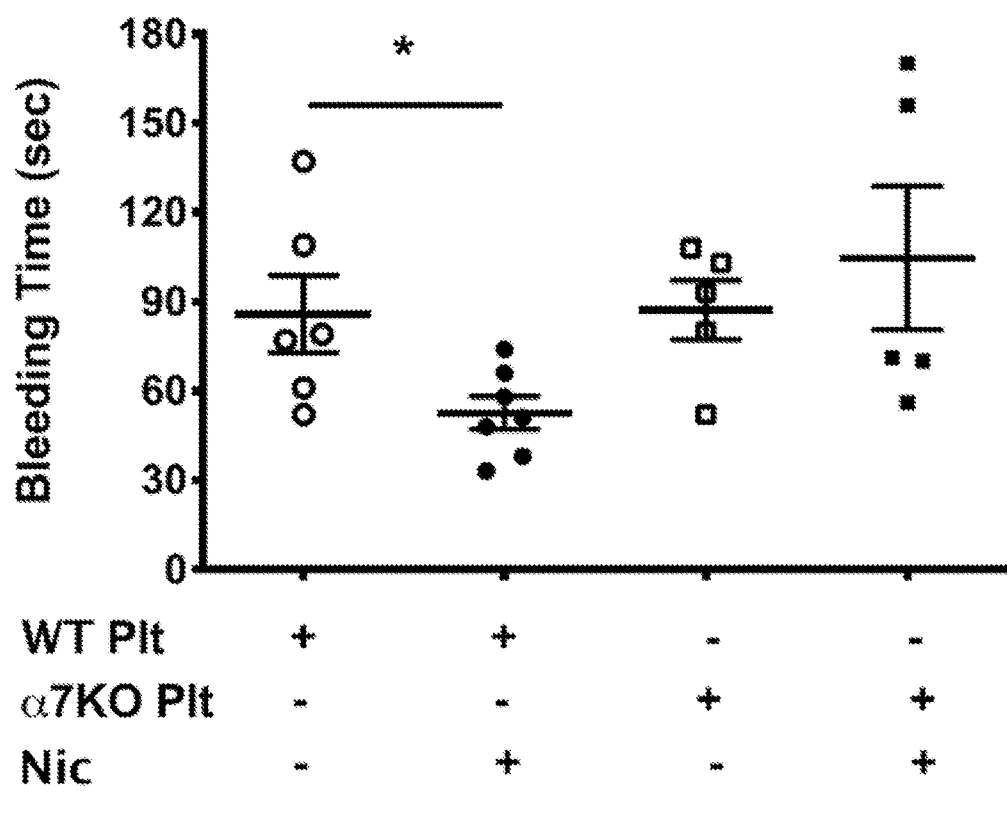
FIG. 2H, a7nAChR deficient mice were reconstituted with platelets from wild-type or a7nAChR-deficient mice followed by treatment with nicotine or vehicle before tail transection. Data are presented as mean±s.e.m. (n=5-7 mice per group). *, p<0.05 vs. vehicle control.
Figure 5A:
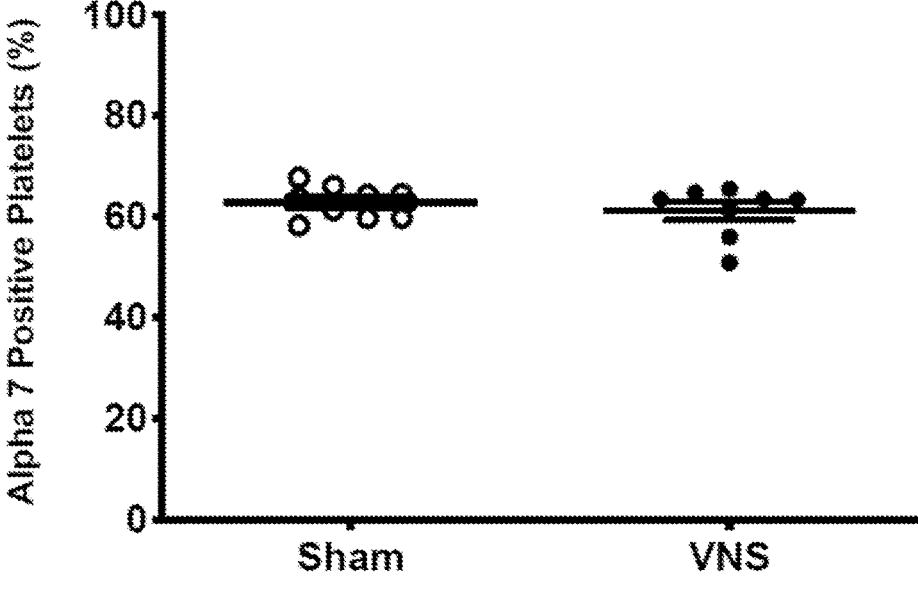
FIG. 5A Effect of vagus nerve stimulation on platelet a7nAChR expression. a, C57BL6/J mice received vagus nerve stimulation or sham stimulation before harvesting circulating platelets to measure percent expression of a7nAChR. Data are presented as mean±s.e.m. (n=8-9 mice per group). p=NS vs. sham.
Figure 7A:
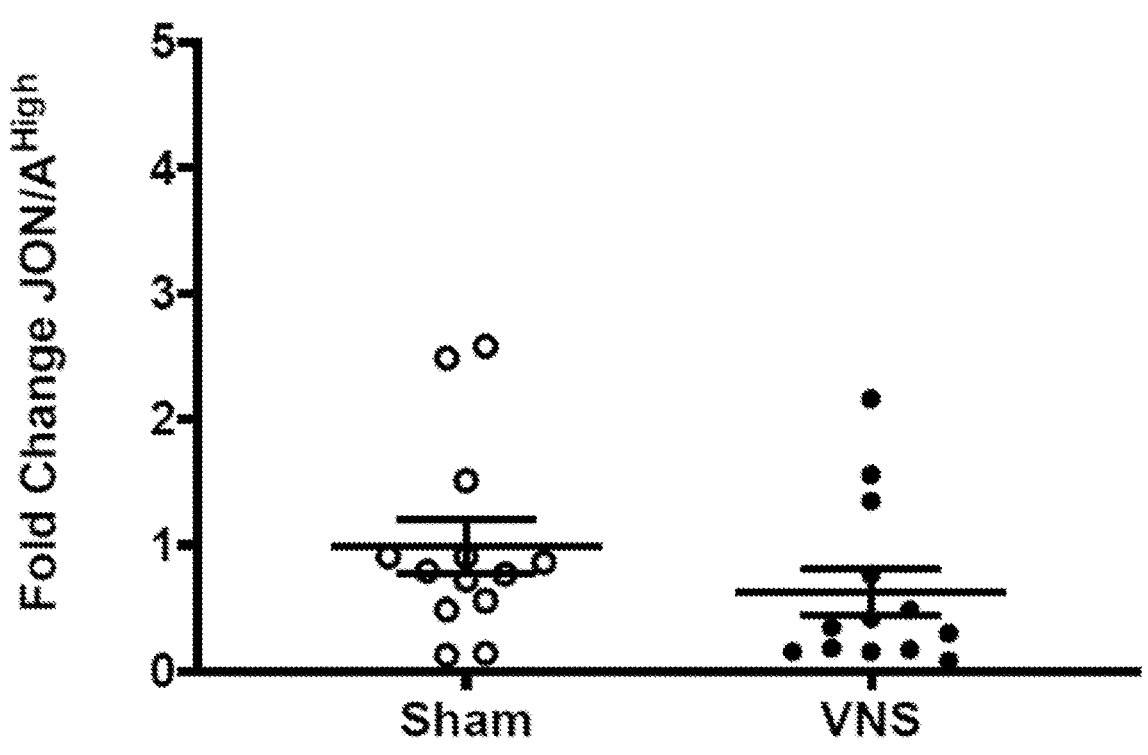
FIGS. 7A-7J show vagus nerve stimulation does not change platelet activated GPIIb/IIIa or phosphatidylserine expression.

To confirm platelet a7nAChR modulates hemostasis, we first administered the pharmacological a7nAChR agonist nicotine to wild-type mice before tail injury. Nicotine significantly decreases bleeding time as compared with vehicle treatment (FIG. 2G). Similar to vagus nerve stimulation, nicotine fails to reduce bleeding time in a7nAChR-deficient mice (FIG. 2G). To restrict a7nAChR to platelets, we transferred platelets from wild-type or a7KO donor mice into a7nAChR-deficient animals before tail transection. Nicotine significantly reduces bleeding time in a7 a7nAChR-deficient mice reconstituted with wild-type platelets, but not in animals receiving platelets from a7KO donors (FIG. 2H). To evaluate platelet a7nAChR function, FACS analysis reveals similar percentages of platelets expressing a7nAChR after vagus nerve stimulation or sham stimulation (FIG. 5A). We did not observe significant differences in a7nAChR expression levels on platelets after vagus nerve stimulation as compared with sham stimulation (FIG. 5B). Previous in vitro experiments demonstrate a7nAChR modulates platelet calcium uptake and intracellular calcium governs essential platelet activation pathways. By quantifying platelet cytosolic calcium levels, we found vagus nerve stimulation significantly increases basal intracellular calcium concentrations as compared with sham stimulation (FIG. 7A). Vagus nerve stimulation fails to increase platelet cytosolic calcium in a7nAChR-deficient mice (FIG. 5B), or when the extracellular calcium ion source is removed (FIG. 6A). Collectively these findings suggest vagus nerve stimulation harnesses acetylcholine release from ChAT-EGFP+ T cells to increase platelet cytosolic calcium via a7nAChR.

Figure 7B:
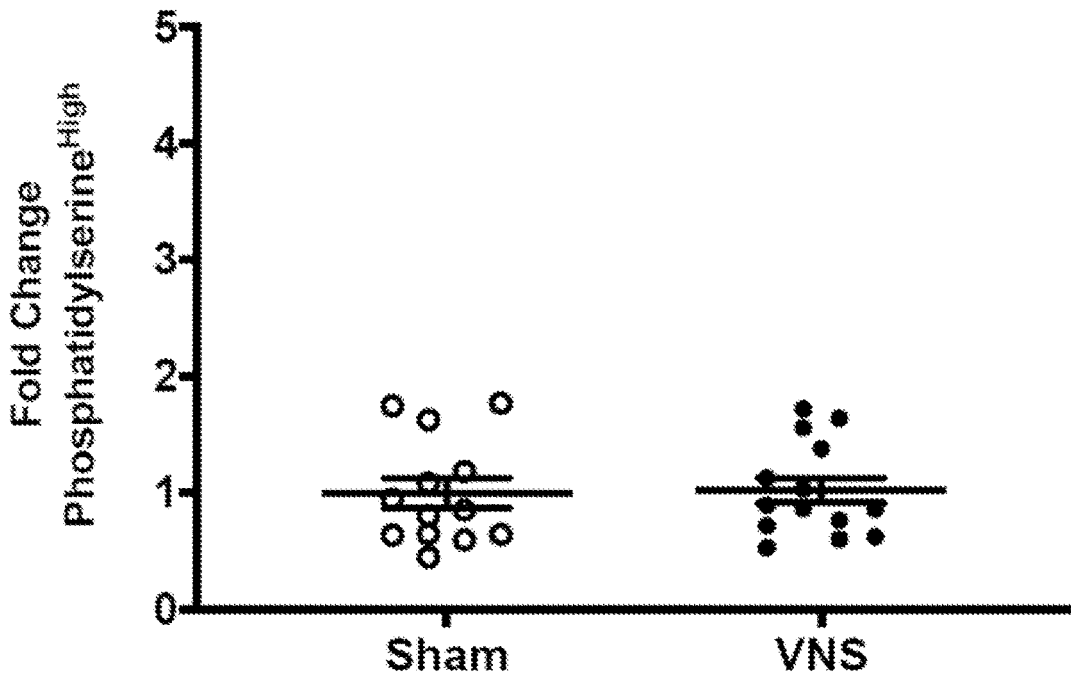
Figure 7C:
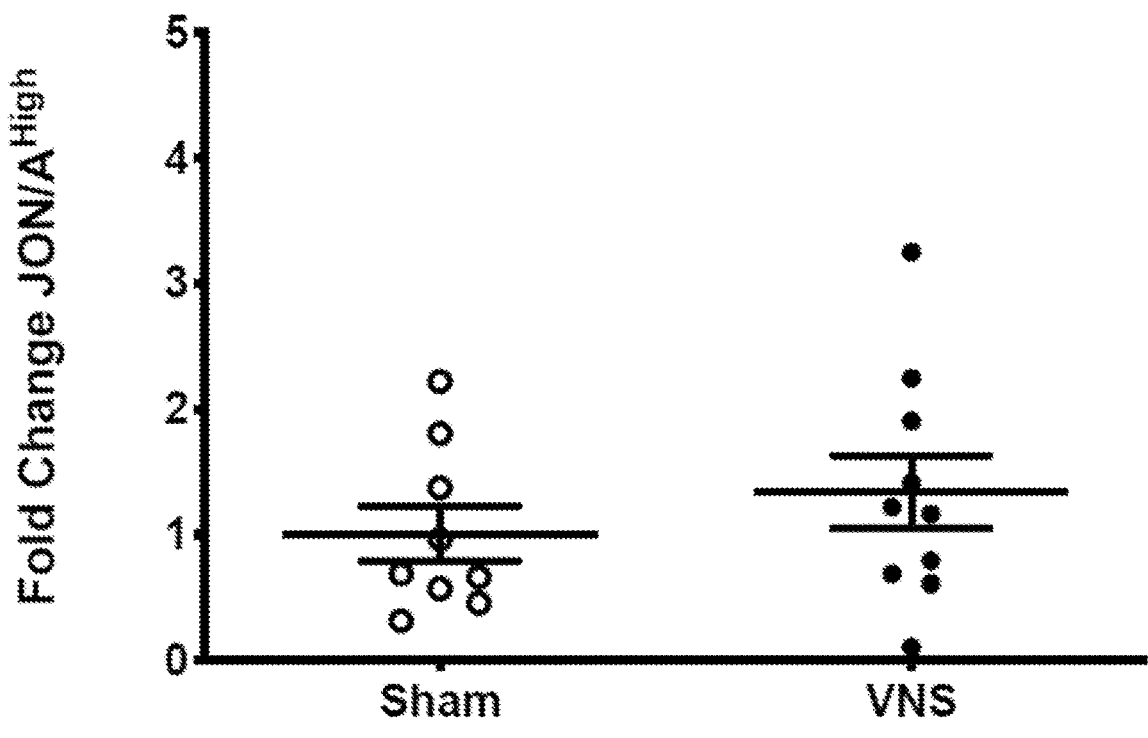
Figure 7D:
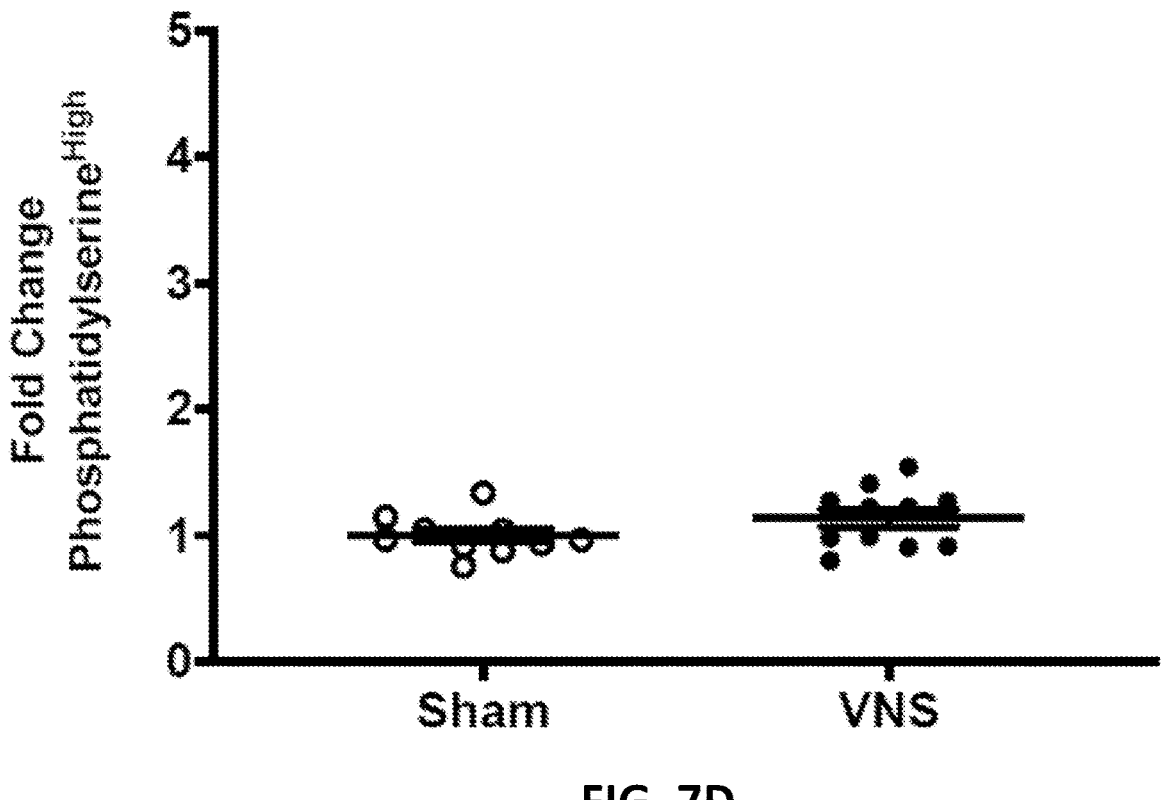

Platelet activation at an injury site is characterized by fusion of intracellular alpha granules with the plasma membrane to release prothrombotic proteins including P-selectin, conformational change to the active primary fibrinogen receptor GPIIb/IIIa that facilitates cross-linking and aggregation, and increased expression of membrane phosphatidylserine that promotes prothrombinase complex formation and clot formation. To explore these cellular activation events, we first analyzed circulating platelets from healthy uninjured mice administered vagus nerve stimulation. Compared with sham stimulation, platelets remain quiescent after vagus nerve stimulation without increased expression of P-selectin (FIGS. 7C and 7D, representative image), the active GPIIb/IIIa receptor (FIG. 7A), or phosphatidylserine (FIG. 7B).

Figure 7E:
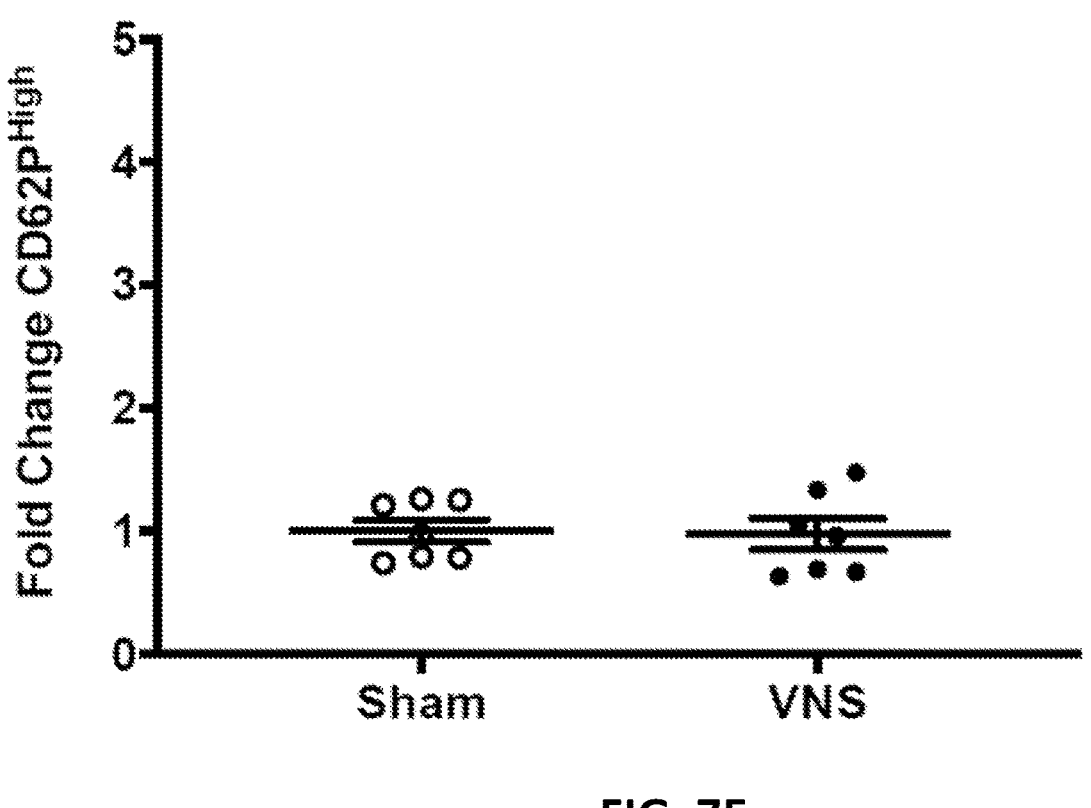
Figure 7F:
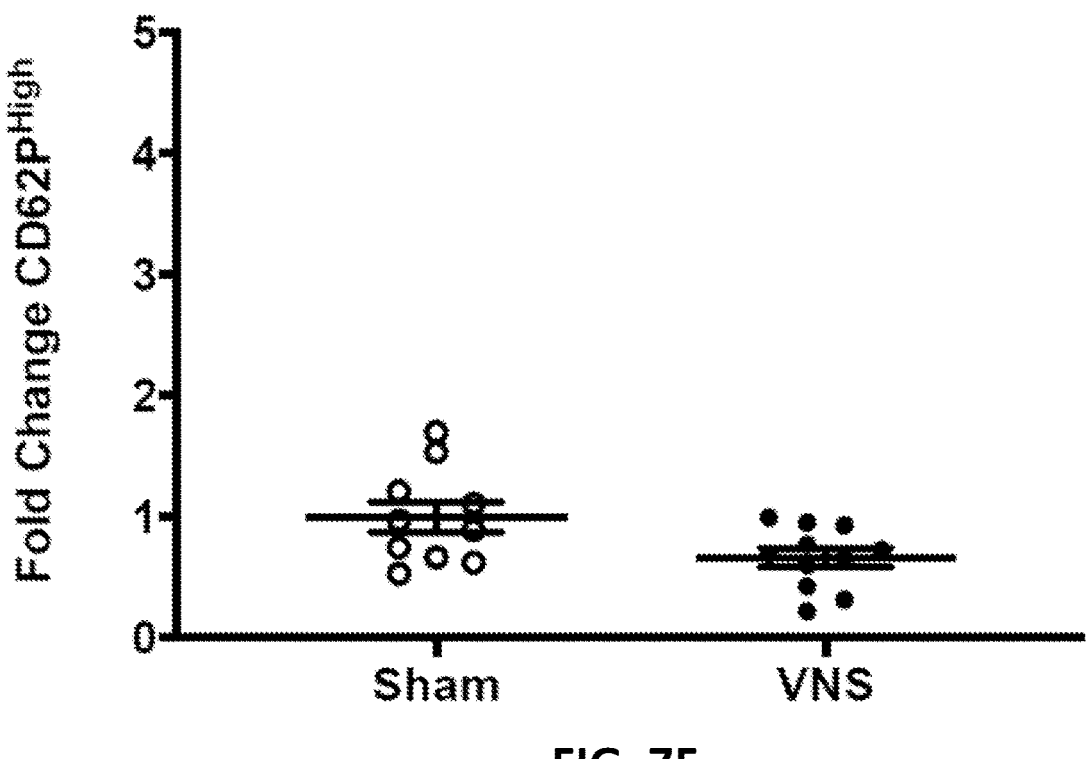

We then performed vagus nerve stimulation and exposed harvested circulating platelets to the calcium-dependent agonists thrombin, collagen, or adenosine diphosphate (ADP). In the presence of thrombin, significantly more platelets express P-selectin after vagus nerve stimulation as compared with sham stimulation (FIGS. 7E-7F, representative image). In contrast, expression of active GPIIb/IIIa or phosphatidylserine remains unchanged after vagus nerve stimulation as compared with sham stimulation (FIG. 7C-D). In a7nAChR-deficient mice, vagus nerve stimulation fails to increase P-selectin expression after thrombin exposure as compared with sham stimulation (FIG. 7G), further supporting the essential role of a7nAChR to platelet activation. In the presence of collagen or ADP, we did not observe any difference in P-selectin expression between vagus nerve stimulation or sham stimulation (FIGS. 7E-F). We did not observe any difference in active GPIIb/IIIa receptor or phosphatidylserine expression between vagus nerve stimulation or sham stimulation following exposure to collagen (FIGS. 7G-7H) or ADP (FIGS. 7I-7J). Together these results suggest vagus nerve stimulation enhances platelet activation by selectively increasing thrombin-mediated expression of P-selectin.

Figure 3C:
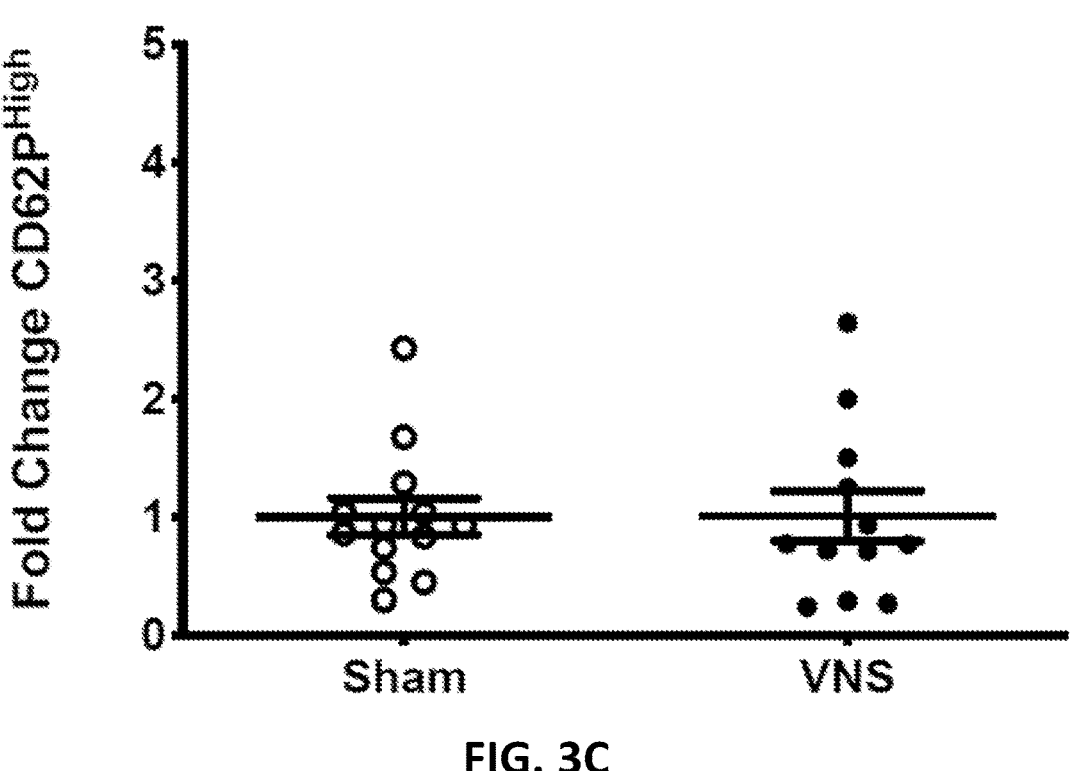
FIG. 3C, C57BL6/J mice received vagus nerve stimulation or sham stimulation before harvesting platelets for analysis of P-selectin (CD62P) expression. Data are presented as mean±s.e.m. (n=12-13 mice per group). p=NS vs. sham.
Figure 3D:
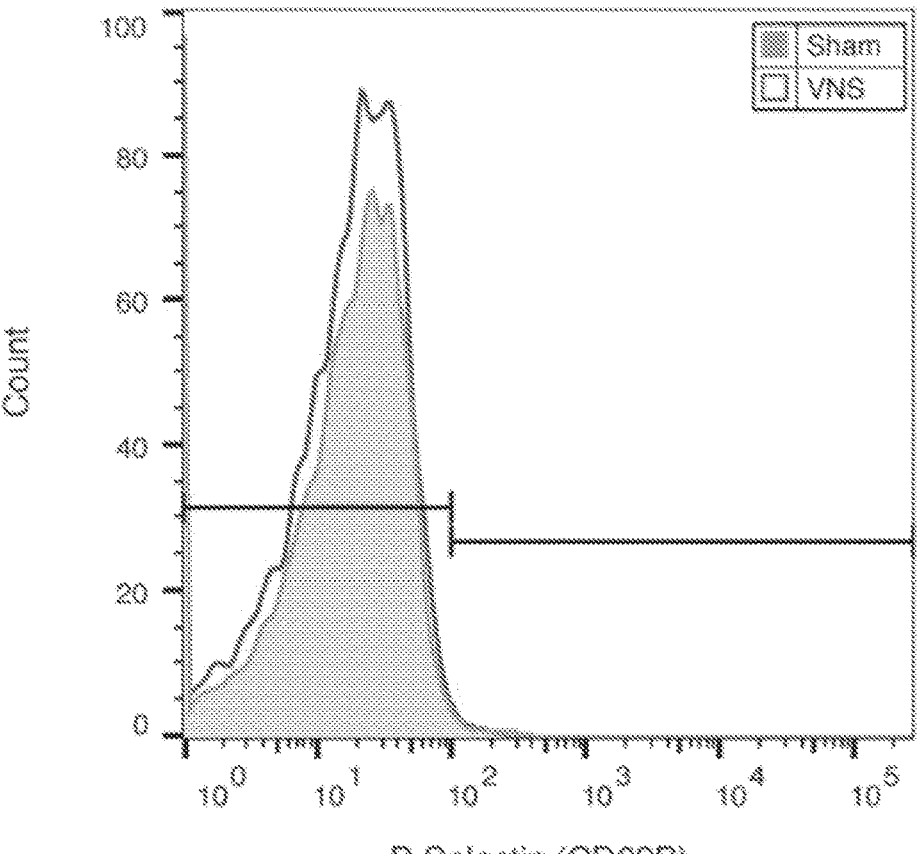
FIG. 3D, Representative FACS histogram of platelet P-selectin (CD62P) expression after vagus nerve stimulation or sham stimulation.
Figure 3E:
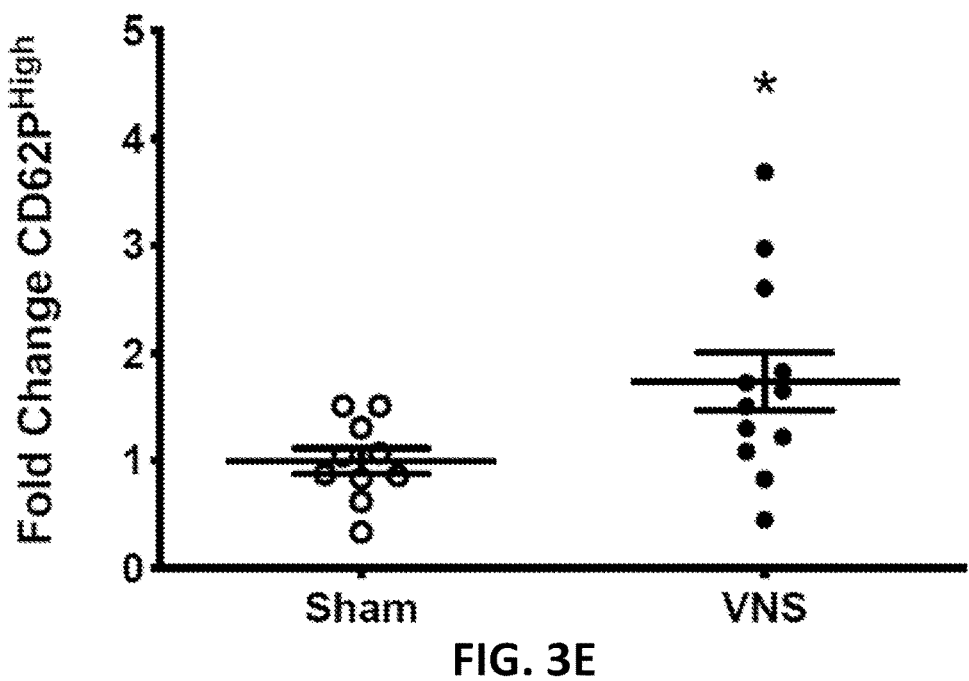
FIG. 3E, C57BL6/J mice received vagus nerve stimulation or sham stimulation before harvesting platelets, ex vivo thrombin stimulation, and analysis for P-selectin (CD62P) expression. Data are presented as mean±s.e.m. (n=10-12 mice per group). *, p<0.05 vs. sham.
Figure 3F:
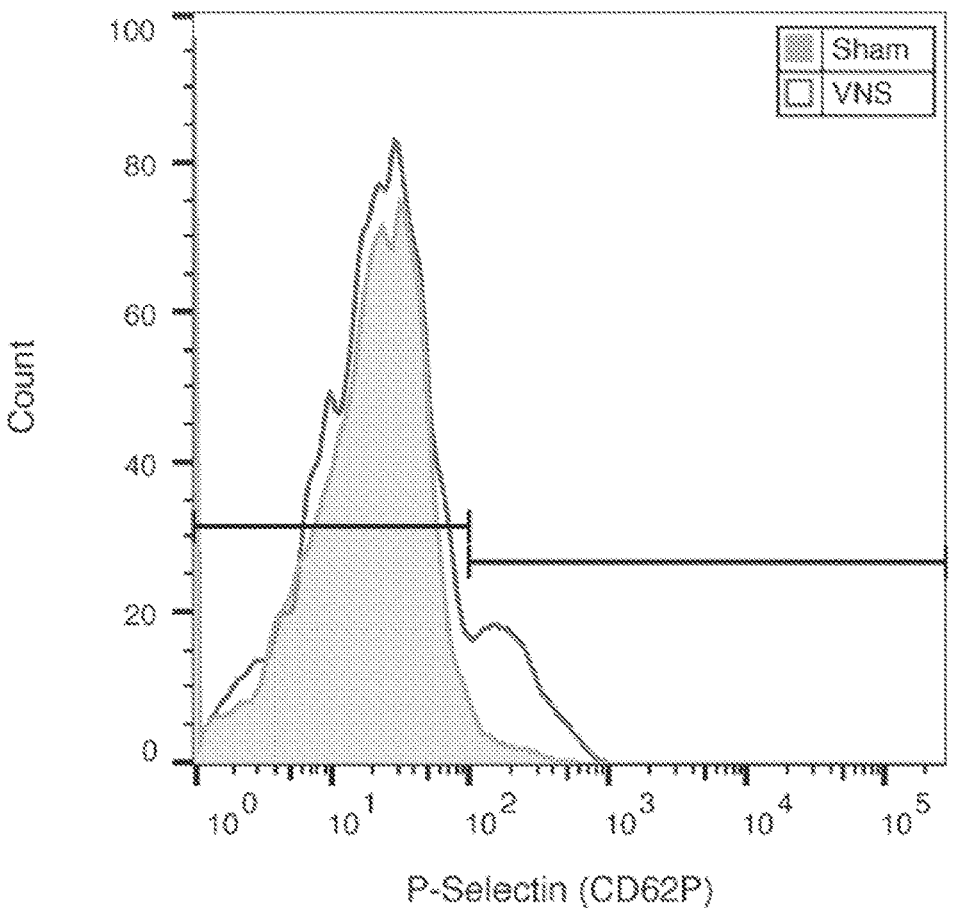
FIG. 3F, Representative FACS histogram of platelet P-selectin (CD62P) expression after vagus nerve stimulation or sham stimulation followed by ex vivo thrombin stimulation.
Figure 3G:
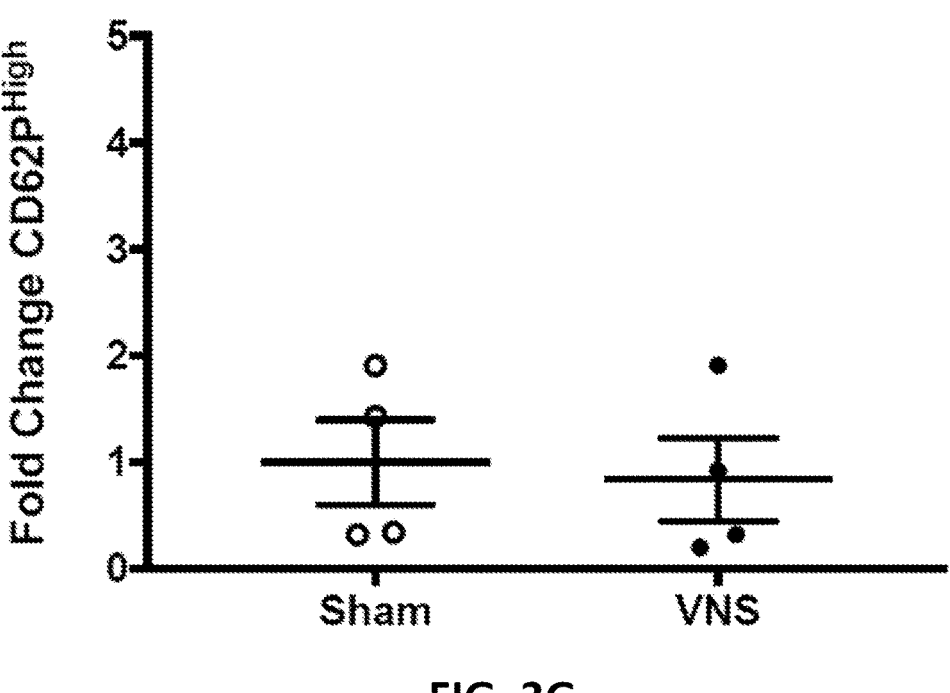
FIG. 3G, a7nAChR-deficient mice received vagus nerve stimulation or sham stimulation before harvesting platelets, ex vivo thrombin stimulation, and analysis for P-selectin (CD62P) expression. Data are presented as mean±s.e.m. (n=4 mice per group). *, p<0.05 vs. sham.
Figure 3H:
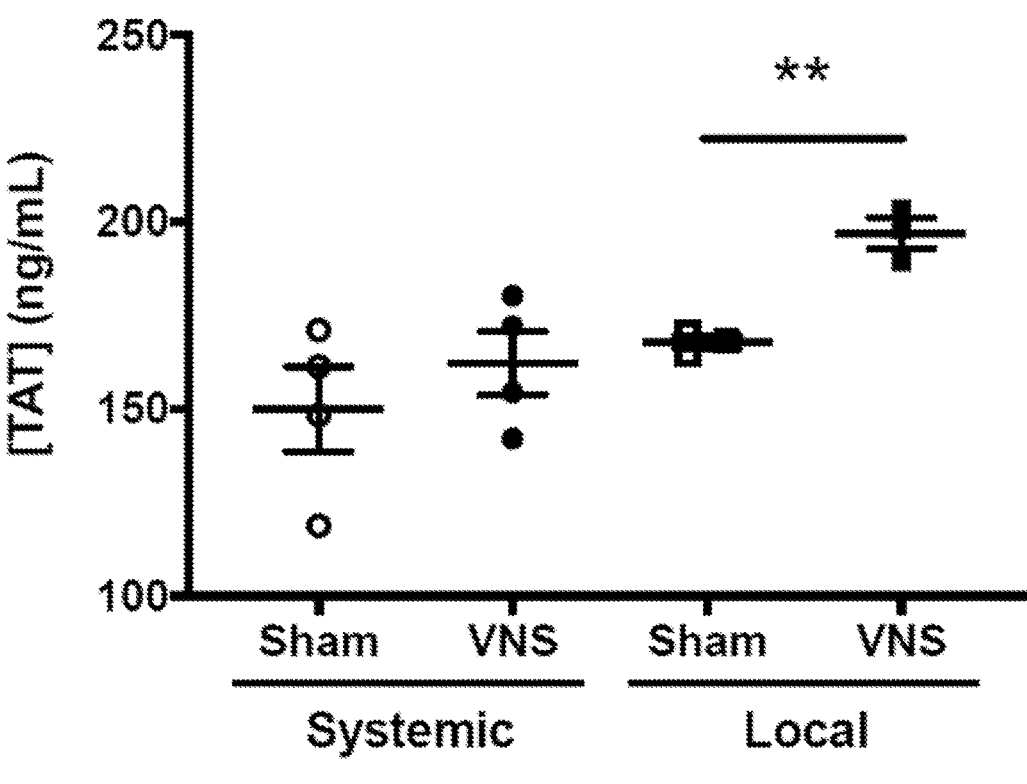
FIG. 3H, C57BL6/J mice received vagus nerve stimulation or sham stimulation before tail transection and collection of circulating and local shed blood for measurement of (TAT) complexes. Data are presented as mean±s.e.m. (n=3-4 mice per group). **, p<0.01 vs. sham.
Figures 8A, 8B, 8C, 8D, 8E, 8F:
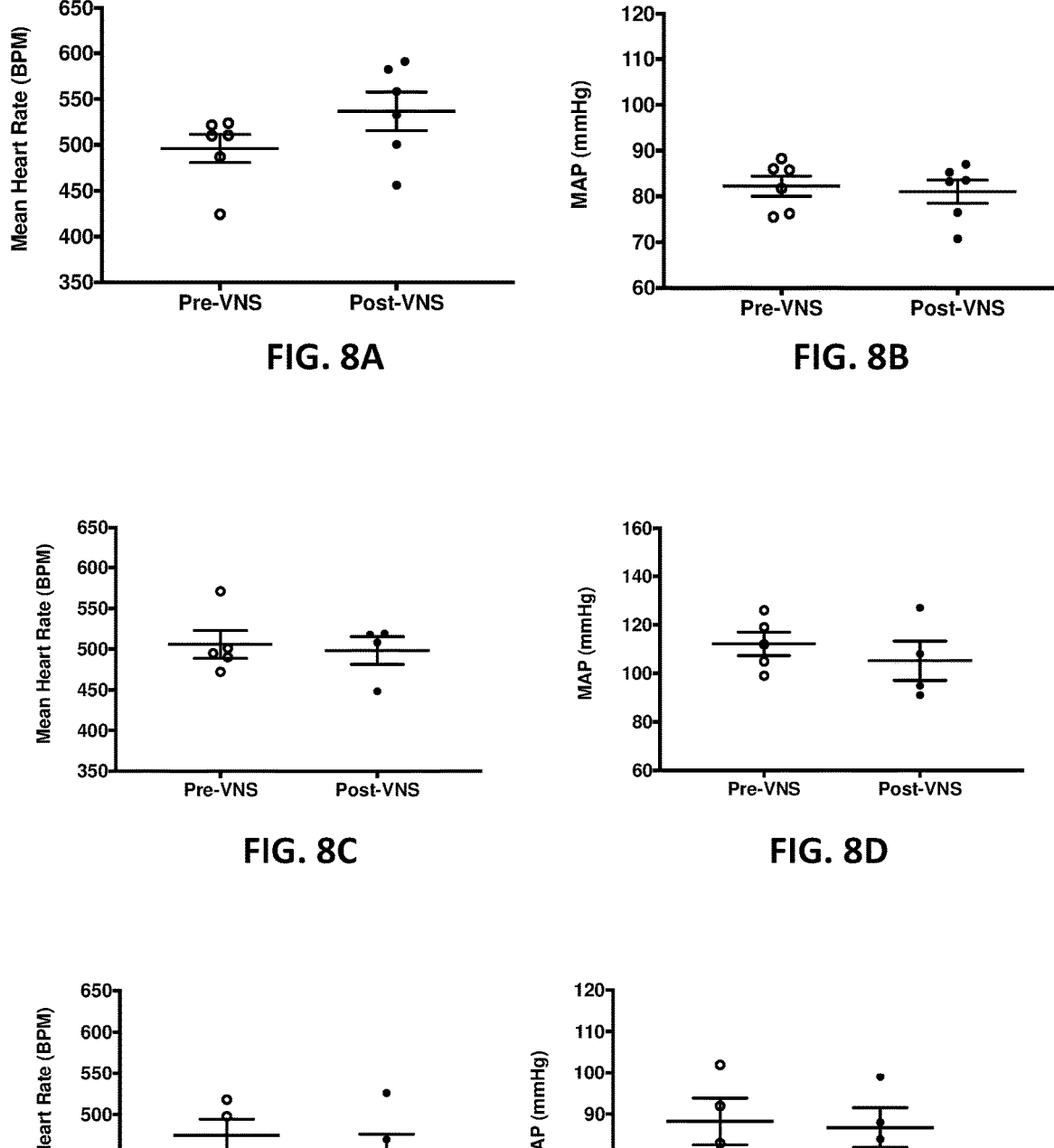
FIGS. 8A-8F show vagus nerve stimulation does not change heart rate, systemic blood pressure, or regional blood flow.
Figure 8G:
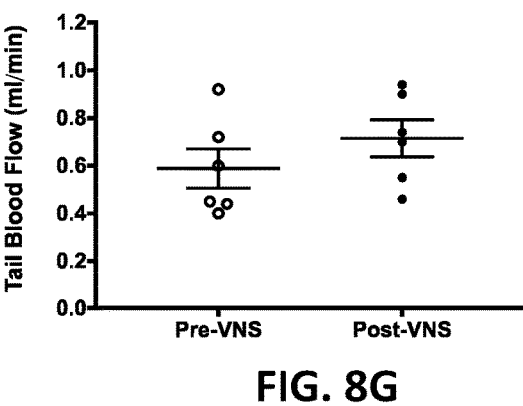
FIG. 8G, C57BL6/J mice underwent baseline tail blood flow measurement before and five minutes after vagus nerve stimulation. Data are presented as mean±s.e.m. Pre-VNS (n=6) and Post-VNS (n=6) mice per group. p=0.29 vs. baseline. Statistical significance was determined by unpaired two-tailed Student's t-test. Figure represents pooled results from 2 experiments performed independently.
Figure 8H:
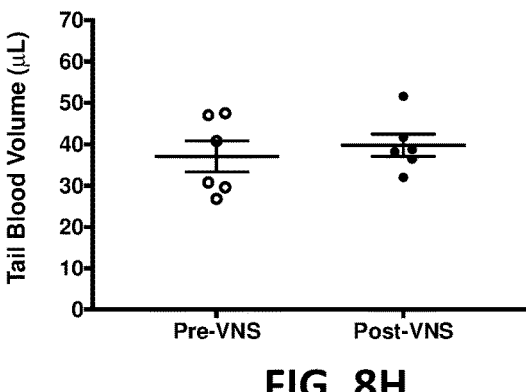
FIG. 8H, C57BL6/J mice underwent baseline tail blood volume measurement before and five minutes after vagus nerve stimulation. Data are presented as mean±s.e.m. Pre-VNS (n=6) and Post-VNS (n=6) mice per group. p=0.57 vs. baseline. Statistical significance was determined by unpaired two-tailed Student's t-test. Figure represents pooled results from 2 experiments performed independently. Source data are provided as a Source Data File.

Recruitment and activation of circulating platelets at a blood vessel injury site supports rapid thrombin generation that is crucial for fibrin deposition and stabilization of the developing clot. We evaluated thrombin production by measuring thrombin-antithrombin (TAT) complex concentrations. Vagus nerve stimulation significantly increases local TAT complex levels at the tail transection site as compared with sham stimulation (FIG. 3h). We did not observe any significant differences in systemic TAT complex levels between vagus nerve stimulation and sham stimulation (FIG. 3h). Similar to hemophilia A mice, wild-type animals demonstrate normal pulmonary architecture without evidence of thromboembolism after vagus nerve stimulation. Finally, to determine if parasympathetic to determine if the parasympathetic effects of vagus nerve stimulation contribute to hemostasis, we performed electrocardiograms and measured systemic blood pressure in wild-type, α7KO, and Foxn1nu mice. Compared with pre-stimulation, we did not observe any differences in post-stimulation mean heart rate or arterial blood pressure in wild-type (FIGS. 8A-8B), α7KO (FIGS. 8C-8D), or Foxn1nu mice (FIGS. 8E-8F). Furthermore, we did not observe any differences in post-stimulation tail blood flow (FIG. 8G) or tail blood volume in wild-type mice (FIG. 8H). These findings suggest vagus nerve stimulation primes circulating platelets to accelerate local clot formation without inducing systemic thrombosis or influencing systemic hemodynamics or tissue perfusion to the site of injury.

Figure 4:
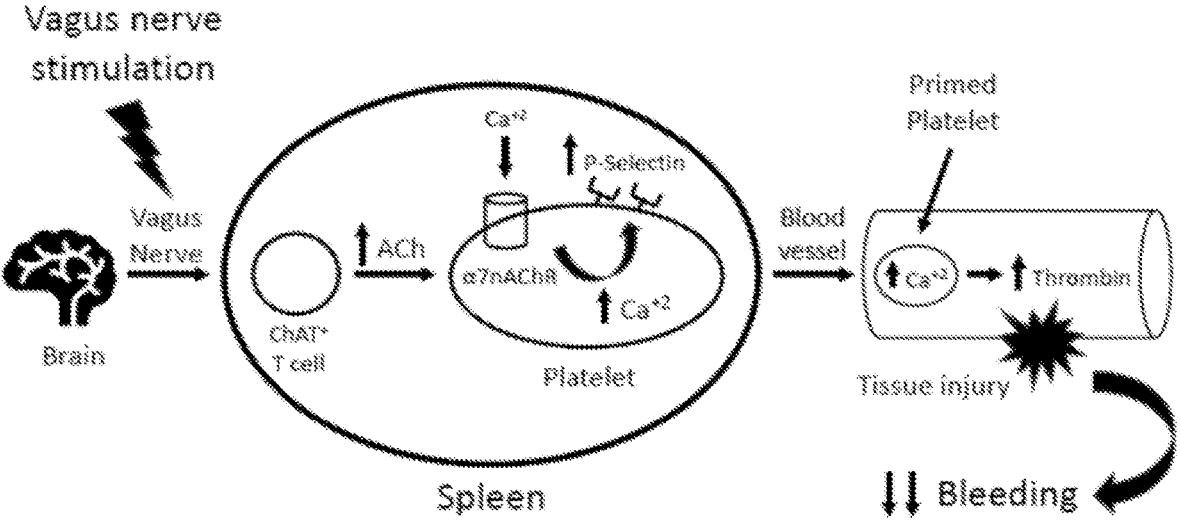
FIG. 4 Illustrates how vagus nerve stimulation harnesses acetylcholine-producing ChAT+ T cells in spleen to stimulate platelet calcium uptake via an α7nAChR-dependent mechanism. Vagus nerve-primed platelets travel to sites of tissue injury, enhance thrombin production, accelerate thrombosis, and reduce bleeding.

Taken together, these studies reveal a previously unrecognized neural hemostatic mechanism (FIG. 4). The vagus nerve targets spleen to access circulating platelets that occupy a critical role in hemostasis. Previously implicated in relaying neural signals in the inflammatory reflex, regulating blood pressure and vascular contractility via endothelial cholinergic receptors, and controlling cytotoxic T cells and clearance of chronic viral infection, the data here implicate memory subtype (CD4+CD44high CD62low ChAT-EGFP+) T lymphocytes in regulation of platelet function and hemostasis. Following vagus nerve stimulation, ChAT-EGFP+ T cell release of acetylcholine may potentiate platelet a7nAChR signaling in spleen by avoiding rapid degradation via circulating blood acetylcholinesterases. Release of other endogenous ligands following vagus nerve stimulation may contribute to platelet activation. Previous work shows splenic lymphocytes secrete ChAT, which may synthesize additional extracellular acetylcholine to support a7nAChR signaling. Establishing a role for ChAT-EGFP+ T lymphocytes in modulating bleeding provides further insights into how hemostatic and immunologic mechanisms control the host response to injury.

Circulating platelets are quiescent unless exposed to vascular injury, where their upregulation of coagulation factor activity creates a stable fibrin clot. Since vagus nerve stimulation increases platelet cytosolic calcium via a7nAChR to facilitate activation, this priming phenomenon enhances systemic platelet function and extends neural control of hemostasis to anatomic sites lacking direct vagal innervation. Vagus nerve stimulation does not facilitate activation in all platelets, which may relate, in part, to only 60% expressing surface a7nAChR. Because we utilized acute hemorrhage and thrombosis models, it is unclear whether platelets remain in a primed state after vagus nerve stimulation or if repeated stimulation is necessary to enhance their function. Ongoing platelet clearance from the circulation may also impact hemostasis during chronic vagus nerve stimulation.

Although a7nAChR functions as a traditional ligand-gated ion channel in neuronal cells, it activates G-protein coupled, inositol triphosphate (IP3)-induced calcium release in neuronal and non-neuronal immune cells. Our finding that vagus nerve stimulation requires extracellular calcium to increase platelet cytosolic calcium is consistent with cholinergic signaling in human platelets and suggests canonical a7nAChR ion channels facilitate platelet activation, accelerated thrombosis, and decreased bleeding. Additional studies may determine if metabotropic a7nAChR signaling upregulates platelets after vagus nerve stimulation. Because transferring calcium-primed platelets to naïve animals improves hemostasis, administering vagus nerve stimulation to blood donors may improve platelet function in recipients. Vagus nerve stimulation may reduce overall transfusion volumes, minimize transfusion-related complications and costs, and ease the burden on blood bank stores.

Increasing evidence suggests bioelectronic approaches are feasible for chronic treatment of medically-refractory depression, epilepsy, rheumatoid arthritis, and Crohn's disease. Since 1997, more than 100,000 patients have received vagus nerve stimulation via implantable pulse generators. Despite their favorable safety profile, surgery poses a risk of bleeding, infection, and injury to important anatomic structures. The advent of noninvasive approaches, such as transcutaneous cervical vagus nerve stimulation and transcutaneous stimulation of the auricular branch of the vagus nerve, may mitigate these risks. Noninvasive techniques may allow for emergent treatment of traumatic injury in individuals not fitted with an implantable device. Hemophilia A affects hundreds of thousands of individuals and causes significant morbidity and mortality. It may be useful to explore the use of vagus nerve stimulation to treat hemophilia A and other bleeding disorders in clinical trials.

TABLE 1

| Complete blood cell counts | | | | |
|---|---|---|---|---|
| | SHAM | | VNS | |
| | Avg. | S.E.M. | Avg. | S.E.M. | p value |
| WBC (K/μL) | 2.67 | 0.70 | 2.94 | 1.24 | p > 0.05 |
| Hb (g/L) | 12.08 | 0.35 | 11.58 | 0.48 | p > 0.05 |
| Het (%) | 44.03 | 0.68 | 42.20 | 1.19 | p > 0.05 |
| Plt (K/μL) | 758 | 90.5 | 724.3 | 90.9 | p > 0.05 | n = 4 mice per group

FIGS. 1A-1E Vagus nerve stimulation reduces traumatic blood loss and accelerates clot formation in hemophilia A mice. FIG. 1A, Circulating factor VIII activity in wild-type and factor VIII deficient (hemophilia A) mice. Data are presented as mean±s.e.m. (n=7 mice). ****, p<0.0001 vs. control. FIG. 1B, Hemophilia A mice received rFVIII (Advate®, 200 U/kg, r.o.) or vehicle before tail transection. Data are presented as mean±s.e.m. (n=7-8 mice per group). *, p<0.05 vs. sham. FIG. 1C, Hemophilia A mice received vagus nerve stimulation or sham stimulation before tail transection. Data are presented as mean±s.e.m. (n=8-9 mice per group). , p<0.01 vs. sham. FIG. 1D, Hemophilia A mice received vagus nerve stimulation or sham stimulation before blood collection to determine factor VIII activity. Data are presented as mean±s.e.m. (n=8-11 mice per group). p=NS vs. sham. e, Hemophilia A mice received vagus nerve stimulation or sham stimulation carotid artery injury and thrombosis. Data are presented as mean±s.e.m. (n=6 mice per group). **, p<0.0001 vs. sham. f, Representative images of lungs from hemophilia A mice after sham stimulation. FIG. 1G, Representative images of lungs from hemophilia A mice after vagus nerve stimulation.

FIGS. 6A-6H Vagus nerve stimulation harnesses choline acetyltransferase-expressing T cells in spleen to stimulate platelets via a7nAChR. FIG. 6A, C57BL6/J mice underwent splenectomy or sham splenectomy followed by vagus nerve stimulation or sham stimulation before tail transection. Data are presented as mean±s.e.m. (n=6-9 mice per group). **, p<0.01 versus sham. FIG. 6B, Wild-type BALB/c or T lymphocyte deficient (Foxn1nu) mice received vagus nerve stimulation or sham stimulation before tail transection. Data are presented as mean±s.e.m. (n=4-6 mice per group). *, p=0.05 vs. sham. FIG. 6C, T lymphocyte deficient (Foxn1nu) mice were reconstituted with ChAT-eGFP+ or ChAT-eGFP− cells followed by vagus nerve stimulation or sham stimulation before tail transection. Data are presented as mean±s.e.m. (n=5-8 mice per group). **, p<0.01 vs. sham. FIG. 6D, Platelets from uninjured C57BL6/J mice receiving vagus nerve stimulation or sham stimulation were transferred into naïve animals before tail transection. Data are presented as mean±s.e.m. (n=8-9 mice per group). *, p<0.05 vs. sham. FIG. 6E, Wild-type or a7nAChR-deficient mice received vagus nerve stimulation or sham stimulation before tail transection. Data are presented as mean±s.e.m. (n=4-5 mice per group). *, p<0.05 vs. sham. FIG. 6F, Wild-type or a7nAChR-deficient mice received vagus nerve stimulation or sham stimulation before carotid artery injury and thrombosis. Data are presented as mean±s.e.m. (n=5 mice per group). *, p<0.05 vs. sham. FIG. 6G, Wild-type or a7nAChR-deficient mice received nicotine or vehicle before tail transection. Data are presented as mean±s.e.m. (n=4-8 mice per group). **, p<0.01 vs. vehicle control. FIG. 6H, a7nAChR deficient mice were reconstituted with platelets from wild-type or a7nAChR-deficient mice followed by treatment with nicotine or vehicle before tail transection. Data are presented as mean±s.e.m. (n=5-7 mice per group). *, p<0.05 vs. vehicle control.

Figure 7G:
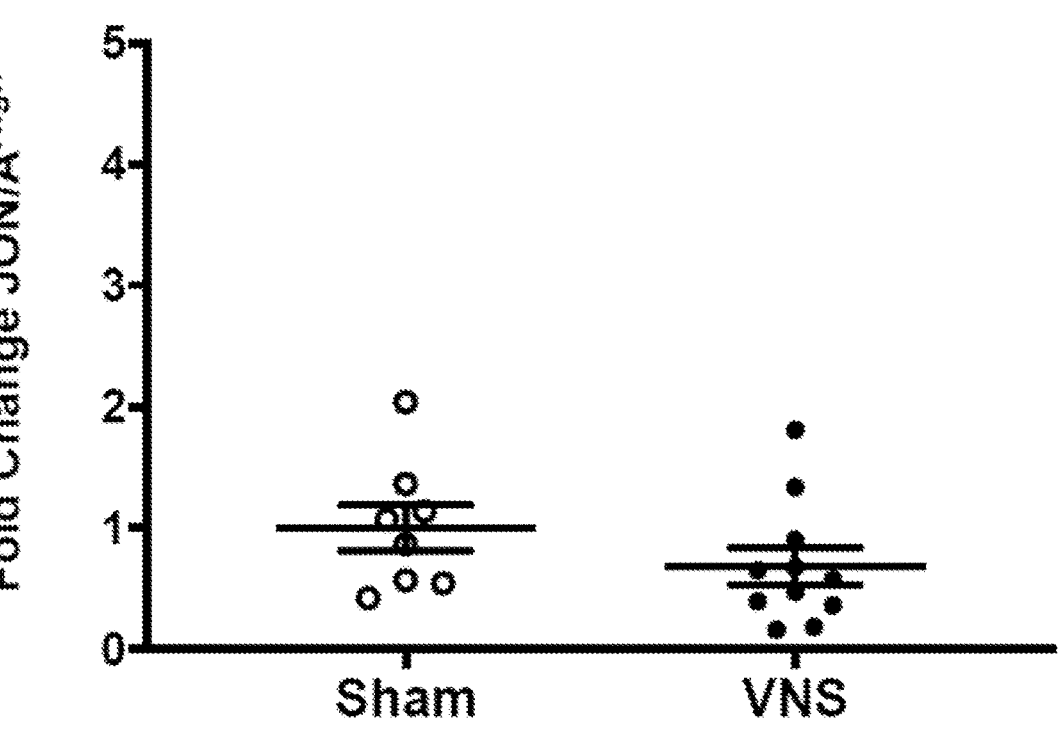
Figure 7H:
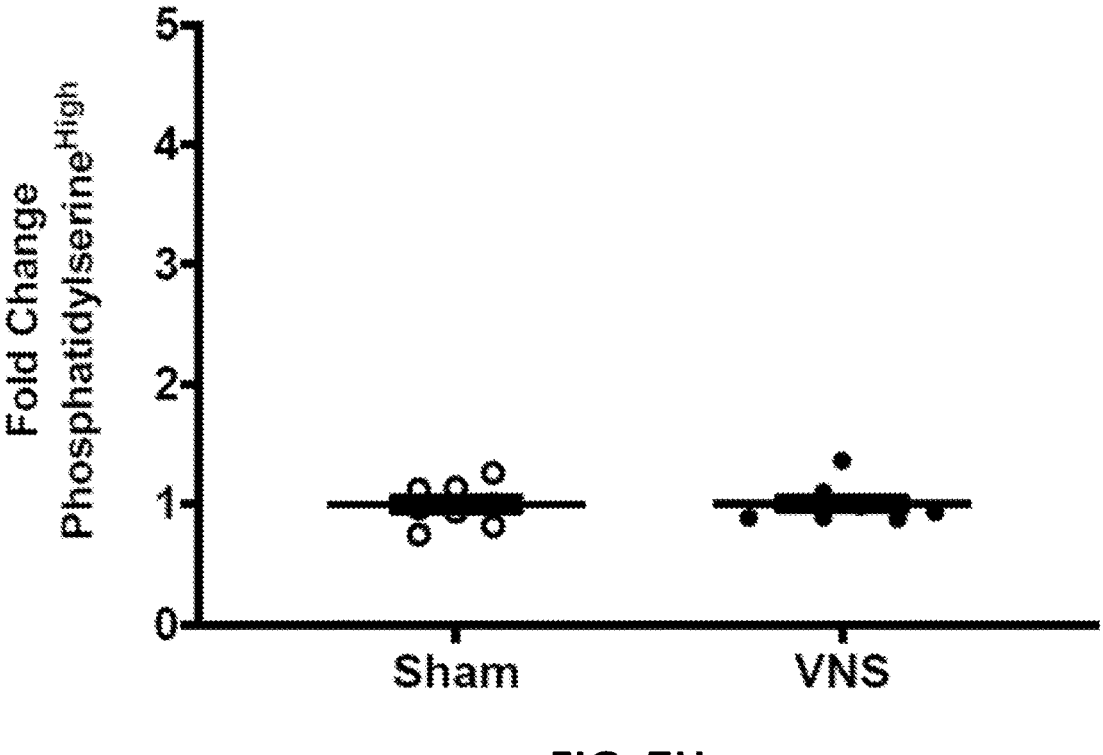
Figure 7I:
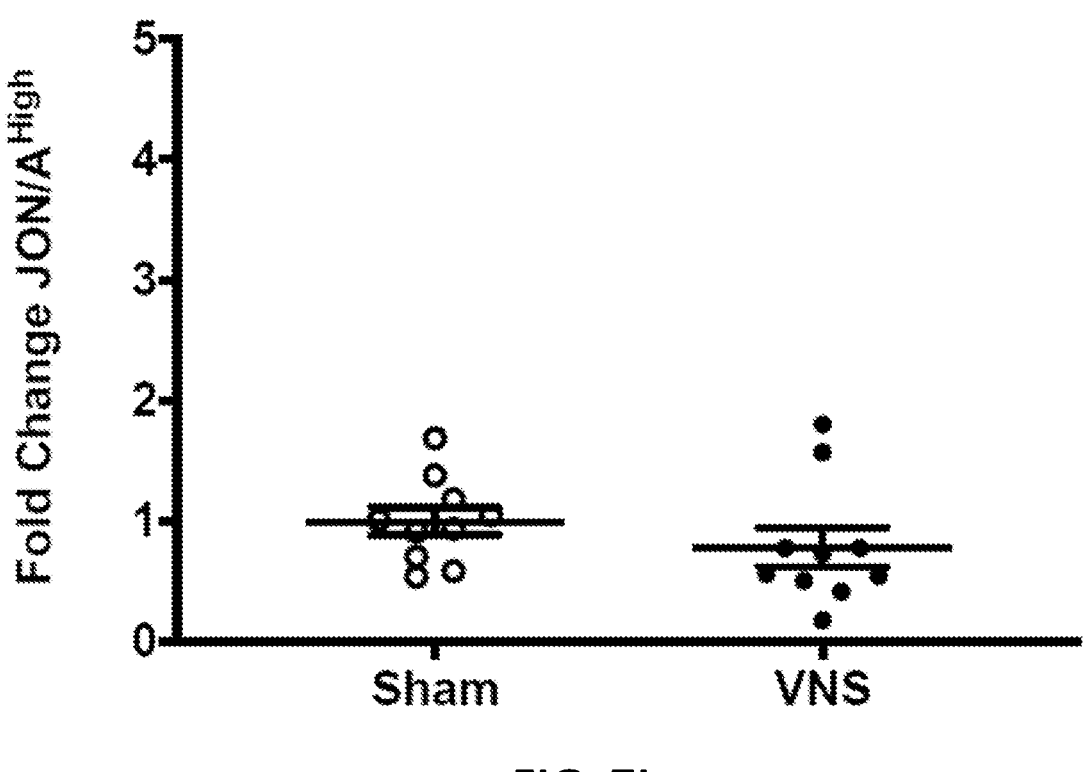
Figure 7J:
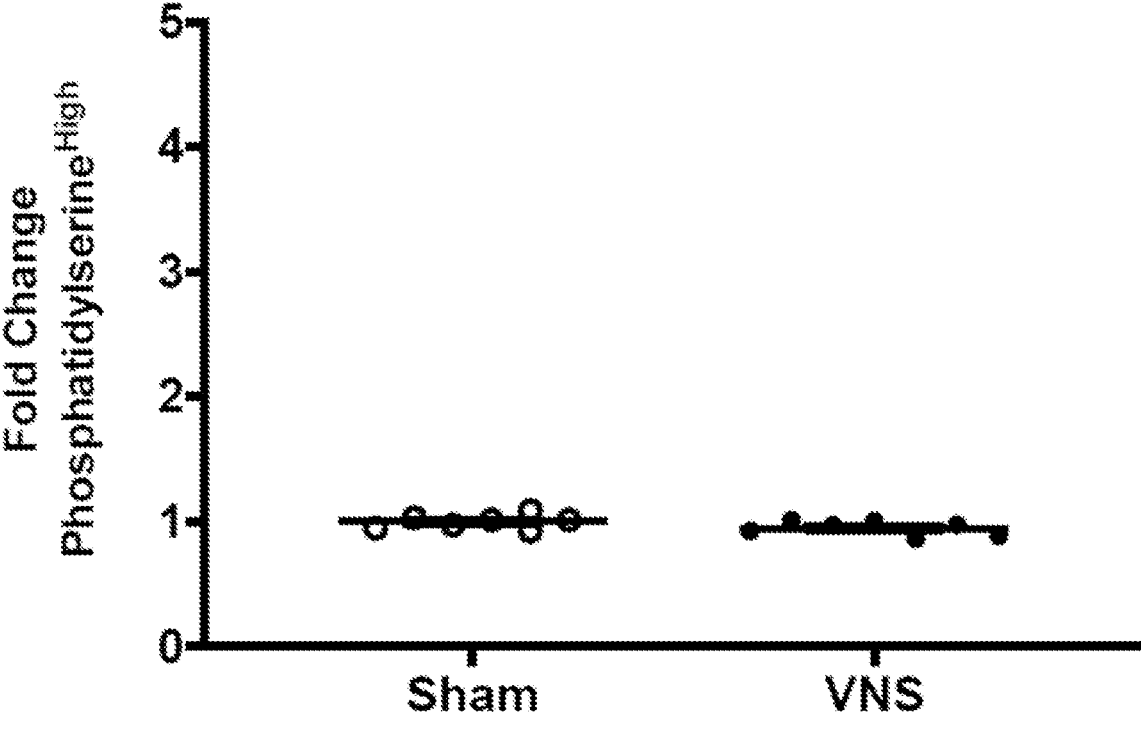

FIGS. 7A-7H Vagus nerve stimulation requires a7nAChR to increase platelet cytosolic calcium, enhance cellular activation, and accelerate local clot formation. FIG. 7A, C57BL6/J mice received vagus nerve stimulation or sham stimulation before harvesting circulating platelets to measure basal cytosolic calcium uptake. Data are presented as mean±s.e.m. (n=5-6 mice per group). **, p<0.01 vs. sham. FIG. 7B, a7nAChR-deficient mice received vagus nerve stimulation or sham stimulation before harvesting circulating platelets to measure basal cytosolic calcium uptake. Data are presented as mean±s.e.m. (n=4 mice per group). p=NS vs. sham. FIG. 7C, C57BL6/J mice received vagus nerve stimulation or sham stimulation before harvesting platelets for analysis of P-selectin (CD62P) expression. Data are presented as mean±s.e.m. (n=12-13 mice per group). p=NS vs. sham. FIG. 7D, Representative FACS histogram of platelet P-selectin (CD62P) expression after vagus nerve stimulation or sham stimulation. FIG. 7E, C57BL6/J mice received vagus nerve stimulation or sham stimulation before harvesting platelets, ex vivo thrombin stimulation, and analysis for P-selectin (CD62P) expression. Data are presented as mean±s.e.m. (n=10-12 mice per group). *, p<0.05 vs. sham. FIG. 7F, Representative FACS histogram of platelet P-selectin (CD62P) expression after vagus nerve stimulation or sham stimulation followed by ex vivo thrombin stimulation. FIG. 7G, a7nAChR-deficient mice received vagus nerve stimulation or sham stimulation before harvesting platelets, ex vivo thrombin stimulation, and analysis for P-selectin (CD62P) expression. Data are presented as mean±s.e.m. (n=4 mice per group). *, p<0.05 vs. sham. FIG. 7H, C57BL6/J mice received vagus nerve stimulation or sham stimulation before tail transection and collection of circulating and local shed blood for measurement of (TAT) complexes. Data are presented as mean±s.e.m. (n=3-4 mice per group). **, p<0.01 vs. sham. FIG. 7I, Representative lung images from C57BL6/J mice after sham stimulation. FIG. 7J, Representative lung images from C57BL6/J mice after vagus nerve stimulation.

FIG. 4 The Neural Tourniquet. Vagus nerve stimulation harnesses acetylcholine-producing ChAT+ T cells in spleen to stimulate platelet calcium uptake via an a7nAChR-dependent mechanism. Vagus nerve-primed platelets travel to sites of tissue injury, stimulate thrombin production and local thrombosis, and reduce bleeding time.

FIGS. 5A and 5B Effect of vagus nerve stimulation on platelet a7nAChR expression. FIG. 5A shows C57BL6/J mice received vagus nerve stimulation or sham stimulation before harvesting circulating platelets to measure percent expression of a7nAChR. Data are presented as mean±s.e.m. (n=8-9 mice per group). p=NS vs. sham. FIG. 5B shows C57BL6/J mice received vagus nerve stimulation or sham stimulation before harvesting platelets to measure a7nAChR expression levels. Data are presented as mean±s.e.m. (n=12-14 mice per group). p=NS vs. sham.

FIGS. 5A-5B show vagus nerve stimulation requires extracellular source to increase platelet calcium. C57BL6/J mice received vagus nerve stimulation or sham stimulation before harvesting circulating platelets to measure basal cytosolic calcium uptake in the absence of extracellular calcium. Data are presented as mean±s.e.m. (n=3 mice per group). p=NS vs. sham.

FIG. 6A-6B illustrate the effect of vagus nerve stimulation on platelet activated GPIIb/IIIa, phosphatidylserine, or P-selectin expression. a, C57BL6/J mice received vagus nerve stimulation or sham stimulation before harvesting platelets for analysis of activated GPIIb/IIIa (JON/A) expression. Data are presented as mean±s.e.m. (n=13 mice per group). p=NS vs. sham. b, C57BL6/J mice received vagus nerve stimulation or sham stimulation before harvesting platelets and analysis of phosphatidylserine. Data are presented as mean±s.e.m. (n=13-14 mice per group). p=NS vs. sham. c, C57BL6/J mice received vagus nerve stimulation or sham stimulation before harvesting platelets, ex vivo thrombin stimulation, and analysis of activated GPIIb/IIIa (JON/A) expression. Data are presented as mean±s.e.m. (n=9-10 mice per group). p=NS vs. sham. d, C57BL6/J mice received vagus nerve stimulation or sham stimulation before harvesting platelets, ex vivo thrombin stimulation, and analysis of phosphatidylserine expression. Data are presented as mean±s.e.m. (n=10-11 mice per group). p=NS vs. sham. e, C57BL6/J mice received vagus nerve stimulation or sham stimulation before harvesting platelets, ex vivo collagen stimulation, and analysis for P-selectin (CD62P) expression. Data are presented as mean±s.e.m. (n=7 mice per group). p=NS vs. sham. f, C57BL6/J mice received vagus nerve stimulation or sham stimulation before harvesting platelets, ex vivo ADP stimulation, and analysis for P-selectin (CD62P) expression. Data are presented as mean±s.e.m. (n=10-11 mice per group). p=NS vs. sham. g, C57BL6/J mice received vagus nerve stimulation or sham stimulation before harvesting platelets, ex vivo collagen stimulation, and analysis of activated GPIIb/IIIa (JON/A) expression. Data are presented as mean±s.e.m. (n=8-11 mice per group). p=NS vs. sham. h, C57BL6/J mice received vagus nerve stimulation or sham stimulation before harvesting platelets, ex vivo collagen stimulation, and analysis of phosphatidylserine expression. Data are presented as mean±s.e.m. (n=8 mice per group). p=NS vs. sham. i, C57BL6/J mice received vagus nerve stimulation or sham stimulation before harvesting platelets, ex vivo ADP stimulation, and analysis of activated GPIIb/IIIa (JON/A) expression. Data are presented as mean±s.e.m. (n=10 mice per group). p=NS vs. sham. j, C57BL6/J mice received vagus nerve stimulation or sham stimulation before harvesting platelets, ex vivo ADP stimulation, and analysis of phosphatidylserine expression. Data are presented as mean±s.e.m. (n=7 mice per group). p=NS vs. sham.

FIGS. 8A-8F show vagus nerve stimulation does not change heart rate. C57BL6/J mice underwent baseline heart rate measurement before and one minute after vagus nerve stimulation. Data are presented as mean±s.e.m. (n=4 mice per group). p=NS vs. sham.

FIG. 9 illustrates a Platelet gating strategy for flow cytometry. a, Preliminary FSC/SSC gates for starting platelet cell population from murine systemic whole blood. b, Platelet cell population identification with anti-CD41a.

METHODS

Mice

Adult male 8-12 week old BALB/c mice (20-25 g, Taconic), adult male 8-12 week old C57BL6/J mice (20-25 g, Jackson Labs), adult male 8-16 week old a7nAChR-deficient mice (20-25 g, Jackson Labs, C57BL6/J background) and wild-type littermates, adult male 8-12 week old (Foxn1nu) nude mice (20-25 g Taconic, BALB/c background), adult male 8-12 week old factor VIII knockout mice (20-25 g, Jackson Labs) are housed at 25° C. on a 12-hour light/dark cycle. Standard animal chow and water are freely available. All animal experiments are performed in accordance with the National Institutes of Health (NIH)

Guidelines under protocols approved by the Institutional Animal Care and Use Committee of The Feinstein Institutes for Medical Research.

Vagus Nerve Stimulation

Animals are anesthetized with ketamine (144 mg/kg, i.p.) and xylazine (14 mg/kg, i.p.). After seven minutes, animals are placed in a supine position, and a 1-2 cm ventral midline cervical skin incision is made between the mandible and sternum. The subcutaneous tissue and mandibular salivary glands are dissected and retracted laterally. The left vagus nerve is isolated from between the sternomastoid and sternohyoid muscles, dissected free from the neighboring carotid artery, and controlled with a 5-0 prolene suture. The nerve is then mounted on bipolar platinum electrodes (Plastics One). Constant voltage stimuli (1 V, 30 Hz, 2 ms pulse width) are applied for five minutes. Electrical stimuli are generated using an MP36R Data Acquisition System (Biopac Systems, Goleta, CA) attached to an out 3 low voltage stimulation adapter. Sham-stimulated animals receive cervical skin incision and dissection of the salivary glands, but the vagus nerve is neither isolated nor dissected free from neighboring structures.

Tail Transection and Hemorrhage

Mice are screened before study inclusion to ensure visual similarity and consistency between the anatomy of the tail tips and the site of transection. Any animals displaying aberrant anatomy and/or injury that does not meet our predetermined criteria are excluded. Following vagus nerve stimulation or sham surgery, tails are immersed in water at 37+1° C. for five minutes. Tails are then removed from the solution, amputated 2 mm from the tip with a razor blade, and immediately placed into a 50 mL beaker containing water at 37+1° C. Tails are allowed to bleed uncontrolled until bleeding stops for a minimum of ten seconds. This duration of bleeding is recorded as bleeding time. For analyses of bleeding in factor VIII deficient mice, tails are first immersed in 0.9% saline at 37±1° C. for five minutes. Tails are then removed and amputated 2 mm from the tip with a razor blade. Tails are then placed into a 50 mL conical tube containing 0.9% saline at 37±1° C. Tails are allowed to bleed freely for a total of ten minutes. Total blood loss is determined by densitometry by measuring absorbance at 550 nm. A standard curve is created from a known volume of blood.

Ferric Chloride Induced Carotid Artery Injury

Animals are anesthetized with isoflurane (1-2%), placed in the supine position, and a 1-2 cm ventral midline cervical skin incision is made between the mandible and sternum. The left vagus nerve is isolated from the carotid sheath and placed on a bipolar electrode and stimulated (1 V, 30 Hz, 2 ms pulse width, 5 minutes). Following stimulation or sham surgery, the right carotid artery is dissected free from surrounding tissue for a distance of 5 mm, and the artery is bathed in 5 uL of a 10% ferric chloride (FeCl3) solution for 3 minutes (F8KO mice) or a 5% FeCl3 solution for 1 minute (C57BL6/J and a7KO mice). The carotid artery is then rinsed with 0.9% normal saline. A doppler ultrasound probe (L8-18i-RS, GE) attached to a GE Logiq e ultrasound system is placed over both carotid arteries to record blood flow for a total of 25 minutes. Experimental end points include cessation of blood flow for >1 minute as determined by absence of arterial waveform on motion mode (m-mode) and doppler signal as compared to the contralateral, unaffected carotid artery. If occlusion is not observed after 25 minutes, the time is recorded as 25 minutes for statistical comparisons.

Splenectomy

Animals are anesthetized with ketamine (144 mg/kg, i.p.) and xylazine (14 mg/kg, i.p.). Animals are placed in a supine position, and a 2 cm laparotomy incision is made with a scalpel. The spleen is exteriorized and the splenic artery and vein ligated with a 5-0 prolene suture. The peritoneum is closed with 5-0 Vicryl simple interrupted sutures and the skin with a 7 mm skin stapler. Sham splenectomized animals undergo midline laparotomy only. Splenectomy or sham splenectomy is performed six weeks before tail transection.

Heart Rate Recording

Animals are anesthetized with isoflurane (3% induction, maintenance 1.5%). Animals are placed in the supine position, a 1-2 cm ventral midline cervical skin incision is made and the left vagus nerve is isolated and controlled as described above. The nerve is mounted on bipolar platinum electrodes (Plastics One) and constant voltage stimulation (1 V, 30 Hz, 2 ms pulse width) is applied for five minutes. Heart rate data is acquired at 30 Hz using the OmniPlex Neural Data Acquisition System (Plexon, Inc.). Data is analyzed offline using Spike2 software (Cambridge Electronic Design Ltd.). Heart rate is calculated as beats per minute (BPM). Pre-stimulation is defined as a 20 second epoch beginning 5 minutes after transition to maintenance anesthesia. Post-stimulation is defined as a 20 second epoch beginning 1 minute after vagus nerve stimulation. Pre- and post-stimulation heart rates are compared using Mann-Whitney U-test.

Platelet Priming

Figure 9A:
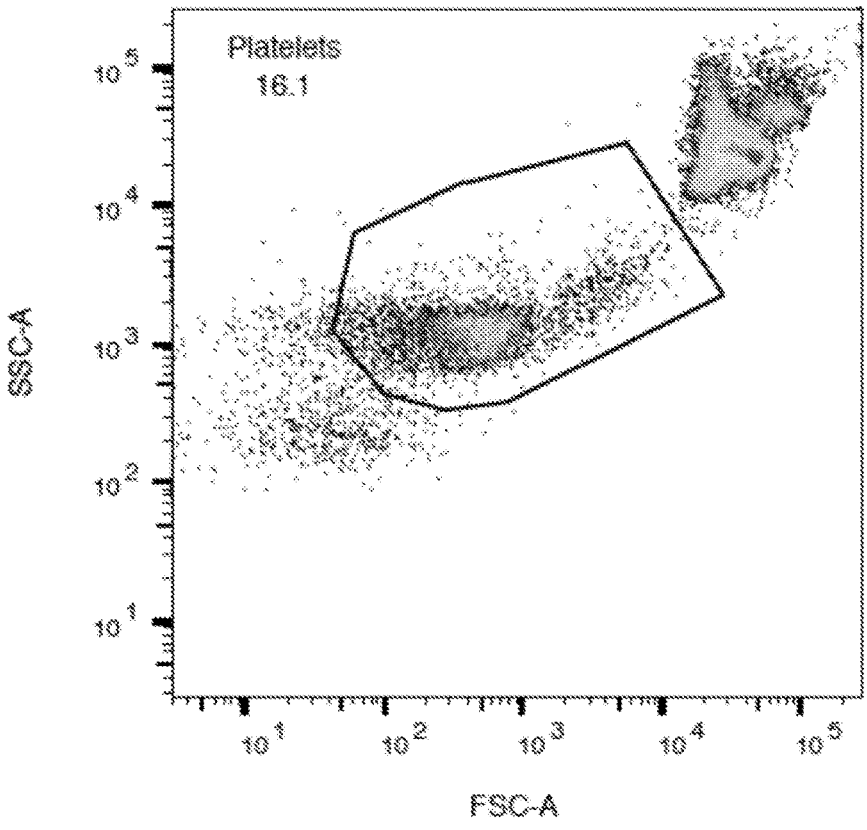
FIGS. 9A-9B show platelet gating strategy for flow cytometry.
Figure 9B:
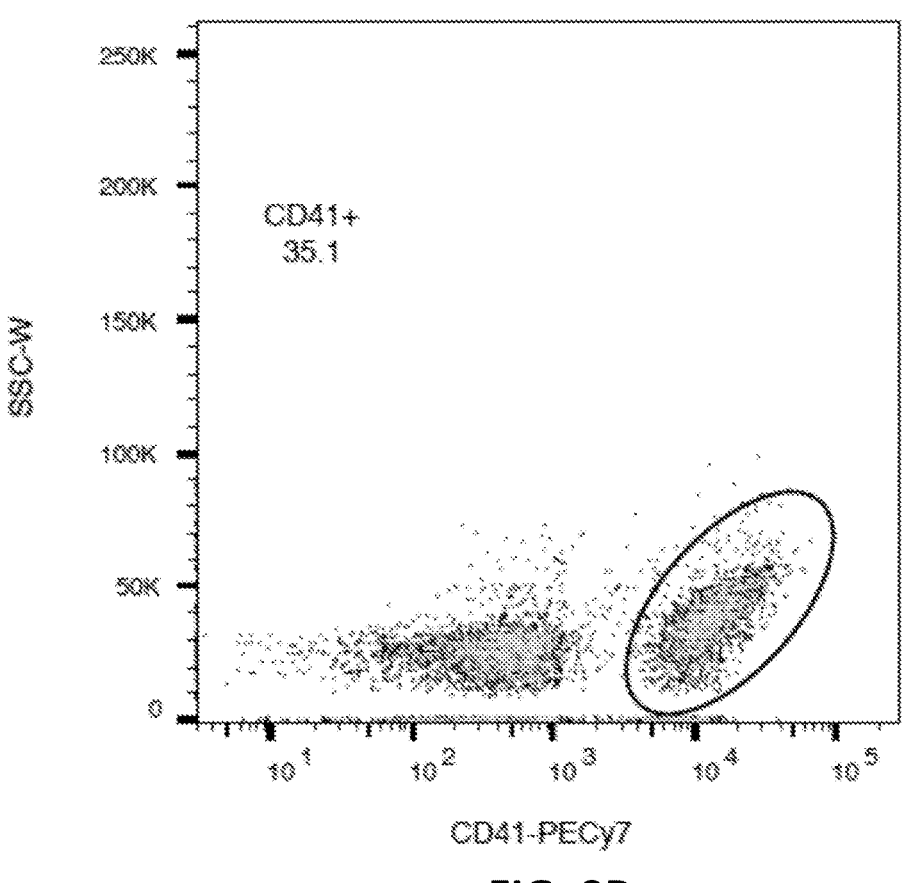
Figure 10:
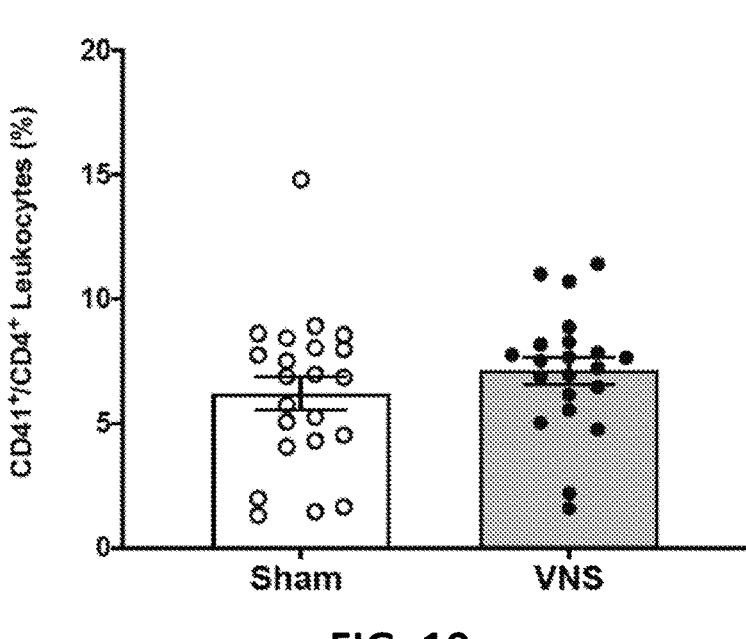
FIG. 10 and FIG. 11 illustrate additional experiments performed using flow cytometry involving leukocytes that express CD41, a platelet marker, and CD4, a T-cell marker, in spleen and blood. The results are summarized in FIGS. 10 and 11.
Figure 11:
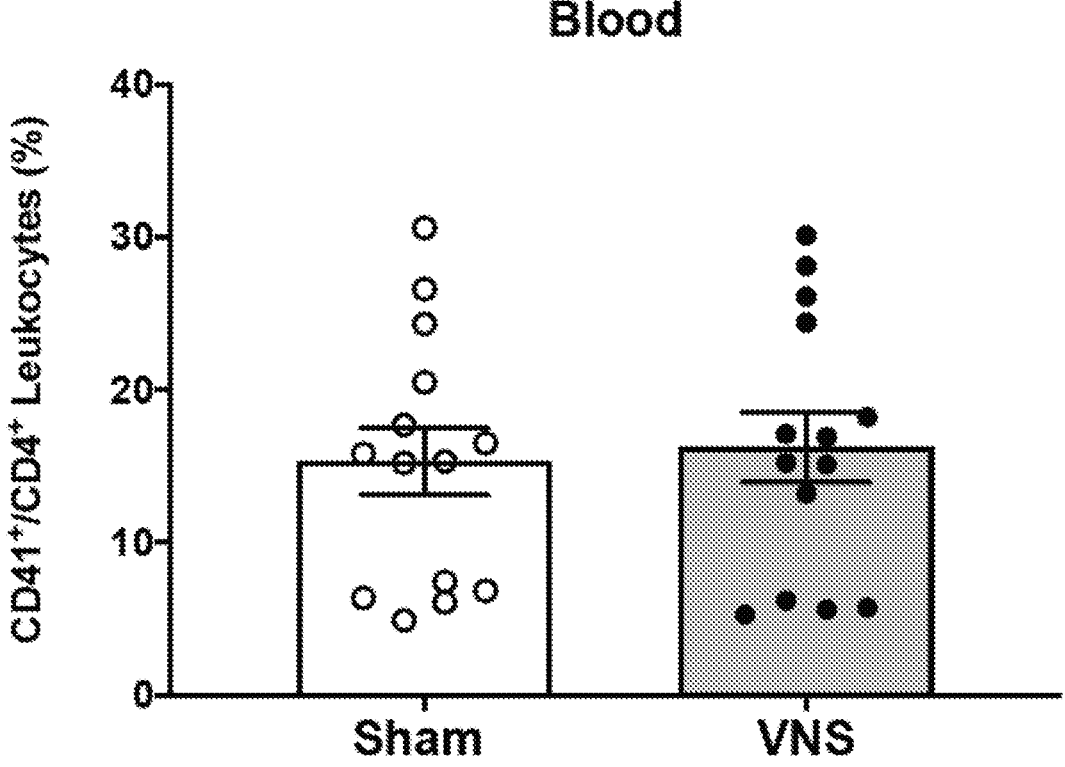

Systemic blood from the inferior vena cava is collected 17 minutes after vagus nerve stimulation (5 minutes) into Tris buffered saline (20 mM Tris-HCl, 137 mM NaCl, pH 7.3) containing 20 U/mL heparin. Heparinized whole blood is then diluted with modified Tyrode's Buffer (134 mM NaCl, 0.34 mM Na2HPO4, 2.9 mM KCl, 12 mM NaHCO3 20 mM Hepes, pH 7.0 with 5 mM glucose, 0.35% BSA). On flow cytometry (BD FACSymphony A3, BD LSRFortessa), platelets are initially identified via forward and side scatter plots (FSC-A/SSC-A) followed by anti-CD41a marker (BioLegend) (FIGS. 9A-9B). Platelets are then stimulated ex vivo with thrombin (1 U/ml, Sigma-Aldrich), collagen (0.5 or 5 ug/ml, Sigma-Aldrich), or ADP (20 ug/ml Thermo Scientific), and stained with antibodies against CD62P (P-Selectin) (BioLegend), active GPIIb/IIIa (Emfret Analytics), and phosphatidylserine (Millipore Sigma). In separate experiments, non-stimulated platelets are stained with anti-nicotinic acetylcholine receptor a7 (CHRNA7) (extracellular)-FITC antibody (Alomone Labs). Flow cytometry data is then collected (BD FACSDiva Software) and analyzed (FlowJo 10.8.1).

Thrombin Generation

Animals receive vagus nerve stimulation followed by tail warming in a 37° C. water bath for five minutes. The tail is transected where its diameter was 3 mm, and allowed to bleed freely into citrated tubes to collect local shed blood. Systemic blood from the inferior vena cava is then collected directly into citrated tubes. Blood is centrifuged for 15 minutes at 1500 g and plasma stored at –80° C. until assay. Thrombin generation is determined by measurement of thrombin-antithrombin (TAT) complex via commercially available ELISA (Abcam, Cambridge, MA).

Factor VIII Activity

Animals receive vagus nerve stimulation (5 minutes) or sham stimulation followed by tail warming in a 37° C. water bath for five minutes. Systemic blood is collected via cardiac puncture after 7 minutes. Blood is anticoagulated with sodium citrate and centrifuged at 1500 g for 15 min. Platelet poor plasma is stored at –80° C. until assay. Factor VIII activity is determined via standard clinical assay.

Lung Histology

Following tail transection and bleeding time measurement, lung tissue is collected. Briefly, lungs are inflated with 10% formalin by atmospheric pressure, excised, embedded in paraffin, sectioned at 6-7 μm and stained with hematoxylin and eosin. A board-certified thoracic pathologist blinded to the treatment assesses histologic sections for the presence of microthrombi and inflammation. Pictomicrographs are collected with a Zeiss Apotome connected to a computer with Zeiss AxioVision installed (Carl Zeiss Microscopy GmbH, Jena, Germany).

Platelet Adoptive Transfer

Male aged 8-12 week old C57BL/6 mice (Taconic Biosciences, Hudson, NY) are anesthetized with ketamine/xylazine and receive vagus nerve stimulation (5 minutes) or sham stimulation as described above. After 17 minutes, systemic blood is collected from the inferior vena cava into Tris buffer saline containing 20 U/mL Heparin. Heparinized blood is centrifuged for five minutes at 500 g. Platelet rich plasma (PRP) is transferred to a clean tube and centrifuged again for eight minutes at 300 g. PRP of all mice from each stimulation group is combined and centrifuged for five minutes at 1300 g. The platelet pellet is suspended in 0.9% normal saline with 5% BSA. Final platelet concentration is determined by flow cytometry. Male aged 8-12 week old C57BL/6 mice are anesthetized with ketamine/xylazine, receive donor platelets (6×108 platelets/200 μL, r.o.), and after nine minutes undergo tail transection.

ChAT-eGFP+ T-Cell Adoptive Transfer

Transgenic ChATBAC-eGFP mice (The Jackson Laboratory, Bar Harbor, ME) are euthanized via CO2 asphyxiation followed by splenic harvest. Spleens are passed through a 40 μm cell strainer, followed by red blood cell lysis with ACK buffer (Lonza, Allendale, NJ), and then passage through a CD4+ negative selection column (Miltenyi Biotech, Bergisch Gladbach, Germany). Eluted cells are treated with Fc block, anti-CD19 (BD Pharmingen, San Jose, CA) and anti-CD62L (eBioscience, San Diego, CA). Stained cells are then negative selected for these markers by FACS where this sub-population is divided into ChAT-eGFP+ and ChAT-eGFP–. Each population is suspended in 0.9% normal saline with 5% BSA and 150,000 cells are injected into the peritoneum of male aged 8-10 week old BALB/Nu mice (Taconic Biosciences, Hudson, NY). After 5 days, recipient nude mice receive vagus nerve stimulation (5 minutes) or sham stimulation before tail transection.

Platelet Ca2+ Flux

Male aged 8-12 week old C57BL/6 mice (Taconic Biosciences, Hudson, NY) are anesthetized with ketamine/xylazine and receive vagus nerve stimulation (1 V, 30 Hz, 2 ms, 5 minutes) or sham stimulation as described above. Harvested circulating platelets are washed and loaded with Oregon Green BAPTA-1, AM and FuraRed, AM. Platelets are resuspended in Tyrode's buffer containing 2 mM Ca2+ and baseline calcium concentrations are measured by flow cytometry.

Cell Counts

Animals are anesthetized with ketamine (144 mg/kg, i.p.) and xylazine (14 mg/kg, i.p.) as described above. Circulating blood from the inferior vena cava is collected seven minutes after vagus nerve stimulation or sham stimulation, placed into standard EDTA tubes, and complete blood count is determined using a Cell-Dyn 3700 Blood Analyzer.

Statistical Analysis

All data are presented as mean±s.e.m, and p<0.05 is considered significant. n represents the number of animals in each experiment, as detailed in the figure legends. Animals were randomly allocated into experimental groups. All measurements were taken from distinct samples, where appropriate. Statistical significance was determined by one-way ANOVA (Tukey) for three groups or unpaired, two-tailed Student's t-test for two groups. Statistical analyses were performed, and data presented using GraphPad Prism 8 (GraphPad Software), BD FACSDiva software (BD Biosciences), and FlowJo 10 (LLC).

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.5% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of accelerating clot formation and increasing clot deposition in a hemophiliac subject, the method comprising:

implanting a vagal nerve stimulator (VNS) in the hemophiliac subject, wherein the hemophiliac subject has developed antibodies to factor VIII and has not been administered a clotting factor within the last 48 hours; and stimulating the vagus nerve of said subject in a manner that increases platelet intracellular calcium and/or activates splenic acetylcholine-synthesizing T lymphocytes using the implanted VNS.

2. The method of claim 1, wherein the vagus nerve stimulation does not increase systemic factor VIII activity in the subject.

3. The method of claim 1, wherein the subject has not been administered the clotting factor within the last 48 hours.

4. The method of claim 1, wherein the stimulating comprises stimulating in an ongoing manner.

5. A method of accelerating clot formation and increasing clot deposition in a hemophiliac subject, the method comprising:

implanting a vagal nerve stimulator (VNS) in the hemophiliac subject, wherein the hemophiliac subject has developed antibodies to factor VIII and has not been administered a clotting factor within the last 48 hours; and activating platelets expressing surface $\alpha7nAChR$ by stimulating the vagus nerve of the hemophiliac subject using the implanted VNS.

* * * * *